(12) United States Patent
Todderud et al.

(10) Patent No.: US 7,198,911 B2
(45) Date of Patent: Apr. 3, 2007

(54) IDENTIFICATION AND CLONING OF A NOVEL HUMAN GENE, RET16, INVOLVED IN THE INTRACELLULAR SIGNALING CASCADE

(75) Inventors: C. Gordon Todderud, Newtown, PA (US); Joshua Finger, San Marcos, CA (US); Jill Rillema, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 535 days.

(21) Appl. No.: 10/077,111

(22) Filed: Feb. 15, 2002

(65) Prior Publication Data

US 2002/0187492 A1    Dec. 12, 2002

Related U.S. Application Data

(60) Provisional application No. 60/294,181, filed on May 29, 2001, provisional application No. 60/269,366, filed on Feb. 16, 2001.

(51) Int. Cl.
| | |
|---|---|
| C12P 12/06 | (2006.01) |
| C12Q 1/68 | (2006.01) |
| C12N 15/63 | (2006.01) |
| C07H 21/02 | (2006.01) |
| C07H 21/04 | (2006.01) |

(52) U.S. Cl. .................. 435/69.1; 435/6; 435/91.1; 435/320.1; 435/455; 536/23.1; 536/23.5

(58) Field of Classification Search ............ 435/6, 435/91.1, 91.31, 455, 458, 320.1, 70.1, 69.1, 435/375; 536/23.1, 24.5, 23.5; 530/300, 530/350

See application file for complete search history.

(56) References Cited

U.S. PATENT DOCUMENTS

| 6,114,517 A | 9/2000 | Monia et al. |
| 6,569,662 B1 * | 5/2003 | Tang et al. .............. 435/212 |

FOREIGN PATENT DOCUMENTS

WO    WO 01/05970    1/2001

WO    WO 01/53312    7/2001

OTHER PUBLICATIONS

F.S. Collins, Proc. Natl. Acad. Sci., vol. 99, No. 26, pp. 16,899-16,903 (2002).*
Carninci et al. (2000) Genome Research 10:1617-1630.
Carninci et al. (1999) Methods in Enzymology 303:19-44.
Shibata et al. (2000) Genome Research 10:1757-1771.
Nature (2001) 409:685-690.
NCBI Accession No. XP 087231.
NCBI Accession No. BAB27588.
NCBI Accession No. AAH29520.
NCBI Entrez Accession No. XP_087231, NCBI Annotation Project, Aug. 1, 2002.
NCBI Entrez Accession No. AAH29520, Strausberg, R., May 16, 2002.
NCBI Entrez Accession No. BAB27588, Carninci, P. et al., Jan. 19, 2002.
Database Geneseq, No. AAI58876, Novel Nucleic Acids and Polypeptides, Useful for Treating Disorders Such as Central Nervous System Injuries, Tang, et al. Jul. 26, 2001.
Owens, R. et al., "The in vivo and in vitro characterization of an engineered human antibody to E-selectin", Immunotechnology, vol. 3, pp. 107-116 (1997).
Trottein, F. et al., "*Schistosoma mansoni* schistosomula reduce E-selectin and VCAM-1 expression in TNF-α-stimulated lung microvascular endothelial cells by interfering with the NF-$_\chi$B pathway", Eur. J. Immunol., vol. 29, pp. 3691-3701 (1999).
NCBI Entrez Accession No. AA164914 (gi:1741091) Hillier, et al. Dec. 18, 1996.
NCBI Entrez Accession No. AAM39720 (gi:21111382) da Silva, et al. May 23, 2002.

* cited by examiner

*Primary Examiner*—Jane Zara
(74) *Attorney, Agent, or Firm*—Nickki L. Parlet; Stephen C. D'Amico

(57) ABSTRACT

The present invention describes a newly discovered polynucleotide encoding a protein involved in the cell signaling cascade, called RET16, cloned, isolated and identified from TNF-alpha stimulated human microvascular endothelial cells, as well as mouse and rat RET16 orthologs thereof. Also described are the RET16 polypeptide sequence, expression vectors, host cells, agonists, antagonists, antisense molecules, and antibodies related to the polynucleotide and/or polypeptide of the present invention. Methods for screening for modulators, particularly inhibitors, of the human RET16 protein, and use of the RET16 polynucleotide and polypeptide for therapeutics and diagnostics are described.

7 Claims, 31 Drawing Sheets

FIG. 1

```
   1  gcctgttccc tctgctctgg gtctccgccg gcgcccgccc cgccagcctc
  51  acctgcgcgg cacgtgaccc gcaccgcccg tgggcacctt gaaggcggat
 101  cccgcgcgcc cccgctcctg caggctgttt ttcttcaaat aaagaacatg
 151  gtgaaactga ttcacacatt agctgatcat ggtgacgatg tcaactgctg
 201  tgccttctcc ttttccctct tggctacttg ctccttggac aaaacaattc
 251  gcctgtactc gttacgtgac tttactgaac tgccacattc tccattgaag
 301  tttcatacct atgctgtcca ctgctgctgt ttctcccctt caggacatat
 351  tttggcatcg tgttcaacag atggtaccac tgtcctatgg aatactgaaa
 401  atggacagat gctggcagtg atggaacagc ctagtggcag ccctgtgagg
 451  gtttgccagt tttcccagac tccacgtgt ttggcatcag gggcagctga
 501  tggaactgtg gttttgtgga atgcacagtc atacaaatta tatagatgtg
 551  gtagtgttaa agatggctcc ttggcggcat gtgcattttc tcctaatgga
 601  agcttctttg tcactggctc ctcatgtggt gatttaacag tgtgggatga
 651  taaaatgagg tgtctgcata gtgaaaaagc acatgatctt ggaattacct
 701  gctgcgattt ttcttcacag ccagtttctg atggagaaca aggtcttcag
 751  ttttttcgac tggcatcatg tggtcaggat tgccaagtca aatttggat
 801  tgtttctttt acccatatct taggttttga attaaaatat aaaagtacac
 851  tgagtgggca ctgtgctcct gttctggctt gtgcttttc ccatgatggg
 901  cagatgctag tctcagggtc agtggataag tctgtcatag tatatgatac
 951  taatactgag aatatacttc acacattgac tcagcacacc aggtatgtca
1001  caacttgtgc ttttgcacct aataccctt tacttgctac tggttcaatg
1051  gacaaaacag tgaacatctg gcaatttgac ctggaaacac tttgccaagc
1101  aaggcgcaca gaacatcagc tgaagcaatt taccgaagat tggtcagagg
1151  aggatgtctc aacatggctt tgtgcacaag atttaaaaga tcttgttggt
1201  attttcaaga tgaataacat tgatggaaaa gaactgttga atcttacaaa
1251  agaaagtctg gctgatgatt tgaaaattga atctctagga ctgcgtagta
1301  aagtgctgag gaaaattgaa gagctcagga ccaaggttaa atccctttct
1351  tcaggaattc ctgatgaatt tatatgtcca ataactagag aacttatgaa
1401  agatccggtc atcgcatcag atggctattc atatgaaaag gaagcaatgg
1451  aaaattggat cagcaaaaag aaacgtacaa gtcccatgac aaatcttgtt
1501  cttccttcag cggtacttac accaaatagg actctgaaaa tggccatcaa
1551  tagatggctg agagacacacc aaaagtaaaa ttgttgatat tgtattattt
1601  atatttcag tgatctcatt tgaatgattt ataggtaaat actaatcaga
1651  cattattaaa agcaaaacag gaaaaggta aacttcttaa atttagttac
1701  ctataaaaat tgtcaatttt cattctttaa aaaacacatg gacttactat
1751  aaaagccttt ttgtactagt gaaaagaatc ttcagctata tagaaataaa
1801  gttatacttt aaaaaaaa
```

FIG. 2

```
  1   MVKLIHTLAD HGDDVNCCAF SFSLLATCSL DKTIRLYSLR
 41   DFTELPHSPL KFHTYAVHCC CFSPSGHILA SCSTDGTTVL
 81   WNTENGQMLA VMEQPSGSPV RVCQFSPDST CLASGAADGT
121   VVLWNAQSYK LYRCGSVKDG SLAACAFSPN GSFFVTGSSC
161   GDLTVWDDKM RCLHSEKAHD LGITCCDFSS QPVSDGEQGL
201   QFFRLASCGQ DCQVKIWIVS FTHILGFELK YKSTLSGHCA
241   PVLACAFSHD GQMLVSGSVD KSVIVYDTNT ENILHTLTQH
281   TRYVTTCAFA PNTLLLATGS MDKTVNIWQF DLETLCQARR
321   TEHQLKQFTE DWSEEDVSTW LCAQDLKDLV GIFKMNNIDG
361   KELLNLTKES LADDLKIESL GLRSKVLRKI EELRTKVKSL
401   SSGIPDEFIC PITRELMKDP VIASDGYSYE KEAMENWISK
441   KKRTSPMTNL VLPSAVLTPN RTLKMAINRW LETHQK
```

FIG. 3

```
atggtgaaactgattcacacattagctgatcatggtgacgatgtcaactgctgtgccttc
 M  V  K  L  I  H  T  L  A  D  H  G  D  D  V  N  C  C  A  F
tccttttccctcttggctacttgctccttggacaaaacaattcgcctgtactcgttacgt
 S  F  S  L  L  A  T  C  S  L  D  K  T  I  R  L  Y  S  L  R
gactttactgaactgccacattctccattgaagtttcatacctatgctgtccactgctgc
 D  F  T  E  L  P  H  S  P  L  K  F  H  T  Y  A  V  H  C  C
tgtttctccccttcaggacatattttggcatcgtgttcaacagatggtaccactgtccta
 C  F  S  P  S  G  H  I  L  A  S  C  S  T  D  G  T  T  V  L
tggaatactgaaaatggacagatgctggcagtgatggaacagcctagtggcagccctgtg
 W  N  T  E  N  G  Q  M  L  A  V  M  E  Q  P  S  G  S  P  V
agggtttgccagttttccccagactccacgtgtttggcatcaggggcagctgatggaact
 R  V  C  Q  F  S  P  D  S  T  C  L  A  S  G  A  A  D  G  T
gtggttttgtggaatgcacagtcatacaaattatatagatgtggtagtgttaaagatggc
 V  V  L  W  N  A  Q  S  Y  K  L  Y  R  C  G  S  V  K  D  G
tccttggcggcatgtgcattttctcctaatggaagcttctttgtcactggctcctcatgt
 S  L  A  A  C  A  F  S  P  N  G  S  F  F  V  T  G  S  S  C
ggtgatttaacagtgtgggatgataaaatgaggtgtctgcatagtgaaaaagcacatgat
 G  D  L  T  V  W  D  D  K  M  R  C  L  H  S  E  K  A  H  D
cttggaattacctgctgcgattttcttcacagccagtttctgatggagaacaaggtctt
 L  G  I  T  C  C  D  F  S  S  Q  P  V  S  D  G  E  Q  G  L
cagttttttcgactggcatcatgtggtcaggattgccaagtcaaaatttggattgtttct
 Q  F  F  R  L  A  S  C  G  Q  D  C  Q  V  K  I  W  I  V  S
tttacccatatcttaggttttgaattaaaatataaaagtacactgagtgggcactgtgct
 F  T  H  I  L  G  F  E  L  K  Y  K  S  T  L  S  G  H  C  A
cctgttctggcttgtgcttttcccatgatgggcagatgctagtctcagggtcagtggat
 P  V  L  A  C  F  S  H  D  G  Q  M  L  V  S  G  S  V  D
aagtctgtcatagtatatgatactaatactgagaatatacttcacacattgactcagcac
 K  S  V  I  V  Y  D  T  N  T  E  N  I  L  H  T  L  T  Q  H
accaggtatgtcacaacttgtgcttttgcacctaataccctttacttgctactggttca
 T  R  Y  V  T  T  C  A  F  A  P  N  T  L  L  A  T  G  S
atggacaaaacagtgaacatctggcaatttgacctggaaacactttgccaagcaaggcgc
 M  D  K  T  V  N  I  W  Q  F  D  L  E  T  L  C  Q  A  R  R
acagaacatcagctgaagcaatttaccgaagattggtcagaggaggatgtctcaacatgg
 T  E  H  Q  L  K  Q  F  T  E  D  W  S  E  E  D  V  S  T  W
ctttgtgcacaagatttaaaagatcttgttggtattttcaagatgaataacattgatgga
 L  C  A  Q  D  L  K  D  L  V  G  I  F  K  M  N  N  I  D  G
aaagaactgttgaatcttacaaaagaaagtctggctgatgatttgaaaattgaatctcta
 K  E  L  L  N  L  T  K  E  S  L  A  D  D  L  K  I  E  S  L
ggactgcgtagtaaagtgctgaggaaaattgaagagctcaggaccaaggttaaatccctt
 G  L  R  S  K  V  L  R  K  I  E  E  L  R  T  K  V  K  S  L
tcttcaggaattcctgatgaatttatatgtccaataactagagaacttatgaaagatccg
 S  S  G  I  P  D  E  F  I  C  P  I  T  R  E  L  M  K  D  P
gtcatcgcatcagatggctattcatatgaaaaggaagcaatggaaaattggatcagcaaa
 V  I  A  S  D  G  Y  S  Y  E  K  E  A  M  E  N  W  I  S  K
aagaaacgtacaagtcccatgacaaatcttgttcttccttcagcggtacttacaccaaat
 K  K  R  T  S  P  M  T  N  L  V  L  P  S  A  V  L  T  P  N
aggactctgaaaatggccatcaatagatggctggagacacaccaaaagtaa
 R  T  L  K  M  A  I  N  R  W  L  E  T  H  Q  K
```

FIG. 4A

```
gaattcggcttttcacctgcgcggcacgtgacccgcaccgcccgtgggcaccttg
aaggcggatcccgcgcgccccgctcctgcaggctgttttcttcaaataaaga
acatggtgaaactgattcacacattagctgatcatggtgacgatgtcaactgct
gtgccttctccttttcctcttggctacttgctccttggacaaaacaattcgcc
tgtactcgttacgtgactttactgaactgccacattctccattgaagtttcata
cctatgctgtccactgctgctgtttctcccttcaggacatatttggcatcgt
gttcaacagatggtaccactgtcctatggaatactgaaaatggacagatgctgg
cagtgatggaacagcctagtggcagccctgtgagggtttgccagttttcccag
actccacgtgtttggcatcaggggcagctgatggaactgtggttttgtggaatg
cacagtcatacaaattatatagatgtggtagtgttaaagatggctccttggcgg
catgtgcattttctcctaatggaagcttctttgtcactggctcctcatgtggtg
atttaacagtgtgggatgataaaatgaggtgtctgcatagtgaaaaagcacatg
atcttggaattacctgctgcgattttcttcacagccagtttctgatggagaac
aaggtcttcagttttttcgactggcatcatgtggtcaggattgccaagtcaaaa
tttggattgtttcttttacccatatcttaggttttgaattaaaatataaagta
cactgagtgggcactgtgctcctgttctggcttgtgcttttcccgtgatgggc
agatgctagtctcagggtcagtggataagtctgtcatagtatgatactaata
ctgagaatatacttcacacattgactcagcacaccaggtatgtcacaacttgt
cttttgcacctaatacccttttacttgctactggttcaatggacaaaacagtga
acatctggcaatttgacctggaaacactttgccaagcaaggcgcacagaacatc
agctgaagcaatttaccgaagattggtcagaggaggatgtctcaacatggcttt
gtgcacaagatttaaagatcttgttggtattttcaagatgaataacattgatg
gaaaagaactgttaatcttacaaagaaagtctggctgatgatttgaaaattg
aatctctaggactgcgtagtaaagtgctgaggaaattgaagagctcaggacca
aggttaaatccctttcttcaggaattcctgatgaatttatatgtccaataacta
gagaacttatgaaagatccggtcatcgcatcagatggctattcatatgaaagg
aagcaatggaaaattggatcagcaaaagaaacgtacaagtcccatgacaaatc
ttgttcttccttcagcggtacttacaccaataggactctgaaaatggccatca
atagatggctggagacacaccaaaagtaaaagccgaattc
(1532 bp)
```

FIG. 4B

IRLSPARHVTRTARGHLEGGSRAPPLLQAVFLQIKNMVKLIHTLADHGDDVNCCAFS

FSLLATCSLDKTIRLYSLRDFTELPHSPLKFHTYAVHCCCFSPSGHILASCSTDGTT

VLWNTENGQMLAVMEQPSGSPVRVCQFSPDSTCLASGAADGTVVLWNAQSYKLYRCG

SVKDGSLAACAFSPNGSFFVTGSSCGDLTVWDDKMRCLHSEKAHDLGITCCDFSSQP

VSDGEQGLQFFRLASCGQDCQVKIWIVSFTHILGFELKYKSTLSGHCAPVLACAFSR

DGQMLVSGSVDKSVIVYDTNTENILHTLTQHTRYVTTCAFAPNTLLLATGSMDKTVN

IWQFDLETLCQARRTEHQLKQFTEDWSEEDVSTWLCAQDLKDLVGIFKMNNIDGKEL

LNLTKESLADDLKIESLGLRSKVLRKIEELRTKVKSLSSGIPDEFICPITRELMKDP

VIASDGYSYEKEAMENWISKKKRTSPMTNLVLPSAVLTPNRTLKMAINRWLETHQK.

FIG. 4C

```
  1  acactgagtg ggcactgtgc tcctgttctg gcttgtgctt tttcccatga
 51  tgggcagatg ctagtctcag ggtcagtgga taagtctgtc atagtatatg
101  atactaatac tgagaatata cttcacacat tgactcagca caccaggtat
151  gtcacaactt gtgcttttgc acctaatacc cttttacttg ctactggttc
201  aatggacaaa acagtgaaca tctggcaatt tgacctggaa acactttgcc
251  aagcaaggcg cacagaacat cagctgaagc aatttaccga agattggtca
301  gaggaggatg tctcaacatg gctttgtgca caagatttaa aagatcttgt
351  tggtattttc aagatgaata acattgatgg aaaagaactg ttgaatctta
401  caaaagaaag tctggctgat gatttgaaaa ttgaatctct aggactgcgt
451  agtaaagtgc tgaggaaaat tgaagagctc aggaccaagg ttaaatccct
501  ttcttcagga attcctgatg aatttatatg tccataact agagaactta
551  tgaaagatcc ggtcatcgca tcagatggct attcatatga aaaggaagca
601  atggaaaatt ggatcagcaa aaagaaacgt
```

FIG. 5

```
ttactttgtgtgaggaacatggtgaggttgattcacacgctggctgatcacggggatgacgt
cagctgctgcgccttctcggctgccctcctggccacctgctccttggacaagaccatccgtc
tgtactccctaagtgactttgttgaactgccgtactccccgctgaagttccacacctatgct
gtccactgctgctgtttctcaccctcaggacacgttttagcatcgtgctcgacagacgggac
cacggtgctgtggagctcgcacagcggacacacctgaccgtgttggagcagccggtggca
gccctgtgcgcgtctgttgcttttccccagactctgcctacctagcgtcagggctgccgat
ggatccattgctttgtggaatgcacagacatacaaactatataggtgtggtagtgtcaagga
tagctcattggtggcctgtgcgttttctcccgatggaggcctctttgtcactggctcctcgg
gcggggacttgacagtgtgggatgacagaatgaggtgtctacacagcgagaaggcgcacgat
ctcgggatcacctgctgcagcttttcctcacagcctctctctggcggagaaggcctccagtc
ttaccagttggcgtcatgtggtcaagactgtgaaatcaaactctgggctgttactattaccc
gtgtcttaggctttgaattaaaatataaaagcacactaagtgggcactgcgccctgttctg
gcctgtgcttttcacatgatggaaagatgcttgcatcggggtcagtggataaatctgtcat
catacatggtatcggccctcagagtgtgctacacacgctgactcagcataccaggtatgtta
cgacttgtgcgtttgcacccaacactctcttacttgctactggttcaatggacaagacagtg
aacatttggcagtttgacctggaaacaccttgccaagcaggaagcatgaacgacccgctgaa
acatttcactgaagaatggtcagaggaggatgtctccgtgtggcttcgtgctcaaggcttgg
aagacctcgtcggtattttcagggcaaacaacatcgatgggaagaactattgcatctcaca
aaggaaagtctggctggtgatttgaaaatcgaatctctagggctgcgcagcaaagtcctgag
gagtattgaagagctcagggccaagatggattccctctcttccggaatccctgacgagttca
tctgcccaataaccagagaactcatgaaggaccccgtcatcgcatcagatggctactcctac
gagagagaagcaatggaaagctggatccacaagaagaagcgtacgagccccatgacaaattt
ggctctcccttcactggtactgaccccaaacaggacactgaagatggccatcaaccgatggc
tggagacgcacgagaagtgaacgcgttcacaggcatcggatccactttcagtgatgccctgc
aaatgattcaaaatgctaagcagccatcacgaaagcaaaataaaaggaaaagacaaatgttc
aattcagttacttttaaaaactgtaaattatgagcagggcagtggtggtgcccacctttaat
cccagcactcaggaggcagagacaggtggatctccaggatcaggagttccaggacagccag
tttatagggcaagtctcaggacggccaaggctacacagagaaaccctgtctcaaaaaaccca
aaacccaaaaaaaaaaaaaaaaaagtcaattatctttaaaacacagatttatatatctatt
gtcattgctatttctgtaaaggtgaaatatttttttttttgcaataatgagaaactatgta
gaaataaaacttcactatgactttaaaaaaaaaaaaaaaaa
```

FIG. 6

MVRLIHTLADHGDDVSCCAFSAALLATCSLDKTIRLYSLSDFVELPYSPLKFHT

YAVHCCCFSPSGHVLASCSTDGTTVLWSSHSGHTLTVLEQPGGSPVRVCCF

SPDSAYLASGAADGSIALWNAQTYKLYRCGSVKDSSLVACAFSPDGGLFVTG

SSGGDLTVWDDRMRCLHSEKAHDLGITCCSFSSQPLSGGEGLQSYQLASCG

QDCEIKLWAVTITRVLGFELKYKSTLSGHCAPVLACAFSHDGKMLASGSVDKS

VIIHGIGPQSVLHTLTQHTRYVTTCAFAPNTLLLATGSMDKTVNIWQFDLETPC

QAGSMNDPLKHFTEEWSEEDVSVWLRAQGLEDLVGIFRANNIDGKELLHLTK

ESLAGDLKIESLGLRSKVLRSIEELRAKMDSLSSGIPDEFICPITRELMKDPVIA

SDGYSYEREAMESWIHKKKRTSPMTNLALPSLVLTPNRTLKMAINRWLETHEK

FIG. 10A

```
   1 .....MVKLIHTLADHGDDVNCCAFS..FSLLATCSLDKTIRLYSLRDFT   43
           || || |  |||    .|. | ||||:::      |
 951 IWDAASGTCTQTLEGHGSSVLSVAFSPDGQRVASGSGDKTIKIWDTASGT 1000

44 ELPHSPLKFHTYAVHCCCFSPSGHILASCSTDGTTVLWNTENGQMLAVME   93
     |.|  .|    ||| |  .|| ||| |  :|.|  .|      :|
1001 ..CTQTLEGHGGSVWSVAFSPDGQRVASGSDDKTIKIWDTASGTCTQTLE 1048

94 QPSGSPVRVCQFSPDSTCLASGAADGTVVLWNAQSYKLYRCGSVKDGSLA  143
         |  |.  ||||  .|||. | |: :|.|| |     .     |.
1049 .GHGGWVQSVVFSPDGQRVASGSDDHTIKIWDAVSGTCTQTLEGHGDSVW 1097

144 ACAFSPNGSFFVTGSSCGDLTVWDDKM.RCLHSEKAHDLGITCCDFSSQP  192
     . ||||.|   .||   | |  : :||    |  . |   :        ||
1098 SVAFSPDGQRVASGSIDGTIKIWDAASGTCTQTLEGHGGWVHSVAFS... 1144

193 VSDGEQGLQFFRLASCGQDCQVKIWIVSFTHILGFELKYKSTLSGHCAPV  242
     ||:       |.||   |  :|||     .          || ||    |
1145 .PDGQ......RVASGSIDGTIKIWDAA.......SGTCTQTLEGHGGWV 1180

243 LACAFSHDGQMLVSGSVDKSVIVYDTNTENILHTLTQHTRYVTTCAFAPN  292
     . ||| |||  . ||| ||| ||.: ::||  .   ||  |  :|.||.|.
1181 QSVAFSPDGQRVASGSSDKTIKIWDTASGTCTQTLEGHGGWVQSVAFSPD 1230

293 TLLLATGSMDKTVNIWQFDLETLCQARRTEHQLKQFTEDWSEEDVSTWLC  342
     .|.|| | |: ||     | |             .|:.    :.| :
1231 GQRVASGSSDNTIKIWDTASGTCTQTLNVGSTATCLSFDYTNAYINTNIG 1280

343 AQDLKDLVGIFKMNNIDGKELLNLTKESLADDLKIESLGLRSKVLRKIEE  392
     :      .:| :     .    | |: .    ||    |
1281 RIQIATAT.MESLNQLSSPVCYSY...GLGQDHRWITCN.NQNVLWLPPE 1325

393 LRTKVKSLSSG..IPDEFICPITRELMKDPVIASDGYSYEKEAMENWISK  440
       | .:     :   :     |  |       |
1326 YHTSAFTMQGRKIVLGSYSGRIIIFLFSRDV.................. 1356
```

FIG. 10B

```
  1 .MVKLIHTLADHGDDVNCCAFS..FSLLATCSLDKTIRLYSLRDFTELPH  47
     ::: |  |   :      |||   ||||  | || | .: .    || |
451 NEPRILTT..DR..EAVAVAFSPGGSLLAGGSGDKLIHVWDVASGDEL.H  495

48 SPLKFHTYAVHCCCFSPSGHILASCSTDGTTVLWNTENGQMLAVMEQPSG  97
     . |.||  |    ||| |  :||| ||| | ||.   : || |   .
496 T.LEGHTDWVRAVAFSPDGALLASGSDDATVRLWDVAAAEERAVFEGHTH  544

98 SPVRVCQFSPDSTCLASGAADGTVVLWNAQSYKLYRCGSVKDGSLAACAF  147
     . :  ||||  . ||| . ||| . |||  . :             . |||
545 YVLDIA.FSPDGSMVASGSRDGTARLWNVATGTEHAVLKGHTDYVYAVAF  593

148 SPNGSFFVTGSSCGDLTVWD...DKMRCLHSEKAHDLGITCCDFSSQPVS  194
    ||.||   .|| |  : .||    || .  | .:       ||
594 SPDGSMVASGSRDGTIRLWDVATGKERDVLQAPAEN..VVSLAFS....P  637

195 DGEQGLQFFRLASCGQDCQVKIWIVSFTHILGFELKYKSTLSGHCAPVLA  244
    ||  .      | | |:|| .  |          | ||   ||
638 DGSMLVH.......GSDSTVHLWDVASGEAL.......HTFEGHTDWVRA  673

245 CAFSHDGQMLVSGSVDKSVIVYDTNTENILHTLTQHTRYVTTCAFAPNTL  294
    |||  || :|  ||| |:.: .:|   :    || || | . || |
674 VAFSPDGALLASGSDDRTIRLWDVAAQEEHTTLEGHTEPVHSVAFHPEGT  723

295 LLATGSMDKTVNIWQFDLETLCQARRTEHQLKQFTEDWSEEDVSTWLCAQ  344
    ||. | |  |:  ||     |
724 TLASASEDGTIRIWPIATE...........................  742
```

FIG. 10C

```
  1 MVKLIHTLADHGDDVNCCAFSFSLLATCSLDKTIRLYSLRDFTELPHSPL  50
    ||:||||||||||| |||||  |||||||||||||||||||| || |||:|||
  1 MVRLIHTLADHGDDVSCCAFSAALLATCSLDKTIRLYSLSDFVELPYSPL  50

51 KFHTYAVHCCCFSPSGHILASCSTDGTTVLWNTENGQMLAVMEQPSGSPV 100
    |||||||||||||||||:||||||||||||||..  .|  | |:||| ||||
 51 KFHTYAVHCCCFSPSGHVLASCSTDGTTVLWSSHSGHTLTVLEQPGGSPV 100

101 RVCQFSPDSTCLASGAADGTVVLWNAQSYKLYRCGSVKDGSLAACAFSPN 150
    ||| |||||  ||||||||-: |||||-||||||||||||| || ||||||·
101 RVCCFSPDSAYLASGAADGSIALWNAQTYKLYRCGSVKDSSLVACAFSPD 150

151 GSFFVTGSSCGDLTVWDDKMRCLHSEKAHDLGITCCDFSSQPVSDGEQGL 200
    |   ||||||  |||||||:|||||||||||||||||  |||||·| || ||
151 GGLFVTGSSGGDLTVWDDRMRCLHSEKAHDLGITCCSFSSQPLSGGE.GL 199

201 QFFRLASCGQDCQVKIWIVSFTHILGFELKYKSTLSGHCAPVLACAFSHD 250
    | :·||||||||::|:| |·  | :|||||||||||||||||||||||||||
200 QSYQLASCGQDCEIKLWAVTITRVLGFELKYKSTLSGHCAPVLACAFSHD 249

251 GQMLVSGSVDKSVIVYDTNTENILHTLTQHTRYVTTCAFAPNTLLLATGS 300
    |·|| |||||||||::    :·:||||||||||||||||||||||||||||
250 GKMLASGSVDKSVIIHGIGPQSVLHTLTQHTRYVTTCAFAPNTLLLATGS 299

301 MDKTVNIWQFDLETLCQARRTEHQLKQFTEDWSEEDVSTWLCAQDLKDLV 350
    |||||||||||||| |||    || |||:||||||| || || |·|||
300 MDKTVNIWQFDLETPCQAGSMNDPLKHFTEEWSEEDVSVWLRAQGLEDLV 349

351 GIFKMNNIDGKELLNLTKESLADDLKIESLGLRSKVLRKIEELRTKVKSL 400
    |||: |||||||||·|||||||| ||||||||||||||||| |·  ||
350 GIFRANNIDGKELLHLTKESLAGDLKIESLGLRSKVLRSIEELRAKMDSL 399

401 SSGIPDEFICPITRELMKDPVIASDGYSYEKEAMENWISKKKRTSPMTNL 450
    |||||||||||||||||||||||||||||:||||·|| ||||||||||||
400 SSGIPDEFICPITRELMKDPVIASDGYSYEREAMESWIHKKKRTSPMTNL 449

451 VLPSAVLTPNRTLKMAINRWLETHQK 476
    ||| |||||||||||||||||||||:|
450 ALPSLVLTPNRTLKMAINRWLETHEK 475
```

FIG. 10D

```
401 SSGIPDEFICPITRELMKDPVIASDGYSYEKEAMENWISKKKRTSPMTNL 450
        ||||||||||||||||||||||||||:||||·|| ||||||||||
  1 .....DEFICPITRELMKDPVIASDGYSYEREAMESWIHKKKRTSPMTNL 45

451 VLPSAVLTPNRTLKMAINRWLETHQK 476
    |||  |||||||||||||||||||||
 46 ALPSLVLTPNRTLKMAINRWLETHQK 71
```

| Clone Count | |
|---|---|
| 3 | kidney, mw/renal cell CA, 65M, m/KIDNTUT15 |
| 3 | kidney tumor, clear cell type cancer, pool, SUB, CGAP |
| 2 | breast, NF breast disease, 35F |
| 2 | brain, frontal, Huntington's, mw/CVA, 57M |
| 2 | prostate tumor, adenoCA, 66M, m/PROSNOT15, PROSDIN01 |
| 2 | lung, mw/spindle cell carcinoid, 62F |
| 2 | brain, sensory-motor cortex, aw/CHF, 35M |
| 2 | liver/spleen, fetal, 20wM, NORM, CGAP/WM/WN |
| 2 | kidney, pool, SUB, 3' CGAP |
| 1 | pituitary tumor, adenoma, pool, 3', CGAP |
| 1 | prostate, PIN, mw/cancer, M, m/PROSTUP03, 3' CGAP |
| 1 | colon, cecum/descending, polyposis, polyp, M/F, pool, NORM |
| 1 | esophagus tumor, adenoCA, 61M, NORM |
| 1 | ovary tumor, papillary serous CA, 64F, WM/WN |
| 1 | bronchial, epithelial cells, 23M, t/20% smoke 20 hr |
| 1 | T-B lymphoblast line, leukemia, untreated |
| 1 | paraganglion tumor, paraganglioma, aw/renal cell CA, 46M |
| 1 | sm intestine, ileum, mw/CUC, 42M |
| 1 | brain, hippocampus, AD |
| 1 | brain, hippocampus, aw/aortic aneurysm, 45F, 5RP |
| 1 | ovary, aw/leiomyomata, 43F |
| 1 | bladder tumor, TC CA, 72M |
| 1 | breast, mw/ductal adenoCA, aw/node mets, 46F, m/BRSTTUT15 |
| 1 | gallbladder, cholecystitis, cholelithiasis, 18F |
| 1 | prostate, mw/adenoCA, 68M, m/PROSTUT18 |
| 1 | T- lymphocytes, CD4+, pool, t/CD3 antibodies |
| 1 | lung tumor, mets granulosa cell tumor, 80F |
| 1 | breast, PF changes, mw/adenoCA, 45F, m/BRSTTUT08 |
| 1 | CML precursor line, K-562, 53F, t/5AZA 72 hr |
| 1 | lung tumor, adenoCA, 47M |
| 1 | colon, appendix, aw/leiomyomata, 37F |
| 1 | uterus, myometrium, mw/leiomyoma, 41F, NORM, m/UTRSTUT05 |
| 1 | esophagus tumor, adenoCA, 61M |
| 1 | colon tumor, adenoCA, 75M, m/COLNNOT01 |
| 1 | brain, temporal, mw/neuroepithelial tumor, epilepsy, 45M |
| 1 | brain, medulla, aw/CHF, 35M |
| 1 | kidney, 49M |
| 1 | uterus, endometrium, F, pool |
| 1 | paraganglion tumor, paraganglioma, aw/renal cell CA, 46M |
| 1 | prostate, AH, mw/adenoCA, node mets, 55M, Ig/N, m/PROSTUT16 |
| 1 | brain, neurogenic tumor line, SK-N-MC, neuroepithelioma, 14F |
| 1 | adrenal tumor, pheochromocytoma, 57F |
| 1 | brain, striatum/globus pallidus/putamen, aw/CHF, 81F, RP |
| 1 | bone marrow, tibia, aw/mets alveolar rhabdomyoSAR, 16M |
| 1 | thyroid, lymphocytic thyroiditis, mw/papillary CA, 30F |
| 1 | breast, mw/ductal CA, CA in situ, aw/node mets, 62F |
| 1 | liver tumor, mets neuroendocrine CA, 62F, m/ LIVRTMR01 |
| 1 | umb cord blood, mononuclear cells, t/IL-5 |
| 1 | uterus tumor, serous papillary CA, F, pooled, 3' CGAP |
| 1 | lung, fetal, 19w, NORM, CGAP/WM/WN |
| 1 | placenta, neonatal, F, NORM, WM |
| 1 | uterus, F, NORM, CGAP/WM/WN |
| 1 | pancreas tumor, adenoCA, 3' CGAP |
| 1 | brain, infant, 10wF, NORM, WM |
| 1 | testis, M, NORM, CGAP/WN |
| 1 | liver/spleen, fetal, 20wM, NORM, WM |
| 1 | mixed tissues, fetal lung, testis, B-cell, SUB, 3' CGAP/WN |

FIG. 13 tgacgagttcatctgcccaataaccagggaacttatgaaggaccccgtcatcgcatca
gatggctactcctacgagagagaagcaatggagagttggatccacaagaagaagcgca
cgagccccatgacaaacttggctcttccttcactggtactgaccccaaacaggactct
gaaaatggccatcaatcgatggctagagacgcatcagaagtgaacctgcccacaggca
tcgggtacactgtcagtgatgcccttcagatgattcaaaatgctaagcagccattaca
gaagcaaataaaagggaaggacagacgttaaatccagttacttttaaaaactgtaaac
tgtaagcaggtaagtggtggcgcacacctttaatcccagcactcaggaggcagaggca
ggtgggtctccatgaattccaggccagcctggtctatagggcgagttccaggacggca
aggctacacagagaaaccctgtctcaaaaacctaaagcaaaaaaaaaaaaaaaaa

FIG. 14

DEFICPITRELMKDPVIASDGYSYEREAMESWIHKKKRTSPMTNLALPSLVLTPNRTL
KMAINRWLETHQK

FIG. 15

```
HuRET16  MVKLIHTLADHGDDVNCCAFSFSLIATCSLDKTIRLYSLRDFTELPHSPL
muRET16  MVRLTHTLADHGDDVSCCAFSAALIATCSLDKTIRLYSLSDFVELPYSPL
rRET16   --------------------------------------------------

HuRET16  KFHTYAVHCCGFSPSGHILASCSTDGTTVLWNTENGQMLAVMEQPSGSPV
muRET16  KFHTYAVHCCGFSPSGHVLASCSTDGTTVLWSSHSGHTLTVLEQPGGSPV
rRET16   --------------------------------------------------

HuRET16  RVCQFSPDSTCLASGAADGTVVLWNAQSYKLYRCGSVKDGSLAACAFSPN
muRET16  RVCCFSPDSAYLASGAADGSIALWNAQTYKLYRCGSVKDSSLVACAFSPD
rRET16   --------------------------------------------------

HuRET16  GSFFVIGSSCGDLVWDDKMRCLHSEKAHDLGITCCDFSSQPVSDGEQGL
muRET16  GGLFVIGSSGGDLTVWDDRMRCLHSEKAHDLGITCCSFSSQPLSGGEGL
rRET16   --------------------------------------------------

HuRET16  QFFRLASCGQDCQVKIWIVSFTHILGFELKYKSTLSGHCAPVLACAFSHD
muRET16  QSYQLASCGQDCEIKLWAVTIIRVLGFELKYKSTLSGHCAPVLACAFSHD
rRET16   --------------------------------------------------

HuRET16  GQMIVSGSVDKSVVYDTNTENILHTLTQHTRYVTTCAFAPNTLLATGS
muRET16  GKMLASGSVDKSVIHGIGPQSVLHTLTQHTRYVTTCAFAPNTLLATGS
rRET16   --------------------------------------------------

HuRET16  MDKTVNIWCFDLETLCQARRTEHQLKQFTEDWSEEDVSTWLCAQDLKDLV
muRET16  MDKTVNIWCFDLETLPCQAGSMNDPLKHFIEEWSEEDVSVWLRAQGLEDLV
rRET16   --------------------------------------------------

HuRET16  GIFKMNNIDGKELNLTKESLADDLKIESLGLRSKVIRKEELRTKVKSL
muRET16  GIFRANNIDGKELHLTKESLAGDLKIESLGLRSKVLRSEELRAKMDSL
rRET16   --------------------------------------------------

HuRET16  SSGIPDEFICPITRELMKDPVIASDGYSYEKEAMENWISKKKRTSPMTNL
muRET16  SSGIPDEFICPLTRELMKDPVIASDGYSYEREAMESWIHKKKRTSPMINL
rRET16   -----DEFICPITRELMKDPVIASDGYSYEREAMESWIHKKKRTSPMTNL

HuRET16  VLPSAVLTPNRTLKMAINRWLETHQK
muRET16  ALPSLVLIPNRTLKMAINRWLETHEK
rRET16   ALPSLVLIPNRTLKMAINRWLETHQK
```

FIG. 16

```
RET16.1  M V K L I H T L A D H G D D V N C C A F S F S L L A T C S L D K T I R L Y S L R D F T E L P H S P L
RET16.2  M V K L I H T L A D H G D D V N C C A F S F S L L A T C S L D K T I R L Y S L R D F T E L P H S P L
RET16.3  M V K L I H T L A D H G D D V N C C A F S F S L L A T C S L D K T I R L Y S L R D F T E L P H S P L

RET16.1  K F H T Y A V H C C C F S P S G H I L A S C S T D G T T V L W N T E N G Q M L A V M E Q P S G S P V
RET16.2  K F H T Y A V H C C C F S P S G H I L A S C S T D G T T V L W N T E N G Q M L A V M E Q P S G S P V
RET16.3  K F H T Y A V H C C C F S P S G H I L A S C S T D G T T V L W N T E N G Q M L A V M E Q P S G S P V

RET16.1  R V C Q F S P D S T C L A S G A A D G T V V L W N A Q S Y K L Y R C G S V K D G S L A A C A F S P N
RET16.2  R V C Q F S P D S T C L A S G A A D G T V V L W N A Q S Y K L Y R C G S V K D G S L A A C A F S P N
RET16.3  R V C Q F S P D S T C L A S G A A D G T V V L W N A Q S Y K L Y R C G S V K D G S L A A C A F S P N

RET16.1  G S F F V T G S S C G D L T V W D D K M R C L H S E K A H D L G I T C C D F S S Q P V S D G E Q G L
RET16.2  G S F F V T G S S C G D L T V W D D K M R C L H S E K A H D L G I T C C D F S S Q P V S D G E Q G L
RET16.3  G S F F V T G S S C G D L T V W D D K M R C L H S E K A H D L G I T C C D F S S Q P V S D G E Q G L

RET16.1  Q F F R L A S C G Q D C Q V K I W I V S F T H I L G F E L K Y K S T L S G H C A P V L A C A F S R D
RET16.2  Q F F R L A S C G Q D C Q V K I W I V S F T H I L
RET16.3  Q F F R L A S C G Q D C Q V K I W I V S F T H I L G F E L K Y K S T L S G H C A P V L A C A F S H D

RET16.1  G Q M L V S G S V D K S V I V Y D T N T E N I L H T L T Q H T R Y V T T C A F A P N T L L L A T G S
RET16.2
RET16.3  G Q M L V S G S V D K S V I V Y D T N T E N I L H T L T Q H T R Y V T T C A F A P N T L L L A T G S

RET16.1  M D K T V N I W Q F D L E T L C Q A R R T E H Q L K Q F T E D W S E E D V S T W L C A Q D L K D L V
RET16.2                                A R R T E H Q L K Q F T E D W S E E V V S T W L C A Q D L K D L V
RET16.3  M D K T V N I W Q F D L E T L C Q A R R T E H Q L K Q F T E D W S E E D V S T W L C A Q D L K D L V

RET16.1  G I F K M N N I D G K E L L N L T K E S L A D D L K I
RET16.2  G I F K M N N I D G K E L L N L T K E S L A D D L K I
RET16.3  G I F K M N N I D G K E L L N L T K E S L A D D L K I G W S P L A W S C L T A A S T S W A Q V I L L

RET16.1          E S L G L R S K V L R K I E E L R T K V K S L S S G I P D E F I C P I T R E L M K D P V I A S
RET16.2          E S L G L R S K V L R K I E E L R T K V K S L S S G I P D E F I C P I T R E L M K D P V I A S
RET16.3  P R P Q S L G L R S K V L R K I E E L R T K V K S L S S G I P D E F I C P I T R E L M K D P V I A S

RET16.1  D G Y S Y E K E A M E N W I S K K K R T S P M T N L V L P S A V L T P N R T L K M A I N R W L E T H
RET16.2  D G Y S Y E K E A M E N W I S K K K R T S P M T N L V L P S A V L T P N R T L K M A I N R W L E T H
RET16.3  D G Y S Y E K E A M E N W I S K K K R T S P M T N L V L P S A V L T P N R T L K M A I N R W L E T H

RET16.1  Q K
RET16.2  Q K
RET16.3  Q K
```

FIG. 17

```
                              WD repeat 1
HuRET16.1  M V K L I H T L A D H G D D V N C C A F S F S L L A T C S L D K T I R L
MuRET16    M V R L I H T L A D H G D D V S C C A F S A A L L A T C S L D K T I R L
                              WD repeat 2
HuRET16.1  Y S L R D F T E L P H S P L K F H T Y A V H C C C F S P S G H I L A S C
MuRET16    Y S L S D F V E L P Y S P L K F H T Y A V H C C C F S P S G H V L A S C
                              WD repeat 3
HuRET16.1  S T D G T T V L W N T E N G Q M L A V M E Q P S G S P V R V C Q F S P D
MuRET16    S T D G T T V L W S S H S G H T L T V L E Q P G G S P V R V C C F S P D
                              WD repeat 4
HuRET16.1  S T C L A S G A A D G T V V L W N A Q S Y K L Y R C G S V K D G S L A A
MuRET16    S A Y L A S G A A D G S I A L W N A Q T Y K L Y R C G S V K D S S L V A
                              WD repeat 5
HuRET16.1  C A F S P N G S F F V T G S S C G D L T V W D D K M R C L H S E K A H D
MuRET16    C A F S P D G G L F V T G S S G G D L T V W D D R M R C L H S E K A H D HuRET16.1  L G I T C C D F S S Q P V S D G E Q G L Q F R L A S C G Q D C Q V K I
MuRET16    L G I T C C S F S S Q P L S G G E   G L Q S Y Q L A S C G Q D C E I K L
                              WD repeat 6
HuRET16.1  W I V S F T H I L G F E L K Y K S T L S G H C A P V L A C A F S H D G
MuRET16    W A V T I T R V L G F E L K Y K S T L S G H C A P V L A C A F S H D G K
                              WD repeat 7
HuRET16.1  M L V S G S V D K S V I V Y D T N T E N I L H T L T Q H T R Y V T T C A
MuRET16    M L A S G S V D K S V I I H G I G P Q S V L H T L T Q H T R Y V T T C A HuRET16.1  F A P N T L L L A T G S M D K T V N I W Q F D L E T L C Q A R R T E H Q
MuRET16    F A P N T L L L A T G S M D K T V N I W Q F D L E T P C Q A G S M N D P
                              SAM domain
HuRET16.1  L K Q F T E D W S E E D V S T W L C A Q D L K D L V G I F K M N N I D G
MuRET16    L K H F T E E W S E E D V S V W L R A Q G L E D L V G I F R A N N I D G HuRET16.1  K E L L N L T K E S L A D D L K I E S L G E R S K V L R K I E E L R T K
MuRET16    K E L L H L T K E S L A G D L K I E S L G L R S K V L R S I E E L R A K HuRET16.1  V K S L S S G I P D E F I C P I T R E L M K D P V I A S D G Y S Y E K E
MuRET16    M D S L S S G I P D E F I C P I T R E L M K D P V I A S D G Y S Y E R E HuRET16.1  A M E N W I S K K K R T S P M T N L V L P S A V L T P N R T L K M A I N
MuRET16    A M E S W I H K K K R T S P M T N L A L P S L V L T P N R T L K M A I N HuRET16.1  R W L E T H Q K
MuRET16    R W L E T H E K
```

FIG. 19A

```
gaattcggcttttcacctgcgcggcacgtgacccgcaccgcccgtgggcaccttgaaggcg
gatcccgcgcgccccgctcctgcaggctgttttcttcaaataaagaacatggtgaaac
tgattcacacattagctgatcatggtgacgatgtcaactgctgtgccttctccttttccc
tcttggctacttgctccttggacaaaacaattcgcctgtactcgttacgtgactttactg
aactgccacattctccattgaagtttcatacctatgctgtccactgctgctgtttctccc
cttcaggacatattttggcatcgtgttcaacagatggtaccactgtcctatggaatactg
aaaatggacagatgctggcagtgatggaacagcctagtggcagccctgtgagggtttgcc
agttttccccagactccacgtgtttggcatcaggggcagctgatggaactgtggttttgt
ggaatgcacagtcatacaaattatatagatgtggtagtgttaaagatggctccttggcgg
catgtgcattttctcctaatggaagcttctttgtcactggctcctcatgtggtgatttaa
cagtgtgggatgataaaatgaggtgtctgcatagtgaaaagcacatgatcttggaatta
cctgctgcattttcttcacagccagtttctgatggagaacaaggtcttcagtttttc
gactggcatcatgtggtcaggattgccaagtcaaaatttggattgtttcttttacccata
tcttagcaaggcgcacagaacatcagctgaagcaatttaccgaagattggtcagaggagg
tcgtctcaacatggctttgtgcacaagatttaaaagatcttgttggtattttcaagatga
ataacattgatggaaaagaactgttaatcttacaaaagaaagtctggctgatgatttga
aaattgaatctctaggactgcgtagtaaagtgctgaggaaaattgaagagctcaggacca
aggttaaatccctttcttcaggaattcctgatgaatttatatgtccaataactagagaac
ttatgaaagatccggtcatcgcatcagatggctattcatatgaaaggaagcaatggaaa
attggatcagcaaaaagaaacgtacaagtcccatgacaaatcttgttcttccttcagcgg
tacttacaccaaataggactctgaaaatggccatcaatagatggctggagacacaccaaa
agtaaagaattc
```

FIG. 19B

```
MVKLIHTLADHGDDVNCCAFSFSLLATCSLDKTIRLYSLRDFTELPHSPLKFHTYAVH
CCCFSPSGHILASCSTDGTTVLWNTENGQMLAVMEQPSGSPVRVCQFSPDSTCLASGA
ADGTVVLWNAQSYKLYRCGSVKDGSLAACAFSPNGSFFVTGSSCGDLTVWDDKMRCLH
SEKAHDLGITCCDFSSQPVSDGEQGLQFFRLASCGQDCQVKIWIVSFTHILARRTEHQ
LKQFTEDWSEEVVSTWLCAQDLKDLVGIFKMNNIDGKELLNLTKESLADDLKIESLGL
RSKVLRKIEELRTKVKSLSSGIPDEFICPITRELMKDPVIASDGYSYEKEAMENWISK
KKRTSPMTNLVLPSAVLTPNRTLKMAINRWLETHQK
```

FIG. 20A

```
gaattcggctcgaggccggcgcccgccccgccagcctcacctgcgcggcacgtgacccgcac
cgcccgtgggcaccttgaaggcggatcccgcgcgccccgctcctgcaggctgttttcttc
aaataaagaacatggtgaaactgattcacacattagctgatcatggtgacgatgtcaactgc
tgtgccttctccttttcctcttggctacttgctccttggacaaaacaattcgctgtactc
gttacgtgactttactgaactgccacattctccattgaagtttcatacctatgctgtccact
gctgctgtttctcccttcaggacatattttggcatcgtgttcaacagatggtaccactgtc
ctatggaatactgaaaatggacagatgctggcagtgatggaacagctagtggcagccctgt
gagggtttgccagttttccccagactccacgtgtttggcatcaggggcagctgatggaactg
tggttttgtggaatgcacagtcatacaaattatatagatgtggtagtgttaaagatggctcc
ttggcggcatgtgcattttctcctaatggaagcttctttgtcactggctcctcatgtggtga
tttaacagtgtgggatgataaaatgaggtgtctgcatagtgaaaagcacatgatcttggaa
ttacctgctgcgattttcttcacagccagtttctgatggagaacaaggtcttcagtttttt
cgactggcatcatgtggtcaggattgccaagtcaaaatttggattgtttcttttacccatat
cttaggttttgaattaaaatataaaagtacactgagtgggcactgtgctcctgttctggctt
gtgcttttcccatgatgggcagatgctagtctcagggtcagtggataagtctgtcatagta
tatgatactaatactgagaatatacttcacacattgactcagcacaccaggtatgtcacaac
ttgtgcttttgcacctaatacccttttacttgctactggttcaatggacaaaacagtgaaca
tctggcaatttgacctggaaacactttgccaagcaaggcgcacagaacatcagctgaagcaa
tttaccgaagattggtcagaggaggatgtctcaacatggctttgtgcacaagatttaaaaga
tcttgttggtattttcaagatgaataacattgatggaaaagaactgttgaatcttacaaaag
aaagtctggctgatgatttgaaaattggctggagtcctctggcatggtcatgcctcactgca
gcttcaacctcctgggctcaagtgatcctcctacctcggcctcaatctctaggactgcgtag
taaagtgctgaggaaaattgaagagctcaggaccaaggttaaatccctttcttcaggaattc
ctgatgaatttatatgtccaataactagagaacttatgaaagatccggtcatcgcatcagat
ggctattcatatgaaaggaagcaatggaaaattggatcagcaaaaagaaacgtacaagtcc
catgacaaatcttgttcttccttcagcggtacttacaccaaataggactctgaaaatggcca
tcaatagatggctggagacacaccaaaagtaaaattgttgatattgtattatttatattttc
agtgatctcatttgaatgatttataggtaaatactaatcagacattattaaaagcaaaacag
gaaaaggtaaacttcttaaatttagttacctataaaaattgtcaattttcattcttaaaa
aacacatggacttactataaaagccttttgtactagtgaaagaatcttcagctatataga
aataaagttatcctttaaaaaaaaaaaaaaaaaaaaagggcggccgc
```

FIG. 20B

```
MVKLIHTLADHGDDVNCCAFSFSLLATCSLDKTIRLYSLRDFTELPHSPLKFHTYAV
HCCCFSPSGHILASCSTDGTTVLWNTENGQMLAVMEQPSGSPVRVCQFSPDSTCLAS
GAADGTVVLWNAQSYKLYRCGSVKDGSLAACAFSPNGSFFVTGSSCGDLTVWDDKMR
CLHSEKAHDLGITCCDFSSQPVSDGEQGLQFFRLASCGQDCQVKIWIVSFTHILGFE
LKYKSTLSGHCAPVLACAFSHDGQMLVSGSVDKSVIVYDTNTENILHTLTQHTRYVT
TCAFAPNTLLLATGSMDKTVNIWQFDLETLCQARRTEHQLKQFTEDWSEEDVSTWLC
AQDLKDLVGIFKMNNIDGKELLNLTKESLADDLKIGWSPLAWSCLTAASTSWAQVIL
LPRPQSLGLRSKVLRKIEELRTKVKSLSSGIPDEFICPITRELMKDPVIASDGYSYE
KEAMENWISKKKRTSPMTNLVLPSAVLTPNRTLKMAINRWLETHQK
```

FIG. 21 h (LIYFWVMA) hydrophobic
l (LIVAM) aliphatic
s (GASNSTCP) small
p (STNREQHD) polar
(-) (D,E) negatively charged.

| Ubox | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 5 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| RET16 Ubox | E | F | I | C | P | I | T | R | E | L | M | K | D | P | V | I | A | S | D | G | Y | S | | Y | E | K | E | A | M | E | N | W | I | S | K | K | K | R | T | S | P | M | T | N | | L | V | L | P | S | A | V |
| PRP19 | M | L | C | A | I | S | G | K | V | P | R | R | P | V | L | S | P | K | S | R | T | I | F | E | K | S | L | L | E | Q | Y | V | | K | D | T | G | N | D | P | I | T | N | E | P | L | S | I | E | E | I | V |
| consensus | h | | s | | l | | | | | p | h | h | | (-) | | s | h | | | | | s | | | | h | p | p | | | l | | p | h | | | | | s | P | | s | | | | | | | | | | | |

SEQUENCE LISTING

<160> NUMBER OF SEQ ID NOS: 25

<210> SEQ ID NO 1
<211> LENGTH: 1818
<212> TYPE: DNA
<213> ORGANISM: HUMAN

<400> SEQUENCE: 1
gcctgttccc tctgctctgg gtctccgccg gcgcccgccc cgccagcctc acctgcgcgg    60

```
cacgtgaccc gcaccgcccg tgggcacctt gaaggcggat cccgcgcgcc ccgctcctg      120 caggctgttt ttcttcaaat aaagaacatg gtgaaactga ttcacacatt agctgatcat     180
ggtgacgatg tcaactgctg tgccttctcc ttttccctct tggctacttg ctccttggac     240
aaaacaattc gcctgtactc gttacgtgac tttactgaac tgccacattc tccattgaag     300
tttcatacct atgctgtcca ctgctgctgt ttctcccctt caggacatat tttggcatcg     360
tgttcaacag atggtaccac tgtcctatgg aatactgaaa atggacagat gctggcagtg     420
atggaacagc ctagtggcag ccctgtgagg gtttgccagt tttccccaga ctccacgtgt     480
ttggcatcag gggcagctga tggaactgtg gttttgtgga atgcacagtc atacaaatta     540
tatagatgtg gtagtgttaa agatggctcc ttggcggcat gtgcattttc tcctaatgga     600
agcttctttg tcactggctc ctcatgtggt gatttaacag tgtgggatga taaaatgagg     660
tgtctgcata gtgaaaaagc acatgatctt ggaattacct gctgcgattt ttcttcacag     720
ccagtttctg atggagaaca aggtcttcag ttttttcgac tggcatcatg tggtcaggat     780
tgccaagtca aaatttggat tgtttctttt acccatatct taggttttga attaaaatat     840
aaaagtacac tgagtgggca ctgtgctcct gttctggctt gtgctttttc ccatgatggg     900
cagatgctag tctcagggtc agtggataag tctgtcatag tatatgatac taatactgag     960
aatatacttc acacattgac tcagcacacc aggtatgtca caacttgtgc ttttgcacct    1020
aatacccttt tacttgctac tggttcaatg gacaaaacag tgaacatctg gcaatttgac    1080
ctggaaacac tttgccaagc aaggcgcaca gaacatcagc tgaagcaatt taccgaagat    1140
tggtcagagg aggatgtctc aacatggctt tgtgcacaag atttaaaaga tcttgttggt    1200
attttcaaga tgaataacat tgatggaaaa gaactgttga atcttacaaa agaaagtctg    1260
gctgatgatt tgaaaattga atctctagga ctgcgtagta aagtgctgag gaaaattgaa    1320
gagctcagga ccaaggttaa atccctttct tcaggaattc ctgatgaatt tatatgtcca    1380
ataactagag aacttatgaa agatccggtc atcgcatcag atggctattc atatgaaaag    1440
gaagcaatgg aaaattggat cagcaaaaag aaacgtacaa gtcccatgac aaatcttgtt    1500
cttccttcag cggtacttac accaaatagg actctgaaaa tggccatcaa tagatggctg    1560
gagacacacc aaaagtaaaa ttgttgatat tgtattattt atattttcag tgatctcatt    1620
tgaatgattt ataggtaaat actaatcaga cattattaaa agcaaaacag gaaaaaggta    1680
aacttcttaa atttagttac ctataaaaat tgtcaatttt cattctttaa aaaacacatg    1740
gacttactat aaaagccтттт ttgtactagt gaaaagaatc ttcagctata tagaaataaa    1800
gttatacttt aaaaaaaa                                                 1818
```

<210> SEQ ID NO 2
<211> LENGTH: 476
<212> TYPE: PRT
<213> ORGANISM: HUMAN

<400> SEQUENCE: 2

```
Met Val Lys Leu Ile His Thr Leu Ala Asp His Gly Asp Asp Val Asn
 1               5                  10                  15

Cys Cys Ala Phe Ser Phe Ser Leu Leu Ala Thr Cys Ser Leu Asp Lys
            20                  25                  30

Thr Ile Arg Leu Tyr Ser Leu Arg Asp Phe Thr Glu Leu Pro His Ser
        35                  40                  45

Pro Leu Lys Phe His Thr Tyr Ala Val His Cys Cys Phe Ser Pro
        50                  55                  60
```

```
Ser Gly His Ile Leu Ala Ser Cys Ser Thr Asp Gly Thr Thr Val Leu
 65                  70                  75                  80

Trp Asn Thr Glu Asn Gly Gln Met Leu Ala Val Met Glu Gln Pro Ser
             85                  90                  95

Gly Ser Pro Val Arg Val Cys Gln Phe Ser Pro Asp Ser Thr Cys Leu
            100                 105                 110

Ala Ser Gly Ala Ala Asp Gly Thr Val Val Leu Trp Asn Ala Gln Ser
        115                 120                 125

Tyr Lys Leu Tyr Arg Cys Gly Ser Val Lys Asp Gly Ser Leu Ala Ala
    130                 135                 140

Cys Ala Phe Ser Pro Asn Gly Ser Phe Val Thr Gly Ser Ser Cys
145                 150                 155                 160

Gly Asp Leu Thr Val Trp Asp Asp Lys Met Arg Cys Leu His Ser Glu
                165                 170                 175

Lys Ala His Asp Leu Gly Ile Thr Cys Cys Asp Phe Ser Ser Gln Pro
            180                 185                 190

Val Ser Asp Gly Glu Gln Gly Leu Gln Phe Phe Arg Leu Ala Ser Cys
        195                 200                 205

Gly Gln Asp Cys Gln Val Lys Ile Trp Ile Val Ser Phe Thr His Ile
    210                 215                 220

Leu Gly Phe Glu Leu Lys Tyr Lys Ser Thr Leu Ser Gly His Cys Ala
225                 230                 235                 240

Pro Val Leu Ala Cys Ala Phe Ser His Asp Gly Gln Met Leu Val Ser
                245                 250                 255

Gly Ser Val Asp Lys Ser Val Ile Val Tyr Asp Thr Asn Thr Glu Asn
            260                 265                 270

Ile Leu His Thr Leu Thr Gln His Thr Arg Tyr Val Thr Thr Cys Ala
        275                 280                 285

Phe Ala Pro Asn Thr Leu Leu Leu Ala Thr Gly Ser Met Asp Lys Thr
    290                 295                 300

Val Asn Ile Trp Gln Phe Asp Leu Glu Thr Leu Cys Gln Ala Arg Arg
305                 310                 315                 320

Thr Glu His Gln Leu Lys Gln Phe Thr Glu Asp Trp Ser Glu Glu Asp
                325                 330                 335

Val Ser Thr Trp Leu Cys Ala Gln Asp Leu Lys Asp Leu Val Gly Ile
            340                 345                 350

Phe Lys Met Asn Asn Ile Asp Gly Lys Glu Leu Leu Asn Leu Thr Lys
        355                 360                 365

Glu Ser Leu Ala Asp Asp Leu Lys Ile Glu Ser Leu Gly Leu Arg Ser
    370                 375                 380

Lys Val Leu Arg Lys Ile Glu Glu Leu Arg Thr Lys Val Lys Ser Leu
385                 390                 395                 400

Ser Ser Gly Ile Pro Asp Glu Phe Ile Cys Pro Ile Thr Arg Glu Leu
                405                 410                 415

Met Lys Asp Pro Val Ile Ala Ser Asp Gly Tyr Ser Tyr Glu Lys Glu
            420                 425                 430

Ala Met Glu Asn Trp Ile Ser Lys Lys Arg Thr Ser Pro Met Thr
        435                 440                 445

Asn Leu Val Leu Pro Ser Ala Val Leu Thr Pro Asn Arg Thr Leu Lys
    450                 455                 460

Met Ala Ile Asn Arg Trp Leu Glu Thr His Gln Lys
465                 470                 475
```

<210> SEQ ID NO 3
<211> LENGTH: 1553
<212> TYPE: DNA
<213> ORGANISM: HUMAN

<400> SEQUENCE: 3

```
gaattcggct tcacctgcg cggcacgtga cccgcaccgc ccgtgggcac cttgaaggcg      60
gatcccgcgc gccccgctc ctgcaggctg tttttcttca aataaagaac atggtgaaac    120
tgattcacac attagctgat catggtgacg atgtcaactg ctgtgccttc tccttttccc    180
tcttggctac ttgctccttg acaaaacaa ttcgcctgta ctcgttacgt gactttactg    240
aactgccaca ttctccattg aagtttcata cctatgctgt ccactgctgc tgtttctccc    300
cttcaggaca tattttggca tcgtgttcaa cagatggtac cactgtccta tggaatactg    360
aaaatggaca gatgctggca gtgatggaac agcctagtgg cagccctgtg agggtttgcc    420
agttttcccc agactccacg tgtttggcat caggggcagc tgatggaact gtggttttgt    480
ggaatgcaca gtcatacaaa ttatatagat gtggtagtgt taagatggc tccttggcgg    540
catgtgcatt ttctcctaat ggaagcttct ttgtcactgg ctcctcatgt ggtgatttaa    600
cagtgtggga tgataaaatg aggtgtctgc atagtgaaaa agcacatgat cttggaatta    660
cctgctgcga ttttttcttca cagccagttt ctgatggaga acaaggtctt cagtttttc    720
gactggcatc atgtggtcag gattgccaag tcaaaatttg gattgtttct tttacccata    780
tcttaggttt tgaattaaaa tataaaagta cactgagtgg gcactgtgct cctgttctgg    840
cttgtgcttt ttcccgtgat gggcagatgc tagtctcagg gtcagtggat aagtctgtca    900
tagtatatga tactaatact gagaatatac ttcacacatt gactcagcac accaggtatg    960
tcacaacttg tgcttttgca cctaataccc ttttacttgc tactggttca atggacaaaa   1020
cagtgaacat ctggcaattt gacctggaaa cactttgcca agcaaggcgc acagaacatc   1080
agctgaagca atttaccgaa gattggtcag aggaggatgt ctcaacatgg ctttgtgcac   1140
aagatttaaa agatcttgtt ggtatttttca agatgaataa cattgatgga aagaactgt   1200
tgaatcttac aaaagaaagt ctggctgatg atttgaaaat tgaatctcta ggactgcgta   1260
gtaaagtgct gaggaaaatt gaagagctca ggaccaaggt taaatccctt tcttcaggaa   1320
ttcctgatga atttatatgt ccaataacta gagaacttat gaaagatccg gtcatcgcat   1380
cagatggcta ttcatatgaa aaggaagcaa tggaaaattg gatcagcaaa agaaacgta   1440
caagtcccat gacaaatctt gttcttcctt cagcggtact tacaccaaat ggactctga   1500
aaatggccat caatagatgg ctggagacac accaaaagta aaaagccgaa ttc          1553
```

<210> SEQ ID NO 4
<211> LENGTH: 512
<212> TYPE: PRT
<213> ORGANISM: HUMAN

<400> SEQUENCE: 4

```
Ile Arg Leu Ser Pro Ala Arg His Val Thr Arg Thr Ala Arg Gly His
 1               5                  10                  15

Leu Glu Gly Gly Ser Arg Ala Pro Pro Leu Leu Gln Ala Val Phe Leu
            20                  25                  30

Gln Ile Lys Asn Met Val Lys Leu Ile His Thr Leu Ala Asp His Gly
        35                  40                  45

Asp Asp Val Asn Cys Cys Ala Phe Ser Phe Ser Leu Leu Ala Thr Cys
    50                  55                  60
```

-continued

```
Ser Leu Asp Lys Thr Ile Arg Leu Tyr Ser Leu Arg Asp Phe Thr Glu
 65                  70                  75                  80

Leu Pro His Ser Pro Leu Lys Phe His Thr Tyr Ala Val His Cys Cys
                 85                  90                  95

Cys Phe Ser Pro Ser Gly His Ile Leu Ala Ser Cys Ser Thr Asp Gly
            100                 105                 110

Thr Thr Val Leu Trp Asn Thr Glu Asn Gly Gln Met Leu Ala Val Met
        115                 120                 125

Glu Gln Pro Ser Gly Ser Pro Val Arg Val Cys Gln Phe Ser Pro Asp
    130                 135                 140

Ser Thr Cys Leu Ala Ser Gly Ala Ala Asp Gly Thr Val Val Leu Trp
145                 150                 155                 160

Asn Ala Gln Ser Tyr Lys Leu Tyr Arg Cys Gly Ser Val Lys Asp Gly
                165                 170                 175

Ser Leu Ala Ala Cys Ala Phe Ser Pro Asn Gly Ser Phe Phe Val Thr
            180                 185                 190

Gly Ser Ser Cys Gly Asp Leu Thr Val Trp Asp Asp Lys Met Arg Cys
        195                 200                 205

Leu His Ser Glu Lys Ala His Asp Leu Gly Ile Thr Cys Cys Asp Phe
    210                 215                 220

Ser Ser Gln Pro Val Ser Asp Gly Glu Gln Gly Leu Gln Phe Phe Arg
225                 230                 235                 240

Leu Ala Ser Cys Gly Gln Asp Cys Gln Val Lys Ile Trp Ile Val Ser
                245                 250                 255

Phe Thr His Ile Leu Gly Phe Glu Leu Lys Tyr Lys Ser Thr Leu Ser
            260                 265                 270

Gly His Cys Ala Pro Val Leu Ala Cys Ala Phe Ser Arg Asp Gly Gln
        275                 280                 285

Met Leu Val Ser Gly Ser Val Asp Lys Ser Val Ile Val Tyr Asp Thr
    290                 295                 300

Asn Thr Glu Asn Ile Leu His Thr Leu Thr Gln His Thr Arg Tyr Val
305                 310                 315                 320

Thr Thr Cys Ala Phe Ala Pro Asn Thr Leu Leu Leu Ala Thr Gly Ser
                325                 330                 335

Met Asp Lys Thr Val Asn Ile Trp Gln Phe Asp Leu Glu Thr Leu Cys
            340                 345                 350

Gln Ala Arg Arg Thr Glu His Gln Leu Lys Gln Phe Thr Glu Asp Trp
        355                 360                 365

Ser Glu Glu Asp Val Ser Thr Trp Leu Cys Ala Gln Asp Leu Lys Asp
    370                 375                 380

Leu Val Gly Ile Phe Lys Met Asn Asn Ile Asp Gly Lys Glu Leu Leu
385                 390                 395                 400

Asn Leu Thr Lys Glu Ser Leu Ala Asp Asp Leu Lys Ile Glu Ser Leu
                405                 410                 415

Gly Leu Arg Ser Lys Val Leu Arg Lys Ile Glu Glu Leu Arg Thr Lys
            420                 425                 430

Val Lys Ser Leu Ser Ser Gly Ile Pro Asp Glu Phe Ile Cys Pro Ile
        435                 440                 445

Thr Arg Glu Leu Met Lys Asp Pro Val Ile Ala Ser Asp Gly Tyr Ser
    450                 455                 460

Tyr Glu Lys Glu Ala Met Glu Asn Trp Ile Ser Lys Lys Lys Arg Thr
465                 470                 475                 480
```

```
Ser Pro Met Thr Asn Leu Val Leu Pro Ser Ala Val Leu Thr Pro Asn
            485                 490                 495

Arg Thr Leu Lys Met Ala Ile Asn Arg Trp Leu Glu Thr His Gln Lys
        500                 505                 510

<210> SEQ ID NO 5
<211> LENGTH: 630
<212> TYPE: DNA
<213> ORGANISM: HUMAN
<220> FEATURE:
<223> OTHER INFORMATION: 630 bp partial nucleic acid sequence of human
      RET16 cDNA

<400> SEQUENCE: 5
acactgagtg ggcactgtgc tcctgttctg gcttgtgctt tttcccatga tgggcagatg    60
ctagtctcag ggtcagtgga taagtctgtc atagtatatg atactaatac tgagaatata   120
cttcacacat tgactcagca caccaggtat gtcacaactt gtgcttttgc acctaatacc   180
cttttacttg ctactggttc aatggacaaa acagtgaaca tctggcaatt tgacctggaa   240
acactttgcc aagcaaggcg cacagaacat cagctgaagc aatttaccga agattggtca   300
gaggaggatg tctcaacatg gctttgtgca caagatttaa aagatcttgt tggtattttc   360
aagatgaata acattgatgg aaaagaactg ttgaatctta caaaagaaag tctggctgat   420
gatttgaaaa ttgaatctct aggactgcgt agtaaagtgc tgaggaaaat tgaagagctc   480
aggaccaagg ttaaatccct ttcttcagga attcctgatg aatttatatg tccaataact   540
agagaactta tgaaagatcc ggtcatcgca tcagatggct attcatatga aaaggaagca   600
atggaaaatt ggatcagcaa aaagaaacgt                                    630

<210> SEQ ID NO 6
<211> LENGTH: 1901
<212> TYPE: DNA
<213> ORGANISM: MOUSE

<400> SEQUENCE: 6
ttactttgtg tgaggaacat ggtgaggttg attcacacgc tggctgatca cggggatgac    60
gtcagctgct gcgccttctc ggctgccctc ctggccacct gctccttgga caagaccatc   120
cgtctgtact ccctaagtga ctttgttgaa ctgccgtact ccccgctgaa gttccacacc   180
tatgctgtcc actgctgctg tttctcaccc tcaggacacg ttttagcatc gtgctcgaca   240
gacgggacca cggtgctgtg gagctcgcac agcggacaca ccctgaccgt gttggagcag   300
ccgggtggca gccctgtgcg cgtctgttgc ttttccccag actctgccta cctagcgtca   360
ggggctgccg atggatccat tgctttgtgg aatgcacaga catacaaact atataggtgt   420
ggtagtgtca aggatagctc attggtggcc tgtgcgtttt ctcccgatgg aggcctcttt   480
gtcactggct cctcgggcgg ggacttgaca gtgtgggatg acagaatgag gtgtctacac   540
agcgagaagg cgcacgatct cgggatcacc tgctgcagct tttcctcaca gcctctctct   600
ggcggagaag gcctccagtc ttaccagttg gcgtcatgtg gtcaagactg tgaaatcaaa   660
ctctgggctg ttactattac ccgtgtctta ggctttgaat aaaatataaa agcacacta    720 agtgggcact cgcgcccctgt tctggcctgt gcttttttcac atgatggaaa gatgcttgca   780 tcgggtcag tggataaatc tgtcatcata catggtatcg gccctcagag tgtgctacac   840
acgctgactc agcataccag gtatgttacg acttgtgcgt ttgcacccaa cactctctta   900
cttgctactg gttcaatgga caagacagtg aacatttggc agtttgacct ggaaacacct   960
```

-continued

```
tgccaagcag gaagcatgaa cgacccgctg aaacatttca ctgaagaatg gtcagaggag    1020
gatgtctccg tgtggcttcg tgctcaaggc ttggaagacc tcgtcggtat tttcagggca    1080
aacaacatcg atgggaaaga actattgcat ctcacaaagg aaagtctggc tggtgatttg    1140
aaaatcgaat ctctagggct gcgcagcaaa gtcctgagga gtattgaaga gctcagggcc    1200
aagatggatt ccctctcttc cggaatccct gacgagttca tctgcccaat aaccagagaa    1260
ctcatgaagg accccgtcat cgcatcagat ggctactcct acgagagaga agcaatggaa    1320
agctggatcc acaagaagaa gcgtacgagc cccatgacaa atttggctct cccttcactg    1380
gtactgaccc caaacaggac actgaagatg gccatcaacc gatggctgga gacgcacgag    1440
aagtgaacgc gttcacaggc atcggatcca ctttcagtga tgccctgcaa atgattcaaa    1500
atgctaagca gccatcacga aagcaaaata aaggaaaag acaaatgttc aattcagtta    1560
cttttaaaaa ctgtaaatta tgagcagggc agtggtggtg cccaccttta atcccagcac    1620
tcaggaggca gagacaggtg gatctccagg atcaggagtt ccaggacagc ccagtttata    1680
gggcaagtct caggacggcc aaggctacac agagaaaccc tgtctcaaaa aacccaaaac    1740
ccaaaaaaaa aaaaaaaaaa agtcaattat ctttaaaaca cagatttata tatctattgt    1800
cattgctatt tctgtaaagg tgaaaatatt tttttttttg caataatgag aaactatgta    1860
gaaataaaac ttcactatga ctttaaaaaa aaaaaaaaa a                         1901
```

<210> SEQ ID NO 7
<211> LENGTH: 475
<212> TYPE: PRT
<213> ORGANISM: MOUSE

<400> SEQUENCE: 7

```
Met Val Arg Leu Ile His Thr Leu Ala Asp His Gly Asp Asp Val Ser
 1               5                  10                  15

Cys Cys Ala Phe Ser Ala Ala Leu Leu Ala Thr Cys Ser Leu Asp Lys
             20                  25                  30

Thr Ile Arg Leu Tyr Ser Leu Ser Asp Phe Val Glu Leu Pro Tyr Ser
         35                  40                  45

Pro Leu Lys Phe His Thr Tyr Ala Val His Cys Cys Phe Ser Pro
     50                  55                  60

Ser Gly His Val Leu Ala Ser Cys Ser Thr Asp Gly Thr Thr Val Leu
 65                  70                  75                  80

Trp Ser Ser His Ser Gly His Thr Leu Thr Val Leu Glu Gln Pro Gly
                 85                  90                  95

Gly Ser Pro Val Arg Val Cys Cys Phe Ser Pro Asp Ser Ala Tyr Leu
            100                 105                 110

Ala Ser Gly Ala Ala Asp Gly Ser Ile Ala Leu Trp Asn Ala Gln Thr
        115                 120                 125

Tyr Lys Leu Tyr Arg Cys Gly Ser Val Lys Asp Ser Ser Leu Val Ala
    130                 135                 140

Cys Ala Phe Ser Pro Asp Gly Leu Phe Val Thr Gly Ser Ser Gly
145                 150                 155                 160

Gly Asp Leu Thr Val Trp Asp Asp Arg Met Arg Cys Leu His Ser Glu
                165                 170                 175

Lys Ala His Asp Leu Gly Ile Thr Cys Cys Ser Phe Ser Ser Gln Pro
            180                 185                 190

Leu Ser Gly Gly Glu Gly Leu Gln Ser Tyr Gln Leu Ala Ser Cys Gly
        195                 200                 205
```

-continued

```
Gln Asp Cys Glu Ile Lys Leu Trp Ala Val Thr Ile Thr Arg Val Leu
    210                 215                 220
Gly Phe Glu Leu Lys Tyr Lys Ser Thr Leu Ser Gly His Cys Ala Pro
225                 230                 235                 240
Val Leu Ala Cys Ala Phe Ser His Asp Gly Lys Met Leu Ala Ser Gly
                245                 250                 255
Ser Val Asp Lys Ser Val Ile Ile His Gly Ile Gly Pro Gln Ser Val
            260                 265                 270
Leu His Thr Leu Thr Gln His Thr Arg Tyr Val Thr Thr Cys Ala Phe
        275                 280                 285
Ala Pro Asn Thr Leu Leu Ala Thr Gly Ser Met Asp Lys Thr Val
    290                 295                 300
Asn Ile Trp Gln Phe Asp Leu Glu Thr Pro Cys Gln Ala Gly Ser Met
305                 310                 315                 320
Asn Asp Pro Leu Lys His Phe Thr Glu Glu Trp Ser Glu Glu Asp Val
                325                 330                 335
Ser Val Trp Leu Arg Ala Gln Gly Leu Glu Asp Leu Val Gly Ile Phe
            340                 345                 350
Arg Ala Asn Asn Ile Asp Gly Lys Glu Leu Leu His Leu Thr Lys Glu
        355                 360                 365
Ser Leu Ala Gly Asp Leu Lys Ile Glu Ser Leu Gly Leu Arg Ser Lys
    370                 375                 380
Val Leu Arg Ser Ile Glu Glu Leu Arg Ala Lys Met Asp Ser Leu Ser
385                 390                 395                 400
Ser Gly Ile Pro Asp Glu Phe Ile Cys Pro Ile Thr Arg Glu Leu Met
                405                 410                 415
Lys Asp Pro Val Ile Ala Ser Asp Gly Tyr Ser Tyr Glu Arg Glu Ala
            420                 425                 430
Met Glu Ser Trp Ile His Lys Lys Lys Arg Thr Ser Pro Met Thr Asn
        435                 440                 445
Leu Ala Leu Pro Ser Leu Val Leu Thr Pro Asn Arg Thr Leu Lys Met
    450                 455                 460
Ala Ile Asn Arg Trp Leu Glu Thr His Glu Lys
465                 470                 475
```

<210> SEQ ID NO 8
<211> LENGTH: 520
<212> TYPE: DNA
<213> ORGANISM: RAT

<400> SEQUENCE: 8

```
tgacgagttc atctgcccaa taaccaggga acttatgaag gaccccgtca tcgcatcaga     60
tggctactcc tacgagagag aagcaatgga gagttggatc acaagaaga agcgcacgag    120
ccccatgaca aacttggctc ttccttcact ggtactgacc ccaaacagga ctctgaaaat    180
ggccatcaat cgatggctag agacgcatca gaagtgaacc tgcccacagg catcgggtac    240
actgtcagtg atgcccttca gatgattcaa aatgctaagc agccattaca gaagcaaata    300
aaagggaagg acagacgtta aatccagtta ctttttaaaaa ctgtaaactg taagcaggta    360
agtggtggcg cacaccttta atcccagcac tcaggaggca gaggcaggtg ggtctccatg    420
aattccaggc cagcctggtc tatagggcga gttccaggac ggcaaggcta cacagagaaa    480
ccctgtctca aaaacctaaa agcaaaaaaa aaaaaaaaaa                          520
```

<210> SEQ ID NO 9

```
<211> LENGTH: 71
<212> TYPE: PRT
<213> ORGANISM: RAT

<400> SEQUENCE: 9

Asp Glu Phe Ile Cys Pro Ile Thr Arg Glu Leu Met Lys Asp Pro Val
 1               5                  10                  15

Ile Ala Ser Asp Gly Tyr Ser Tyr Glu Arg Glu Ala Met Glu Ser Trp
            20                  25                  30

Ile His Lys Lys Lys Arg Thr Ser Pro Met Thr Asn Leu Ala Leu Pro
        35                  40                  45

Ser Leu Val Leu Thr Pro Asn Arg Thr Leu Lys Met Ala Ile Asn Arg
    50                  55                  60

Trp Leu Glu Thr His Gln Lys
 65                  70

<210> SEQ ID NO 10
<211> LENGTH: 1356
<212> TYPE: PRT
<213> ORGANISM: Podospora anserina
<220> FEATURE:
<223> OTHER INFORMATION: beta transducin-like protein encoded by the
      het-e-1 gene

<400> SEQUENCE: 10

Met Arg Leu Leu Glu Arg Asp Asp Ala Gly Glu Ile Arg Pro Thr Lys
 1               5                  10                  15

Asp Leu Pro Ser Gly Lys Ile Pro Pro Tyr Ala Ile Leu Ser His Thr
            20                  25                  30

Trp Gly Pro Asp Glu Glu Val Ser Tyr Lys Asp Leu Lys Asp Gly
        35                  40                  45

Arg Ala Val Ser Lys Leu Gly Tyr Asn Lys Ile Arg Phe Cys Ala Asp
    50                  55                  60

Gln Ala Trp Arg Asp Gly Arg Lys Phe Phe Trp Val Asp Thr Cys Cys
 65                  70                  75                  80

Ile Asp Lys Ser Asn Ser Thr Glu Leu Gln Glu Ala Ile Asn Ser Met
                 85                  90                  95

Phe Arg Trp Tyr Arg Asp Ala Ala Lys Cys Tyr Val Tyr Leu Thr Asp
            100                 105                 110

Val Ser Thr Asp Lys Arg Asp Ala Asp Gly Asp Pro Ser Trp Lys Trp
        115                 120                 125

Ala Phe Gln Lys Cys Lys Trp Phe Thr Arg Gly Trp Thr Leu Gln Glu
    130                 135                 140

Leu Ile Ala Pro Thr Ser Val Glu Phe Phe Ser Arg Glu Lys Ala Arg
145                 150                 155                 160

Ile Gly Asp Arg Asn Ser Leu Glu Arg Met Ile His Asp Val Thr Gly
                165                 170                 175

Ile Pro Leu Glu Ala Leu Arg Gly Ser Pro Leu Ser Asp Phe Ser Val
            180                 185                 190

His Asp Arg Met Ala Trp Met Lys Gln Arg Asn Thr Thr Arg Glu Glu
        195                 200                 205

Asp Met Ala Tyr Ser Leu Phe Gly Ile Phe Asp Val His Leu Pro Leu
    210                 215                 220

Ile Tyr Gly Glu Gly Lys Glu Lys Ala Leu Glu Arg Leu Arg Glu Lys
225                 230                 235                 240

Ile Gly Lys Asp Asp Gly Cys Leu Ala Asp Leu Arg Val Thr Asp Pro
                245                 250                 255
```

```
Arg His Asp Lys Lys Arg Ile Glu Ala Ala Lys Gly Gly Leu Leu Lys
            260                 265                 270

Asp Ser Tyr Cys Trp Val Leu Ser Asn Val Gln Phe Gln Gln Trp His
        275                 280                 285

Asp Gly Asp Asp Gln Arg Leu Leu Trp Ile Asn Gly Asp Pro Gly Lys
    290                 295                 300

Gly Lys Thr Met Leu Leu Cys Gly Ile Ile Asp Glu Leu Lys Lys Ser
305                 310                 315                 320

Thr Pro Pro Gly Leu Leu Ser Phe Phe Phe Cys Gln Ala Thr Asp Ser
                325                 330                 335

Arg Ile Asn Asn Ala Thr Ala Val Leu Arg Gly Leu Ile Tyr Leu Leu
            340                 345                 350

Val Ser Gln Gln Pro Ala Leu Ile Ser His Val Arg Arg Pro Tyr Asp
        355                 360                 365

His Ala Gly Lys Lys Met Phe Glu Gly Pro Asn Val Trp Ile Val Leu
    370                 375                 380

Cys Glu Ile Phe Thr Ser Ile Leu Gln Asp Pro Gly Leu Arg Met Thr
385                 390                 395                 400

Tyr Leu Ile Ile Asp Ala Leu Asp Glu Cys Val Thr Asp Leu Pro Gln
                405                 410                 415

Leu Leu Glu Leu Ile Thr Arg Thr Ser Cys Thr Ser Ser Pro Ile Lys
            420                 425                 430

Trp Ile Val Ser Ser Arg Asn Trp Pro Asp Ile Glu Glu Gln Leu Glu
        435                 440                 445

Thr Ala Thr Gln Lys Ala Arg Leu Ser Leu Glu Leu Asn Ala Glu Ser
    450                 455                 460

Ile Ser Thr Ala Val Asn Ala Phe Ile Gln Asn Arg Ile Asp Gln Leu
465                 470                 475                 480

Ala Pro Lys Thr Lys His Asp Ala Asn Met Ile Gly Lys Ile Arg Asp
                485                 490                 495

Tyr Leu His Ser His Ala Asn Gly Thr Phe Leu Trp Val Ala Leu Val
            500                 505                 510

Cys Gln Ala Leu Ala Asp Pro Lys Val Lys Lys Arg His Ile Leu Ala
        515                 520                 525

Lys Leu Gln Thr Phe Pro Arg Gly Leu Asp Ser Leu Tyr Ala Arg Met
    530                 535                 540

Leu Glu Gln Ile Gly His Ser Glu Asp Ala Glu Leu Cys Lys Gln Ile
545                 550                 555                 560

Leu Ala Val Ala Ala Ala Val Arg Arg Pro Ile Ser Leu Asp Glu Leu
                565                 570                 575

Ala Ser Leu Val Glu Met Pro Asp Asp Val Ser Asp Pro Glu Ser
            580                 585                 590

Leu Glu Glu Ile Val Lys Leu Cys Gly Ser Phe Leu Ile Ile Arg Glu
        595                 600                 605

Arg Thr Val Tyr Phe Val His Gln Ser Ala Lys Asp Phe Leu Leu Gly
    610                 615                 620

Thr Ala Ser Asp Lys Ala Ser Asn Lys Ala Ser Gln Glu Ala Phe Glu
625                 630                 635                 640

Leu Val Phe Pro Thr Gly Ile Glu Asp Val Ser Tyr Ile Ile Phe Trp
                645                 650                 655

Arg Ser Leu Asn Val Met Ser Gln Lys Leu Arg Arg Asp Ile Tyr Cys
            660                 665                 670
```

-continued

Leu Asn Ala Pro Gly Phe Leu Ile Asp Asn Val Arg Val Pro Asp Pro
            675                 680                 685

Asp Pro Leu Ala Thr Val Arg Tyr Ser Cys Ile Tyr Trp Ile Asp His
        690                 695                 700

Leu Arg Asp Leu Val Ser Ser Thr Ser Ser Lys Trp Val His Leu Leu
705                 710                 715                 720

Gln Asp Asp Gly Asp Ile His Arg Phe Leu Thr Thr Lys Tyr Leu Tyr
                725                 730                 735

Trp Leu Glu Ala Leu Ser Leu Leu Arg Ala Leu Pro Glu Gly Ile Asn
            740                 745                 750

Ala Ile Arg Gln Leu Glu Ser Leu Leu Gly His Thr Ile Arg Gly Arg
        755                 760                 765

Leu Ile Ala Ile Val Arg Asp Gly Tyr Arg Phe Ala Leu Ser Tyr Arg
770                 775                 780

Met Ile Ile Glu Lys Ala Pro Leu Gln Ala Tyr Thr Ser Ala Leu Val
785                 790                 795                 800

Phe Ala Pro Thr Asp Ser Met Ile Lys Lys Ile Phe Lys Lys Glu Glu
                805                 810                 815

Pro Gly Trp Ile Ser Thr Ile Ser Val Val Glu Ala Glu Trp Asn Ala
            820                 825                 830

Cys Thr Gln Thr Leu Glu Gly His Gly Ser Ser Val Leu Ser Val Ala
        835                 840                 845

Phe Ser Ala Asp Gly Gln Arg Val Ala Ser Gly Ser Asp Asp Lys Thr
850                 855                 860

Ile Lys Ile Trp Asp Thr Ala Ser Gly Thr Gly Thr Gln Thr Leu Glu
865                 870                 875                 880

Gly His Gly Gly Ser Val Trp Ser Val Ala Phe Ser Pro Asp Arg Glu
                885                 890                 895

Arg Val Ala Ser Gly Ser Asp Asp Lys Thr Ile Lys Ile Trp Asp Ala
            900                 905                 910

Ala Ser Gly Thr Cys Thr Gln Thr Leu Glu Gly His Gly Gly Arg Val
        915                 920                 925

Gln Ser Val Ala Phe Ser Pro Asp Gly Gln Arg Val Ala Ser Gly Ser
930                 935                 940

Asp Asp His Thr Ile Lys Ile Trp Asp Ala Ala Ser Gly Thr Cys Thr
945                 950                 955                 960

Gln Thr Leu Glu Gly His Gly Ser Ser Val Leu Ser Val Ala Phe Ser
                965                 970                 975

Pro Asp Gly Gln Arg Val Ala Ser Gly Ser Asp Lys Thr Ile Lys
            980                 985                 990

Ile Trp Asp Thr Ala Ser Gly Thr Cys Thr Gln Thr Leu Glu Gly His
        995                 1000                1005

Gly Gly Ser Val Trp Ser Val Ala Phe Ser Pro Asp Gly Gln Arg Val
    1010                1015                1020

Ala Ser Gly Ser Asp Asp Lys Thr Ile Lys Ile Trp Asp Thr Ala Ser
1025                1030                1035                1040

Gly Thr Cys Thr Gln Thr Leu Glu Gly His Gly Gly Trp Val Gln Ser
                1045                1050                1055

Val Val Phe Ser Pro Asp Gly Gln Arg Val Ala Ser Gly Ser Asp Asp
            1060                1065                1070

His Thr Ile Lys Ile Trp Asp Ala Val Ser Gly Thr Cys Thr Gln Thr
        1075                1080                1085

Leu Glu Gly His Gly Asp Ser Val Trp Ser Val Ala Phe Ser Pro Asp

-continued

```
                1090                1095                1100
Gly Gln Arg Val Ala Ser Gly Ser Ile Asp Gly Thr Ile Lys Ile Trp
        1105                1110                1115                1120

Asp Ala Ala Ser Gly Thr Cys Thr Gln Thr Leu Glu Gly His Gly Gly
                1125                1130                1135

Trp Val His Ser Val Ala Phe Ser Pro Asp Gly Gln Arg Val Ala Ser
                1140                1145                1150

Gly Ser Ile Asp Gly Thr Ile Lys Ile Trp Asp Ala Ala Ser Gly Thr
            1155                1160                1165

Cys Thr Gln Thr Leu Glu Gly His Gly Gly Trp Val Gln Ser Val Ala
    1170                1175                1180

Phe Ser Pro Asp Gly Gln Arg Val Ala Ser Gly Ser Ser Asp Lys Thr
1185                1190                1195                1200

Ile Lys Ile Trp Asp Thr Ala Ser Gly Thr Cys Thr Gln Thr Leu Glu
                1205                1210                1215

Gly His Gly Gly Trp Val Gln Ser Val Ala Phe Ser Pro Asp Gly Gln
            1220                1225                1230

Arg Val Ala Ser Gly Ser Ser Asp Asn Thr Ile Lys Ile Trp Asp Thr
        1235                1240                1245

Ala Ser Gly Thr Cys Thr Gln Thr Leu Asn Val Gly Ser Thr Ala Thr
    1250                1255                1260

Cys Leu Ser Phe Asp Tyr Thr Asn Ala Tyr Ile Asn Thr Asn Ile Gly
1265                1270                1275                1280

Arg Ile Gln Ile Ala Thr Ala Thr Met Glu Ser Leu Asn Gln Leu Ser
                1285                1290                1295

Ser Pro Val Cys Tyr Ser Tyr Gly Leu Gly Gln Asp His Arg Trp Ile
        1300                1305                1310

Thr Cys Asn Asn Gln Asn Val Leu Trp Leu Pro Pro Glu Tyr His Thr
    1315                1320                1325

Ser Ala Phe Thr Met Gln Gly Arg Lys Ile Val Leu Gly Ser Tyr Ser
1330                1335                1340

Gly Arg Ile Ile Ile Phe Leu Phe Ser Arg Asp Val
1345                1350                1355
```

<210> SEQ ID NO 11
<211> LENGTH: 742
<212> TYPE: PRT
<213> ORGANISM: Thermomonospora curvata
<220> FEATURE:
<223> OTHER INFORMATION: amino acid sequence encoded by the PKWA gene

<400> SEQUENCE: 11

```
Met Ile Glu Pro Leu Gln Pro Gly Asp Pro Gly Arg Ile Gly Pro Tyr
 1               5                  10                  15

Arg Leu Val Ser Arg Leu Gly Ala Gly Gly Met Gly Gln Val Phe Leu
            20                  25                  30

Ala Arg Ser Pro Gly Gly Arg Pro Val Val Lys Val Ile Leu Pro
        35                  40                  45

Glu Tyr Ala Asn Asp Asp Glu Tyr Arg Ile Arg Phe Ala Arg Glu Val
    50                  55                  60

Glu Ala Ala Arg Arg Val Gly Gly Phe His Thr Ala Gln Val Ile Asp
65                  70                  75                  80

Ala Asp Pro Thr Ala Asp Pro Pro Trp Met Ala Thr Ala Tyr Ile Pro
                85                  90                  95

Gly Pro Ser Leu Arg Lys Ala Val Thr Glu Arg Gly Pro Leu Tyr Gly
```

-continued

```
                100                 105                 110
Asn Asn Leu Arg Thr Leu Ala Ala Gly Leu Val Glu Gly Leu Ala Ala
            115                 120                 125
Ile His Ala Cys Gly Leu Val His Arg Asp Phe Lys Pro Ser Asn Ile
        130                 135                 140
Val Leu Ala Ala Asp Gly Pro Arg Val Ile Asp Phe Gly Val Ala Arg
145                 150                 155                 160
Pro Leu Asp Ser Ser Val Met Thr Gln Ser Gly Ala Val Ile Gly Thr
                165                 170                 175
Leu Ala Tyr Met Ser Pro Glu Gln Thr Asp Gly Ser Gln Val Gly Pro
            180                 185                 190
Ala Ser Asp Val Phe Ser Leu Gly Thr Val Leu Ala Phe Ala Ala Thr
        195                 200                 205
Gly Arg Ser Pro Phe Met Ala Asp Ser Ile Gly Glu Ile Ile Ala Arg
    210                 215                 220
Ile Ser Gly Pro Pro Glu Leu Pro Glu Leu Pro Asp Asp Leu Arg
225                 230                 235                 240
Glu Leu Val Tyr Ala Cys Trp Glu Gln Asn Pro Asp Leu Arg Pro Thr
                245                 250                 255
Thr Ala Glu Leu Leu Ala Gln Leu Ser Thr Asp His Thr Gly Asp Asp
            260                 265                 270
Trp Pro Pro Pro His Leu Ser Asp Leu Ile Gly Ser Met Leu Pro Leu
        275                 280                 285
Gly Ala Thr Thr Ser Pro Asn Pro Ser Leu Ala Ile Glu Pro Pro Pro
    290                 295                 300
Pro Ser His Gly Pro Pro Arg Pro Ser Glu Pro Leu Pro Asp Pro Gly
305                 310                 315                 320
Asp Asp Ala Asp Glu Pro Ser Ala Glu Lys Pro Ser Arg Thr Leu Pro
                325                 330                 335
Glu Pro Glu Pro Pro Glu Leu Glu Glu Lys Pro Ile Gln Val Ile His
            340                 345                 350
Glu Pro Glu Arg Pro Ala Pro Thr Pro Pro Arg Pro Arg Glu Pro Ala
        355                 360                 365
Arg Gly Ala Ile Lys Pro Lys Asn Pro Arg Pro Ala Ala Pro Gln Pro
    370                 375                 380
Pro Trp Ser Pro Pro Arg Val Gln Pro Pro Arg Trp Lys Gln Leu Ile
385                 390                 395                 400
Thr Lys Lys Pro Val Ala Gly Ile Leu Thr Ala Val Ala Thr Ala Gly
                405                 410                 415
Leu Val Val Ser Phe Leu Val Trp Gln Trp Thr Leu Pro Glu Thr Pro
            420                 425                 430
Leu Arg Pro Asp Ser Ser Thr Ala Pro Ser Glu Ser Ala Asp Pro His
        435                 440                 445
Glu Leu Asn Glu Pro Arg Ile Leu Thr Thr Asp Arg Glu Ala Val Ala
    450                 455                 460
Val Ala Phe Ser Pro Gly Gly Ser Leu Leu Ala Gly Ser Gly Asp
465                 470                 475                 480
Lys Leu Ile His Val Trp Asp Val Ala Ser Gly Asp Glu Leu His Thr
                485                 490                 495
Leu Glu Gly His Thr Asp Trp Val Arg Ala Val Ala Phe Ser Pro Asp
            500                 505                 510
Gly Ala Leu Leu Ala Ser Gly Ser Asp Asp Ala Thr Val Arg Leu Trp
        515                 520                 525
```

```
Asp Val Ala Ala Ala Glu Glu Arg Ala Val Phe Glu Gly His Thr His
    530                 535                 540
Tyr Val Leu Asp Ile Ala Phe Ser Pro Asp Gly Ser Met Val Ala Ser
545                 550                 555                 560
Gly Ser Arg Asp Gly Thr Ala Arg Leu Trp Asn Val Ala Thr Gly Thr
                565                 570                 575
Glu His Ala Val Leu Lys Gly His Thr Asp Tyr Val Tyr Ala Val Ala
            580                 585                 590
Phe Ser Pro Asp Gly Ser Met Val Ala Ser Gly Ser Arg Asp Gly Thr
        595                 600                 605
Ile Arg Leu Trp Asp Val Ala Thr Gly Lys Glu Arg Asp Val Leu Gln
    610                 615                 620
Ala Pro Ala Glu Asn Val Val Ser Leu Ala Phe Ser Pro Asp Gly Ser
625                 630                 635                 640
Met Leu Val His Gly Ser Asp Ser Thr Val His Leu Trp Asp Val Ala
                645                 650                 655
Ser Gly Glu Ala Leu His Thr Phe Glu Gly His Thr Asp Trp Val Arg
            660                 665                 670
Ala Val Ala Phe Ser Pro Asp Gly Ala Leu Leu Ala Ser Gly Ser Asp
        675                 680                 685
Asp Arg Thr Ile Arg Leu Trp Asp Val Ala Ala Gln Glu Glu His Thr
    690                 695                 700
Thr Leu Glu Gly His Thr Glu Pro Val His Ser Val Ala Phe His Pro
705                 710                 715                 720
Glu Gly Thr Thr Leu Ala Ser Ala Ser Glu Asp Gly Thr Ile Arg Ile
                725                 730                 735
Trp Pro Ile Ala Thr Glu
            740
```

```
<210> SEQ ID NO 12
<211> LENGTH: 1272
<212> TYPE: DNA
<213> ORGANISM: HUMAN
<220> FEATURE:
<223> OTHER INFORMATION: RET 16.2 splice variant

<400> SEQUENCE: 12
gaattcggct ttcacctgcg cggcacgtga cccgcaccgc ccgtgggcac cttgaaggcg      60
gatcccgcgc gccccgctc ctgcaggctg ttttcttca aataaagaac atggtgaaac      120
tgattcacac attagctgat catggtgacg atgtcaactg ctgtgccttc tccttttccc      180
tcttggctac ttgctccttg gacaaaacaa ttcgcctgta ctcgttacgt gactttactg      240
aactgccaca ttctccattg aagtttcata cctatgctgt ccactgctgc tgtttctccc      300
cttcaggaca tattttggca tcgtgttcaa cagatggtac cactgtccta tggaatactg      360
aaaatggaca gatgctggca gtgatggaac agcctagtgg cagccctgtg agggtttgcc      420
agttttcccc agactccacg tgtttggcat caggggcagc tgatggaact gtggttttgt      480
ggaatgcaca gtcatacaaa ttatatagat gtggtagtgt taaagatggc tccttggcgg      540
catgtgcatt ttctcctaat ggaagcttct tgtcactggg ctcctcatgt ggtgattttaa      600 cagtgtggga tgataaaatg aggtgtctgc atagtgaaaa agcacatgat cttggaatta      660
cctgctgcga ttttttcttca cagccagttt ctgatggaga caaggtcctt cagtttttc      720 gactggcatc atgtggtcag gattgccaag tcaaaatttg gattgtttct tttacccata      780
```

-continued

```
tcttagcaag gcgcacagaa catcagctga agcaatttac cgaagattgg tcagaggagg    840
tcgtctcaac atggctttgt gcacaagatt taaaagatcc tgttggtatt ttcaagatga    900
ataacattga tggaaaagaa ctgttgaatc ttacaaaaga aagtctggct gatgatttga    960
aaattgaatc tctaggactg cgtagtaaag tgctgaggaa aattgaagag ctcaggacca   1020
aggttaaatc cctttcttca ggaattcctg atgaatttat atgtccaata actagagaac   1080
ttatgaaaga tccggtcatc gcatcagatg gctattcata tgaaaaggaa gcaatggaaa   1140
attggatcag caaaaagaaa cgtacaagtc ccatgacaaa tcttgttctt ccttcagcgg   1200
tacttacacc aaataggact ctgaaaatgg ccatcaatag atggctggag acacaccaaa   1260
agtaaagaat tc                                                      1272
```

<210> SEQ ID NO 13
<211> LENGTH: 384
<212> TYPE: PRT
<213> ORGANISM: HUMAN
<220> FEATURE:
<223> OTHER INFORMATION: RET 16.2 splice variant

<400> SEQUENCE: 13

```
Met Val Lys Leu Ile His Thr Leu Ala Asp His Gly Asp Asp Val Asn
  1               5                  10                  15

Cys Cys Ala Phe Ser Phe Ser Leu Leu Ala Thr Cys Ser Leu Asp Lys
                 20                  25                  30

Thr Ile Arg Leu Tyr Ser Leu Arg Asp Phe Thr Glu Leu Pro His Ser
             35                  40                  45

Pro Leu Lys Phe His Thr Tyr Ala Val His Cys Cys Phe Ser Pro
         50                  55                  60

Ser Gly His Ile Leu Ala Ser Cys Ser Thr Asp Gly Thr Val Leu
 65                  70                  75                  80

Trp Asn Thr Glu Asn Gly Gln Met Leu Ala Val Met Glu Gln Pro Ser
                 85                  90                  95

Gly Ser Pro Val Arg Val Cys Gln Phe Ser Pro Asp Ser Thr Cys Leu
            100                 105                 110

Ala Ser Gly Ala Ala Asp Gly Thr Val Val Leu Trp Asn Ala Gln Ser
        115                 120                 125

Tyr Lys Leu Tyr Arg Cys Gly Ser Val Lys Asp Gly Ser Leu Ala Ala
    130                 135                 140

Cys Ala Phe Ser Pro Asn Gly Ser Phe Val Thr Gly Ser Ser Cys
145                 150                 155                 160

Gly Asp Leu Thr Val Trp Asp Asp Lys Met Arg Cys Leu His Ser Glu
                165                 170                 175

Lys Ala His Asp Leu Gly Ile Thr Cys Cys Asp Phe Ser Ser Gln Pro
            180                 185                 190

Val Ser Asp Gly Glu Gln Gly Leu Gln Phe Phe Arg Leu Ala Ser Cys
        195                 200                 205

Gly Gln Asp Cys Gln Val Lys Ile Trp Ile Val Ser Phe Thr His Ile
    210                 215                 220

Leu Ala Arg Arg Thr Glu His Gln Leu Lys Gln Phe Thr Glu Asp Trp
225                 230                 235                 240

Ser Glu Glu Val Val Ser Thr Trp Leu Cys Ala Gln Asp Leu Lys Asp
                245                 250                 255

Leu Val Gly Ile Phe Lys Met Asn Asn Ile Asp Gly Lys Glu Leu Leu
            260                 265                 270
```

```
Asn Leu Thr Lys Glu Ser Leu Ala Asp Asp Leu Lys Ile Glu Ser Leu
            275                 280                 285

Gly Leu Arg Ser Lys Val Leu Arg Lys Ile Glu Glu Leu Arg Thr Lys
        290                 295                 300

Val Lys Ser Leu Ser Ser Gly Ile Pro Asp Glu Phe Ile Cys Pro Ile
305                 310                 315                 320

Thr Arg Glu Leu Met Lys Asp Pro Val Ile Ala Ser Asp Gly Tyr Ser
                325                 330                 335

Tyr Glu Lys Glu Ala Met Glu Asn Trp Ile Ser Lys Lys Arg Thr
            340                 345                 350

Ser Pro Met Thr Asn Leu Val Leu Pro Ser Ala Val Leu Thr Pro Asn
        355                 360                 365

Arg Thr Leu Lys Met Ala Ile Asn Arg Trp Leu Glu Thr His Gln Lys
    370                 375                 380

<210> SEQ ID NO 14
<211> LENGTH: 1908
<212> TYPE: DNA
<213> ORGANISM: HUMAN
<220> FEATURE:
<223> OTHER INFORMATION: RET 16.3 splice variant

<400> SEQUENCE: 14
```

| | | | | |
|---|---|---|---|---|
| gaattcggct cgaggccggc gcccgccccg ccagcctcac ctgcgcggca cgtgacccgc | 60 |
| accgcccgtg ggcaccttga aggcggatcc cgcgcgcccc cgctcctgca ggctgttttt | 120 |
| cttcaaataa agaacatggt gaaactgatt cacacattag ctgatcatgg tgacgatgtc | 180 |
| aactgctgtg ccttctcctt ttccctcttg gctacttgct ccttggacaa aacaattcgc | 240 |
| ctgtactcgt tacgtgactt tactgaactg ccacattctc cattgaagtt tcatacctat | 300 |
| gctgtccact gctgctgttt ctccccttca ggacatattt tggcatcgtg ttcaacagat | 360 |
| ggtaccactg tcctatggaa tactgaaaat ggacagatgc tggcagtgat ggaacagcct | 420 |
| agtggcagcc ctgtgagggt ttgccagttt tccccagact ccacgtgttt ggcatcaggg | 480 |
| gcagctgatg gaactgtggt tttgtggaat gcacagtcat acaaattata tagatgtggt | 540 |
| agtgttaaag atggctcctt ggcggcatgt gcattttctc ctaatggaag cttctttgtc | 600 |
| actggctcct catgtggtga tttaacagtg tgggatgata aaatgagctg tctgcatagt | 660 |
| gaaaaagcac atgatcttgg aattacctgc tgcgattttt cttcacagcc agtttctgat | 720 |
| ggagaacaag tcttcagtt ttttcgactg gcatcatgtg gtcaggattg ccaagtcaaa | 780 |
| atttggattg tttcttttac ccatatctta ggttttgaat aaaatataa aagtacactg | 840 |
| agtgggcact gtgctcctgt tctggcttgt gcttttttccc atgatgggca gatgctagtc | 900 |
| tcagggtcag tggataagtc tgtcatagta tatgatacta atactgagaa tatacttcac | 960 |
| acattgactc agcacaccag gtatgtcaca acttgtgctt ttgcacctaa tacccttta | 1020 |
| cttgctactg gttcaatgga caaaacagtg aacatctggc aatttgacct ggaaacactt | 1080 |
| tgccaagcaa ggcgcacaga acatcagctg aagcaattta ccgaagattg gtcagaggag | 1140 |
| gatgtctcaa catggctttg tgcacaagat ttaaagatc ttgttggtat tttcaagatg | 1200 |
| aataacattg atgaaaaga actgttgaat cttacaaaag aaagtctggc tgatgatttg | 1260 |
| aaaattggct ggagtcctct ggcatggtca tgcctcactg cagcttcaac ctcctgggct | 1320 |
| caagtgatcc tcctacctcg gcctcaatct ctaggactgc gtagtaaagt gctgaggaaa | 1380 |
| attgaagagc tcaggaccaa ggttaaatcc ctttcttcag gaattcctga tgaatttata | 1440 |

-continued

```
tgtccaataa ctagagaact tatgaaagat ccggtcatcg catcagatgg ctattcatat    1500
gaaaaggaag caatggaaaa ttggatcagc aaaaagaaac gtacaagtcc catgacaaat    1560
cttgttcttc cttcagcggt acttacacca aataggactc tgaaaatggc catcaataga    1620
tggctggaga cacaccaaaa gtaaaattgt tgatattgta ttatttatat tttcagtgat    1680
ctcatttgaa tgatttatag gtaaatacta atcagacatt attaaaagca aaacaggaaa    1740
aagtaaaact tcttaaattt agttacctat aaaaattgtc aattttcatt ctttaaaaaa    1800
cacatggact tactataaaa gccttttttgt actagtgaaa agaatcttca gctatataga    1860 aataagtta tcctttaaaa aaaaaaaaaa aaaaaaaagg gcggccgc                  1908
```

<210> SEQ ID NO 15
<211> LENGTH: 502
<212> TYPE: PRT
<213> ORGANISM: HUMAN
<220> FEATURE:
<223> OTHER INFORMATION: RET 16.3 splice variant

<400> SEQUENCE: 15

```
Met Val Lys Leu Ile His Thr Leu Ala Asp His Gly Asp Asp Val Asn
 1               5                  10                  15

Cys Cys Ala Phe Ser Phe Ser Leu Leu Ala Thr Cys Ser Leu Asp Lys
            20                  25                  30

Thr Ile Arg Leu Tyr Ser Leu Arg Asp Phe Thr Glu Leu Pro His Ser
        35                  40                  45

Pro Leu Lys Phe His Thr Tyr Ala Val His Cys Cys Cys Phe Ser Pro
    50                  55                  60

Ser Gly His Ile Leu Ala Ser Cys Ser Thr Asp Gly Thr Thr Val Leu
65                  70                  75                  80

Trp Asn Thr Glu Asn Gly Gln Met Leu Ala Val Met Glu Gln Pro Ser
                85                  90                  95

Gly Ser Pro Val Arg Val Cys Gln Phe Ser Pro Asp Ser Thr Cys Leu
            100                 105                 110

Ala Ser Gly Ala Ala Asp Gly Thr Val Val Leu Trp Asn Ala Gln Ser
        115                 120                 125

Tyr Lys Leu Tyr Arg Cys Gly Ser Val Lys Asp Gly Ser Leu Ala Ala
    130                 135                 140

Cys Ala Phe Ser Pro Asn Gly Ser Phe Phe Val Thr Gly Ser Ser Cys
145                 150                 155                 160

Gly Asp Leu Thr Val Trp Asp Asp Lys Met Arg Cys Leu His Ser Glu
                165                 170                 175

Lys Ala His Asp Leu Gly Ile Thr Cys Cys Asp Phe Ser Ser Gln Pro
            180                 185                 190

Val Ser Asp Gly Glu Gln Gly Leu Gln Phe Phe Arg Leu Ala Ser Cys
        195                 200                 205

Gly Gln Asp Cys Gln Val Lys Ile Trp Ile Val Ser Phe Thr His Ile
    210                 215                 220

Leu Gly Phe Glu Leu Lys Tyr Lys Ser Thr Leu Ser Gly His Cys Ala
225                 230                 235                 240

Pro Val Leu Ala Cys Ala Phe Ser His Asp Gly Gln Met Leu Val Ser
                245                 250                 255

Gly Ser Val Asp Lys Ser Val Ile Val Tyr Asp Thr Asn Thr Glu Asn
            260                 265                 270

Ile Leu His Thr Leu Thr Gln His Thr Arg Tyr Val Thr Thr Cys Ala
        275                 280                 285
```

Phe Ala Pro Asn Thr Leu Leu Leu Ala Thr Gly Ser Met Asp Lys Thr
         290                 295                 300

Val Asn Ile Trp Gln Phe Asp Leu Glu Thr Leu Cys Gln Ala Arg Arg
305                 310                 315                 320

Thr Glu His Gln Leu Lys Gln Phe Thr Glu Asp Trp Ser Glu Glu Asp
                325                 330                 335

Val Ser Thr Trp Leu Cys Ala Gln Asp Leu Lys Asp Leu Val Gly Ile
            340                 345                 350

Phe Lys Met Asn Asn Ile Asp Gly Lys Glu Leu Leu Asn Leu Thr Lys
        355                 360                 365

Glu Ser Leu Ala Asp Asp Leu Lys Ile Gly Trp Ser Pro Leu Ala Trp
370                 375                 380

Ser Cys Leu Thr Ala Ala Ser Thr Ser Trp Ala Gln Val Ile Leu Leu
385                 390                 395                 400

Pro Arg Pro Gln Ser Leu Gly Leu Arg Ser Lys Val Leu Arg Lys Ile
                405                 410                 415

Glu Glu Leu Arg Thr Lys Val Lys Ser Leu Ser Ser Gly Ile Pro Asp
            420                 425                 430

Glu Phe Ile Cys Pro Ile Thr Arg Glu Leu Met Lys Asp Pro Val Ile
        435                 440                 445

Ala Ser Asp Gly Tyr Ser Tyr Glu Lys Glu Ala Met Glu Asn Trp Ile
    450                 455                 460

Ser Lys Lys Lys Arg Thr Ser Pro Met Thr Asn Leu Val Leu Pro Ser
465                 470                 475                 480

Ala Val Leu Thr Pro Asn Arg Thr Leu Lys Met Ala Ile Asn Arg Trp
                485                 490                 495

Leu Glu Thr His Gln Lys
            500

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:  11587
      oligonucleotide

<400> SEQUENCE: 16
gcacagccgc caaggagcca c                                            21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:  Primer, JNF
      346

<400> SEQUENCE: 17
tcacctgcgc ggcacgtgac cc                                           22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:  Primer, JNF
      493

<400> SEQUENCE: 18
tttacttttg gtgtgtctcc agcc                                                    24

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Primer, JNF
      494

<400> SEQUENCE: 19
ttacttttgg tgtgtctcca gccatctatt gatggc                                       36

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer, JNF
      232

<400> SEQUENCE: 20
ggcagatgct agtctcaggg                                                         20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer, JNF
      233

<400> SEQUENCE: 21
gggatttaac cttggtcctg                                                         20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide, 11590

<400> SEQUENCE: 22
gcacacacgc agccagaga                                                          19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide, 11591

<400> SEQUENCE: 23
agagaccgac gcacacacg                                                          19

<210> SEQ ID NO 24
<211> LENGTH: 50
<212> TYPE: PRT
<213> ORGANISM: Artificial Sequence
<220> FEATURE:
<223> OTHER INFORMATION: Description of Artificial Sequence: U box
      domain of RET16

<400> SEQUENCE: 24

-continued

```
Glu Phe Ile Cys Pro Ile Thr Arg Glu Leu Met Lys Asp Pro Val Ile
 1               5                  10                  15

Ala Ser Asp Gly Tyr Ser Tyr Glu Lys Glu Ala Met Glu Asn Trp Ile
             20                  25                  30

Ser Lys Lys Lys Arg Thr Ser Pro Met Thr Asn Leu Val Leu Pro Ser
         35                  40                  45

Ala Val
    50

<210> SEQ ID NO 25
<211> LENGTH: 52
<212> TYPE: PRT
<213> ORGANISM: Artificial Sequence
<220> FEATURE:
<223> OTHER INFORMATION: Description of Artificial Sequence:  U box
      domain of PRP19

<400> SEQUENCE: 25

Met Leu Cys Ala Ile Ser Gly Lys Val Pro Arg Arg Pro Val Leu Ser
 1               5                  10                  15

Pro Lys Ser Arg Thr Ile Phe Glu Lys Ser Leu Leu Glu Gln Tyr Val
             20                  25                  30

Lys Asp Thr Gly Asn Asp Pro Ile Thr Asn Glu Pro Leu Ser Ile Glu
         35                  40                  45

Glu Ile Val Glu
    50
```

US 7,198,911 B2

IDENTIFICATION AND CLONING OF A NOVEL HUMAN GENE, RET16, INVOLVED IN THE INTRACELLULAR SIGNALING CASCADE

This application claims benefit of application U.S. Ser. No. 60/294,181, filed May 29, 2001 and U.S. Ser. No. 60/269,366, filed Feb. 16, 2001, the contents of which are hereby incorporated by reference herein in their entireties.

FIELD OF THE INVENTION

The present invention relates to the identification and cloning of a novel full-length human RET16 gene and its encoded polypeptide product, which is expressed in TNF-stimulated human lung microvascular endothelial cells. The invention further relates to orthologs of RET16 and the putative role of the RET16 polynucleotide sequence and its encoded product as a cell signaling molecule in the intracellular signaling cascade. The present invention also relates to uses of the RET16 polynucleotide, polypeptide and modulators thereof in therapeutics and methods involving inflammation and inflammatory diseases, conditions, or disorders and/or involving diseases associated with uncontrolled cell growth, such as cancers, tumors, neoplasms and the like.

BACKGROUND OF THE INVENTION

The development of inflammatory disease is characterized by infiltration of circulating blood cells, e.g., leukocytes, across the endothelium into the tissue. A number of key events occur in the endothelial cells that mediate this "gateway" function. The endothelial cells express receptors and chemokines that sequentially tether the leukocytes, activate them, cause them to tightly adhere, and extravasate between the endothelial cell junctions. This process is initiated by the production of early inflammatory mediators such as tumor necrosis factor (TNF).

The coordinated stimulation of expression of this series of receptors and chemokines is mediated by intracellular signaling molecules, including transcription factors, kinases and scaffolding proteins. These signaling molecules form a signaling cascade that may be a "master switch" for the development of inflammatory processes. Components of this cascade, such as NF-κB, are known. The analysis of genes that are differentially expressed in TNF-activated endothelium can help to identify components of the above-described "master switch" cascade.

The present invention provides the RET16 gene expressed in TNF-alpha-activated human endothelial cells, whose encoded product is regarded to function as a cell signaling molecule involved in the cell signaling cascade. Molecules which play a role in the cell signaling cascade are involved in cellular responses to inflammatory agents, such as cytokines, lymphokines, chemokines, leukotrienes and the like. Further, as a candidate cell signaling protein involved in the cell signaling cascade, RET16 is regarded to be involved in a variety of cell growth-related diseases or disorders.

SUMMARY OF THE INVENTION

The present invention provides a newly discovered human gene and its encoded product, called RET16, which was found to be expressed in human microvascular endothelial cells that had been stimulated with TNF-alpha. According to the present invention, RET16 is a cytoplasmic protein having activity as a cell signaling protein.

One aspect of the invention provides the RET16 polynucleotide sequence as depicted in SEQ ID NO:1. The present invention also provides a polynucleotide sequence comprising the complement of SEQ ID NO:1, or variants thereof. In addition, the present invention features polynucleotide sequences which hybridize under moderate or high stringency conditions to the polynucleotide sequence of SEQ ID NO:1.

Another aspect of the invention provides the RET16 polypeptide, encoded by the polynucleotide of SEQ ID NO:1 and having the amino acid sequence of SEQ ID NO:2, or a functional or biologically active portion thereof. In accordance with the present invention, an isolated, substantially purified RET16 protein is provided.

Yet another aspect of the present invention provides an isolated polynucleotide sequence (1532 bp) of the human RET16 open reading frame cDNA (SEQ ID NO:3) and the polypeptide sequence encoded by the open reading frame human RET16 and having the amino acid sequence depicted in SEQ ID NO:4, or a functional or biologically active portion thereof. An isolated, substantially purified RET16 protein or polypeptide, e.g., SEQ ID NO:4, is provided. Also in accordance with the present invention, the 1532 bp human RET16 (also called RET16.1) open reading frame polynucleotide sequence cloned into a vector has been deposited with the American Type Culture Collection (ATCC), 10801 University Boulevard, Manassas, Va. 20110-2209 on Mar. 7, 2001 under ATCC Accession No. PTA-3161 according to the terms of the Budapest Treaty. Vectors containing the cloned RET16 variant cDNAs, i.e., RET16.2 and RET16.3, have also been deposited with the American Type Culture Collection (ATCC), 10801 University Boulevard, Manassas, Va. 20110-2209 on Mar. 7, 2001 under ATCC Accession No. PTA-3161 according to the terms of the Budapest Treaty. Accordingly, the present invention provides a RET16 cDNA nucleic acid sequence comprising ATCC Deposit Accession No. PTA-3161.

A further aspect of the present invention provides a polynucleotide sequence comprising the complement of SEQ ID NO:3, or variants thereof. In addition, the present invention features polynucleotide sequences which hybridize under moderate or high stringency conditions to the polynucleotide sequence of SEQ ID NO:3. In addition, a 630 bp partial nucleic acid sequence of human RET16 (SEQ ID NO:5) is provided.

Another aspect of the present invention provides variants of RET16. In accordance with the invention, an isolated RET16.2 variant polynucleotide (SEQ ID NO:12) and its encoded amino acid sequence (SEQ ID NO:13) are provided. In addition, , an isolated RET16.3 variant polynucleotide (SEQ ID NO:14) and its encoded amino acid sequence (SEQ ID NO:15) are provided. Portions or fragments, preferably functional or biologically active portions or fragments of these sequences are also provided.

An additional feature of the invention provides mouse and rat orthologs of the human RET16 protein. According to the invention, SEQ ID NO:6 depicts the polynucleotide sequence of the mouse RET16 ortholog. SEQ ID NO:7 depicts the amino acid sequence of the mouse RET16 polypeptide ortholog encoded by SEQ ID NO:6. SEQ ID NO:8 depicts a partial polynucleotide sequence of the rat RET16 ortholog; and SEQ ID NO:9 depicts the amino acid sequence of the partial polypeptide sequence of the rat RET16 ortholog encoded by SEQ ID NO:8.

Another feature of the invention is to provide compositions comprising the RET16 polynucleotide sequence, preferably human RET16, or a fragment thereof, or the encoded RET16 polypeptide, or a fragment or portion thereof. Also provided by the present invention are pharmaceutical compositions comprising at least one RET16 polypeptide, or a functional portion thereof, wherein the compositions further comprise a pharmaceutically acceptable vehicle, e.g., a carrier, excipient, or diluent.

Yet another aspect of the present invention provides N-terminal, C-terminal, or internal deletion polypeptides of the encoded RET16 polypeptides and compositions comprising these deletion polypeptides. Polynucleotides encoding these deletion polypeptides are also provided. The use of the deletion polypeptides as immunogenic and/or antigenic epitopes is described further herein.

A further aspect of the present invention provides the polynucleotide sequences of RET16.1, RET16.2, RET16.3 and the RET16 mouse ortholog lacking the initiating start codon, in addition to the resulting encoded polypeptides of RET16.1, RET16.2, RET16.3 and mouse RET16. More specifically, polynucleotide corresponding to nucleotides 151 through 1575 of SEQ ID NO:1, and the polypeptide corresponding to amino acids 2 through 476 of SEQ ID NO:2 are provided; the polynucleotide corresponding to nucleotides 114 through 1262 of SEQ ID NO:12, and the polypeptide corresponding to amino acids 2 through 384 of SEQ ID NO:13 are provided; the polynucleotide corresponding to nucleotides 139 through 1641 of SEQ ID NO:14, and the polypeptide corresponding to amino acids 2 through 502 of SEQ ID NO:15 are provided; and the polynucleotide corresponding to nucleotides 19 through 1443 of SEQ ID NO:6, and the polypeptide corresponding to amino acids 2 through 475 of SEQ ID NO:7. Also provided are recombinant vectors comprising the RET16.1, RET16.2, RET16.3 and mouse RET16 encoding sequences, and host cells comprising the vectors as described herein.

Another aspect of the invention provides an antisense of the RET16 nucleic acid sequence, preferably, an antisense to the human RET16 nucleic acid sequence, as well as oligonucleotides, fragments, or portions of the RET16 nucleic acid molecule or antisense molecule. Also provided are expression vectors and host cells comprising polynucleotides that encode the human RET16 polypeptide, or portions or fragments thereof.

Yet another aspect of the invention provides methods for producing a polypeptide comprising the amino acid sequence depicted in SEQ ID NO:2 or SEQ ID NO:4, or a fragment thereof, comprising the steps of a) cultivating a host cell containing an expression vector containing at least a functional fragment of the polynucleotide sequence encoding the human RET16 polypeptide according to this invention under conditions suitable for the expression of the polynucleotide; and b) recovering the polypeptide from the host cell.

A further feature of the invention provides antibodies, and binding fragments thereof, which bind specifically to the RET16 polypeptide, or an epitope thereof, for use as therapeutics and diagnostic agents.

Yet another feature of the invention provides methods for screening for agents or molecules which bind to and/or modulate the RET16 polypeptide, preferably human RET16 polypeptide, e.g., inhibitors, other intracellular signaling molecules and antagonists, as well as modulators, particularly, inhibitors and antagonists, particularly those that are obtained from the screening methods described. Also provided are methods to screen for inhibitors or activators of the interaction, e.g., a binding interaction, of the RET16 protein with one or more other cell signaling proteins.

Another aspect of the invention provides a substantially purified antagonist or inhibitor of the RET16 polypeptides of the invention, e.g., SEQ ID NO:2, SEQ ID NO:4, SEQ ID NO:13, or SEQ ID NO:15. In this regard, and by way of a nonlimiting example, a purified antibody that binds to a polypeptide comprising all or an immunogenic and/or antigenic portion of the amino acid sequence of the RET16 polypeptides of the invention, e.g., SEQ ID NO:2, SEQ ID NO:4, SEQ ID NO:13, or SEQ ID NO:15 is provided.

Yet another aspect of the invention provides a substantially purified agonist or activator of the RET16 polypeptides of the invention, e.g., SEQ ID NO:2, SEQ ID NO:4, SEQ ID NO:13, or SEQ ID NO:15.

A further aspect of the invention provides RET16 nucleic acid sequences, polypeptides, peptides and antibodies for use in the diagnosis and/or screening of disorders or diseases associated with expression of the RET16 polynucleotide and its encoded polypeptide involved in the cell signaling cascade as described herein (e.g., see FIG. 9).

Another aspect of the invention provides RET16 probes or primers for detecting RET16-related diseases and/or for monitoring a patient's response to therapy or treatments of RET16-associated diseases or disorders. The probe or primer sequences comprise nucleic acid or amino acid sequences of RET16 as described herein.

Another feature of the invention provides kits for screening and diagnosis of disorders associated with aberrant or uncontrolled cellular expression of the RET16 polynucleotide and its encoded polypeptide as described herein. Such kits can be employed for the determination of the nucleotide sequences of human RET16 alleles. The kits can comprise reagents and instructions for amplification-based assays, nucleic acid probe assays, protein nucleic acid probe assays, antibody assays, or any combination thereof.

In another of its aspects the invention provides a method for detecting a polynucleotide that encodes the RET16 polypeptide in a biological sample comprising the steps of: a) hybridizing the complement of the polynucleotide sequence encoding SEQ ID NO:2 or SEQ ID NO:4 to a nucleic acid material of a biological sample, thereby forming a hybridization complex; and b) detecting the hybridization complex, wherein the presence of the complex correlates with the presence of a polynucleotide encoding the RET16 polypeptide in the biological sample. The nucleic acid material can be further amplified by the polymerase chain reaction prior to hybridization.

Yet another aspect of this invention provides methods for detecting genetic predisposition, susceptibility and/or response to treatment or therapy of various RET16-associated diseases, disorders, or conditions, as described further herein.

Further aspects, features and advantages of the present invention will be better understood upon a reading of the detailed description of the invention when considered in connection with the accompanying figures/drawings.

BRIEF DESCRIPTION OF THE FIGURES

FIG. 1 presents an 1818 bp polynucleotide sequence of human RET16 DNA of the present invention (SEQ ID NO:1), which comprises the full length sequence of the predicted human RET16 transcript. The FIG. 1 nucleic acid sequence (SEQ ID NO:1) comprises the 1532 bp human RET16 open reading frame polynucleotide sequence presented herein as SEQ ID NO:3, (FIG. 4A), as well as additional 3' and 5' sequence. The coding sequence (CDS) of RET16 is encompassed by nucleotide 148 to nucleotide 1575 of SEQ ID NO:1.

FIG. 2 shows the amino acid sequence (SEQ ID NO:2) encoded by the polynucleotide sequence of SEQ ID NO:1. The predicted molecular weight of RET16, i.e., RET16.1, is 52.8 kilodaltons (Kd).

FIG. 3 presents both the human RET16 polynucleotide coding sequence (SEQ ID NO:1) and the deduced amino acid sequence (SEQ ID NO:2) of the 1818 bp human RET16 sequence. As shown, the coding sequence begins at the ATG (methionine) codon at nucleotide position numbers 148–150 of the polynucleotide sequence of SEQ ID NO:1.

FIG. 4A shows the human RET16 open reading frame (ORF) polynucleotide sequence of SEQ ID NO:3. FIG. 4B shows the human RET16 amino acid sequence of the polypeptide (SEQ ID NO:4) encoded by the ORF polynucleotide sequence of SEQ ID NO:3. FIG. 4C presents the 630 base pair partial nucleic acid sequence of human RET16 cDNA (SEQ ID NO:5).

FIG. 5 shows the RET16 polynucleotide sequence derived from mouse, i.e., the murine RET16 ortholog, (SEQ ID NO:6). The coding sequence (CDS) of murine RET16 is encompassed by nucleotide 19 to nucleotide 1443 of SEQ ID NO:6.

FIG. 6 shows the amino acid sequence of the murine RET16 polypeptide (SEQ ID NO:7) encoded by the polynucleotide sequence of murine RET16 cDNA (SEQ ID NO:6). The predicted molecular weight of mouse RET16 is 51.8 Kd.

FIG. 7A presents the results of a human MTN blot in which RET16 transcript was detectable in all tissues, at varying levels. In FIG. 7A, expression was highest in kidney, pancreas and heart, with lower expression levels observed in the placenta, skeletal muscle and liver, and even lower levels in lung and brain. FIG. 7B presents the results of a human MTN blot II, in which RET16 transcript was detectable in all tissues, at varying levels. In FIG. 7B, expression was highest in the testis, with lower expression levels in ovary, prostate, and spleen, and even lower levels in thymus, small intestine, colon and peripheral blood leukocytes. FIG. 7C presents the results of a human MTN blot III, in which RET16 transcript was detectable in most tissues. In FIG. 7C, expression was highest in the thyroid, with lower levels observed in stomach, spinal cord, lymph node, trachea, and adrenal gland. RET16 transcript was virtually undetectable in the bone marrow, although a larger approximately 2.4 kb transcript was detected in bone marrow. FIG. 7D presents the results of a human cancer cell line MTN blot, in which RET16 transcript was detectable in several tumor lines. In FIG. 7D, expression was highest in the Burkitt's lymphoma cell line RAJI, with lower levels observed in the melanoma cell line G-361 and the chronic myelogenous leukemia cell line K-562, and with even lower levels found in HeLa S3, lymphoblastic leukemia MOLT-4, and colorectal adenocarcinoma SW480 cell lines. No detectable expression was observed in the promyelocytic leukemia HL-60 cell line and in the lung carcinoma A549 cell line.

In FIG. 9, the bars represent the relative expression of E-selectin on the surface of HVEC.

FIGS. 10A–10E show various alignments of the human RET16 amino acid sequence with other known and newly-provided sequences. The vertical lines between the sequence residues indicate amino acid identity. Two dots between sequence residues indicate amino acid similarity. One dot between sequence residues indicates amino acid dissimilarity. PileUp was used to generate a multiple sequence alignment on SEQ-WEB GCG, the Blosum62 scoring matrix, gap creation penalty of 8, and gap extension penalty of 2. As will be understood by the skilled practitioner, PileUp creates a multiple sequence alignment using a simplification of the progressive alignment method of Feng and Doolittle (1987, *J. Mol. Evol.*, 25:351–360). The method used is similar to that described by Higgins and Sharp (1989, *CABIOS*, 5:151–153).

Specifically, FIG. 10A presents a sequence alignment of a portion of the human RET16 amino acid sequence from SEQ ID NO:2 or SEQ ID NO:4, (top line) with a portion of the Het-E-1 amino acid sequence of *Podospora anserina* (bottom line of sequence). The published amino acid sequence of *Podospora anserina* beta transducin-like protein encoded by the het-e-1 gene (Accession Number L28125) is provided as SEQ ID NO:10. FIG. 10B presents a sequence alignment of a portion of the human RET16 amino acid sequence from SEQ ID NO:2 or SEQ ID NO:4, (top line), with a portion of the PKWA amino acid sequence of *Thermomonospora curvata* (bottom line of sequence). The published amino acid sequence of *Thermomonospora curvata* PKWA (pkwA) gene (Accession Number AF115313) is provided as SEQ ID NO:11. FIG. 10C presents a sequence alignment of the human RET16 amino acid sequence (SEQ ID NO:2 or SEQ ID NO:4), top line, with the murine RET16 amino acid sequence (SEQ ID NO:7), bottom line. FIG. 10D presents a sequence alignment of human RET16 amino acid sequence (SEQ ID NO:2 or SEQ ID NO:4), top line, with rat RET16 amino acid sequence (SEQ ID NO:9), bottom line. FIG. 10E presents a multiple sequence alignment of human RET16 amino acid sequence (SEQ ID NO:2 or SEQ ID NO:4), (top line) with the Het-E-1 amino acid sequence of *Podospora anserina* (SEQ ID NO:10), (middle line); and the PKWA amino acid sequence of *Thermomonospora curvata* (SEQ ID NO:11), (bottom line of sequence).

FIG. 12 shows an electronic Northern depicting human (hu) RET16 expression. "Clone count" refers to the number of times that the RET16 sequence appeared in a random analysis of the RET16 clone in the listed tissue libraries (Incyte database), thereby confirming that the RET16 gene is expressed in the listed tissue.

FIG. 13 shows the partial RET16 polynucleotide sequence isolated from rat (SEQ ID NO:8), i.e., the rat ortholog of the human RET16 gene.

FIG. 14 shows the amino acid sequence of the rat RET16 partial polypeptide (SEQ ID NO:9) encoded by the polynucleotide sequence of the rat RET16 partial cDNA sequence (SEQ ID NO:8; FIG. 13).

FIG. 15 shows a multiple sequence alignment of human (SEQ ID NO:2 or SEQ ID NO:4), mouse (SEQ ID NO:7) and rat (SEQ ID NO:9) RET16 amino acid sequences using the PileUp program described for FIGS. 10A–10E. Dark highlights indicate conservation among all three orthologs, while the lighter highlights indicate conservation between two of the orthologs. Note that the rat RET16 is only a partial polypeptide sequence. Human RET16 is 82.5% identical to mouse RET16 (muRET16) and 92.9% identical to partial rat RET16 (rRET16). MuRET16 is 98.5% identical to partial rRET16.

FIG. 16 shows a multiple sequence alignment of the RET16.1, RET16.2, RET16.3 splice variant polypeptide sequences. The lightly shaded boxes designate amino acids deleted in RET16.2, which is missing exons 5–8 of RET16.1. Darker shaded boxes designate the additional amino acids present in RET16.3 that are not present in the other RET16 sequences.

FIG. 17 shows an alignment of WD and SAM domains in the human RET16 (SEQ ID NO:2 or SEQ ID NO:4) and murine RET16 (SEQ ID NO:7) polypeptide sequences. The lightly shaded regions indicate the WD repeats and the darker shaded region designates the SAM domain as indicated in the figure. Identical residues are indicated by the boxed regions.

FIGS. 19A and 19B show the human RET16.2 splice variant polynucleotide sequence (SEQ ID NO:12) and encoded amino acid sequence (SEQ ID NO:13), (Example 2). The coding sequence (CDS) of human RET16.2 is encompassed by nucleotide 111 to nucleotide 1262 of SEQ ID NO:12. The predicted molecular weight of RET16.2 is 42.7 Kd.

FIGS. 20A and 20B show the human RET16.3 splice variant polynucleotide sequence (SEQ ID NO:14) and encoded amino acid sequence (SEQ ID NO:15), (Example 2). The coding sequence (CDS) of human RET16.3 is encompassed by nucleotide 136 to nucleotide 1641 of SEQ ID NO:14. The predicted molecular weight of RET16.3 is 55.6 Kd.

FIG. 21 shows an alignment of the consensus residues of the U box domain of the RET16 protein (SEQ ID NO:24) of the present invention and the U box domain of protein PRP19 (SEQ ID NO:25). The annotation of the conserved consensus residues shown in FIG. 21 is modified from Aravind and Koonin, 2002, *Current Biology*, 10(4): R132–R134.

DESCRIPTION OF THE INVENTION

Figure 7A:
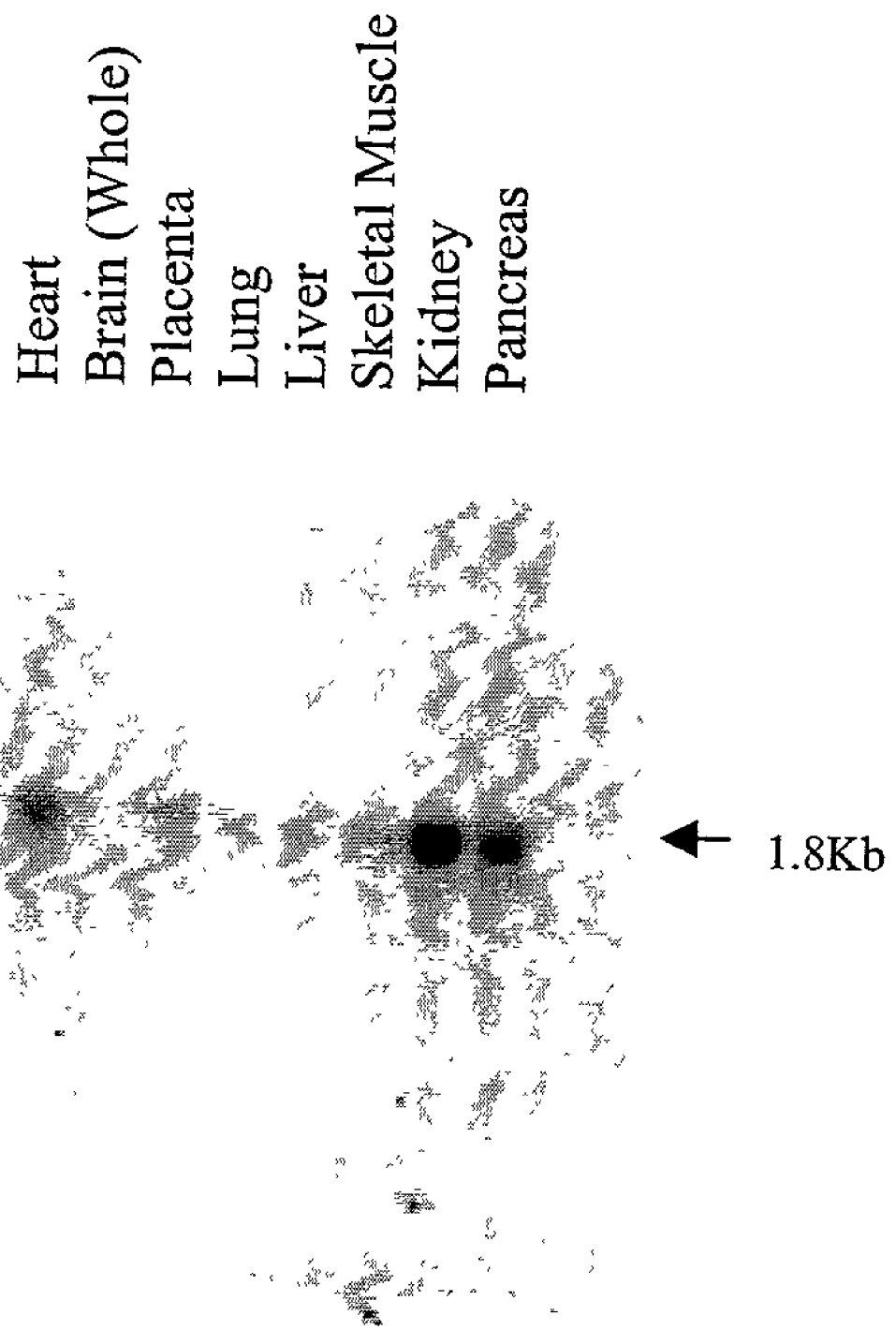
FIGS. 7A–7D show 10 day multiple tissue Northerns (MTNs) probed with the partial cDNA corresponding to the RET16 gene. (See Example 1H). A 1.8 kb transcript was detected in several tissues.
Figure 7B:
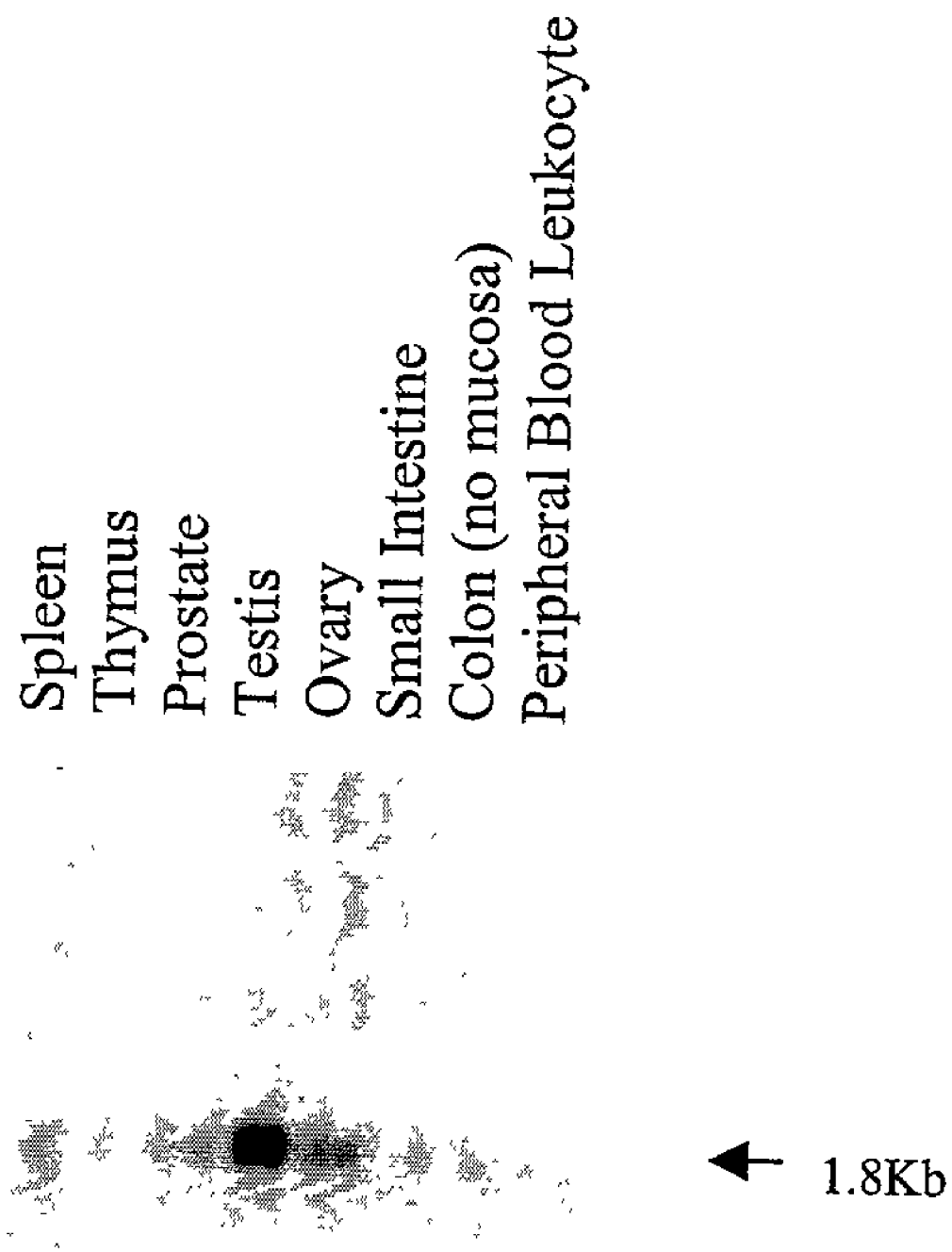
Figure 7C:
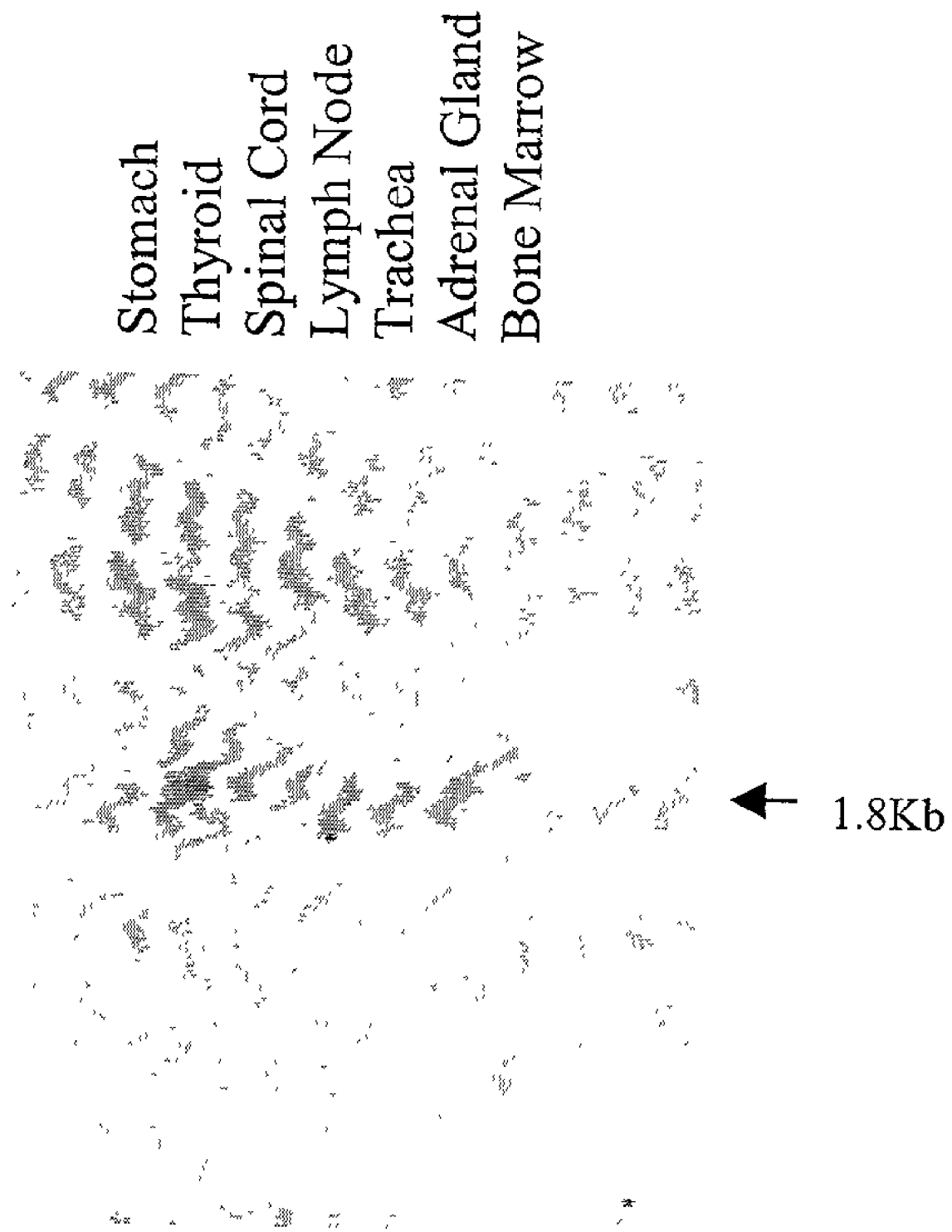
Figure 7D:
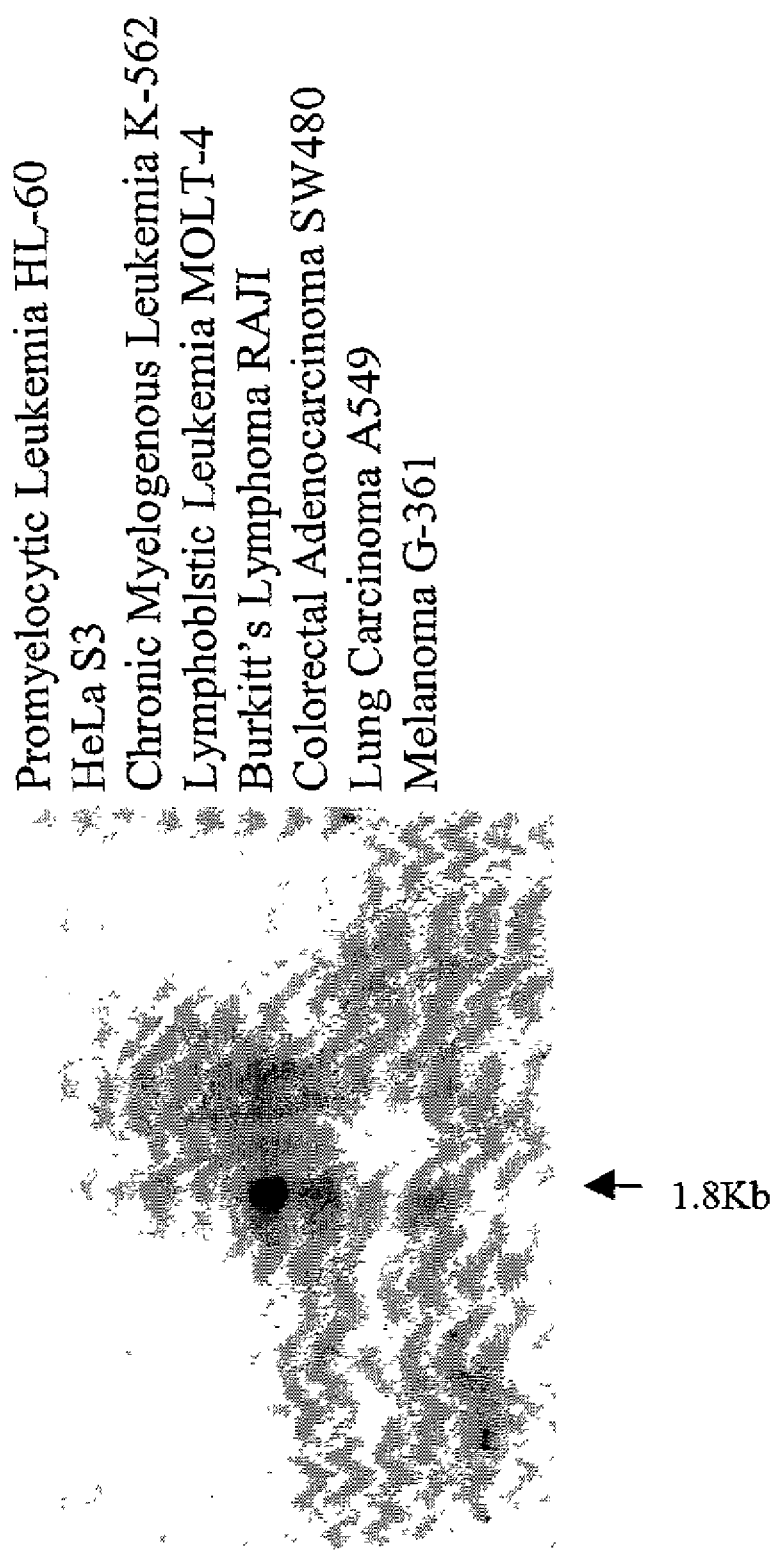
Figure 8:
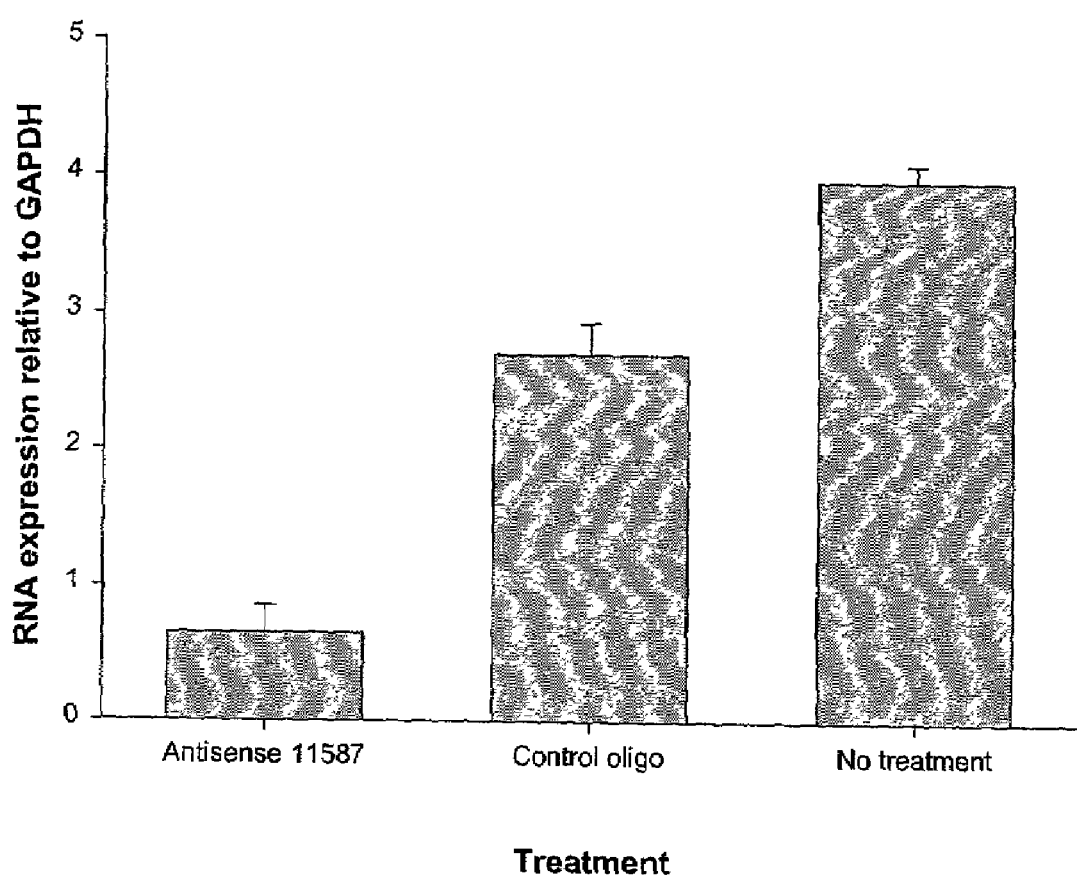
FIG. 8 presents the results of the inhibition of RET16 expression using an antisense oligomer. Shown in FIG. 8 are the levels of RET16 mRNA expression after normalization to GAPDH mRNA expression. Each bar represents the average +/−standard deviation of triplicate transfections. Strong inhibition was observed with oligomer 11587, compared with the control oligomer (76.6%). (See Example 5).

The following definitions are provided to more fully describe the present invention in its various aspects. The definitions are intended to be useful for guidance and elucidation, and are not intended to limit the disclosed invention and its embodiments.

Definitions

The RET16 polypeptide (or protein) refers to the amino acid sequence of isolated and preferably substantially purified RET16 protein, which, although isolated from a human cDNA library source according to the present invention, can be obtained from any species, preferably mammalian, including mouse, rat, non-human primates, and more preferably, human; and from a variety of sources, including natural, synthetic, semi-synthetic, or recombinant. Indeed, the present invention more particularly provides (i) a human RET16 polynucleotide sequence of the full-length human RET16 transcript (SEQ ID NO:1) and the encoded human RET16 polypeptide sequence (SEQ ID NO:2), (FIGS. 1-3); (ii) the human RET16 open reading frame polynucleotide sequence (SEQ ID NO:3) and the encoded human RET16 polypeptide sequence (SEQ ID NO:4); (iii) the murine RET16 polynucleotide sequence (SEQ ID NO:6) and the encoded murine RET16 amino acid sequence (SEQ ID NO:7), (FIGS. 5 and 6), and (iv) a partial nucleic acid sequence of the rat RET16 ortholog (SEQ ID NO:8) and the encoded rat RET16 amino acid sequence (SEQ ID NO:9), (FIGS. 13–14). Functional fragments and portions of the RET16 polynucleotides and polypeptides described herein are also embraced by the present invention.

An agonist (e.g., activator) refers to a molecule which, when bound to the RET16 polypeptide, or a functional fragment thereof, increases or prolongs the duration of the effect of the RET16 polypeptide. Agonists can include proteins, nucleic acids, carbohydrates, or any other molecules that bind to and modulate the effect of RET16 polypeptide. An antagonist (e.g., inhibitor) refers to a molecule which, when bound to the RET16 polypeptide, or a functional fragment thereof, decreases or eliminates the amount or duration of the biological or immunological activity of RET16 polypeptide. Antagonists can include proteins, nucleic acids, carbohydrates, antibodies, or any other molecules that decrease, reduce or eliminate the effect and/or function of the RET16 polypeptide.

"Nucleic acid sequence", as used herein, refers to an oligonucleotide, nucleotide, or polynucleotide (e.g., cDNA, DNA, RNA), and fragments or portions thereof, and to DNA or RNA of genomic or synthetic origin which can be single- or double-stranded, and represent the sense or antisense strand. By way of nonlimiting example, fragments include nucleic acid sequences that are greater than about 10–60 nucleotides in length, preferably about 20–60 nucleotides, and also preferably include fragments that are at least 70–100 nucleotides, or which are at least 1000 nucleotides or greater in length. Nucleic acids for use as probes or primers can differ in length as described herein.

Similarly, "amino acid sequence" as used herein refers to an oligopeptide, peptide, polypeptide, or protein sequence, and fragments or portions thereof, and to naturally occurring or synthetic molecules. Amino acid sequence fragments are typically from about 4 or 5 to about 35, preferably from about 5 to about 15 or 25 amino acids in length and, optimally, retain the biological activity or function of the RET16 polypeptide. However, it will be understood that larger amino acid fragments can be used, depending on the purpose therefor, e.g., fragments of from about 15 to about 50 or 60 amino acids.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms RET16 polypeptide and RET16 protein are frequently used interchangeably herein to refer to the encoded product of the RET16 nucleic acid sequence of the present invention.

A variant of the RET16 polypeptide can refer to an amino acid sequence that is altered by one or more amino acids.

The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Minor variations can also include amino acid deletions or insertions, or both. Guidance in determining which amino acid residues can be substituted, inserted, or deleted without abolishing functional biological or immunological activity can be found using computer programs well known in the art, for example, DNASTAR software.

An allele or allelic sequence is an alternative form of the RET16 nucleic acid sequence. Alleles can result from at least one mutation in the nucleic acid sequence and can yield altered mRNAs or polypeptides whose structure or function may or may not be altered. Any given gene, whether natural or recombinant, can have none, one, or many allelic forms. Common mutational changes which give rise to alleles are generally ascribed to natural deletions, additions, or substitutions of nucleotides. Each of these types of changes can occur alone, or in combination with the others, one or more times in a given sequence.

Altered nucleic acid sequences encoding the RET16 polypeptide include nucleic acid sequences containing deletions, insertions and/or substitutions of different nucleotides resulting in a polynucleotide that encodes the same or a functionally equivalent RET16 polypeptide. Altered nucleic acid sequences can further include polymorphisms of the polynucleotide encoding the RET16 polypeptide; such polymorphisms may or may not be readily detectable using a particular oligonucleotide probe. The encoded protein can also contain deletions, insertions, or substitutions of amino acid residues which produce a silent change and result in a functionally equivalent RET16 protein of the present invention. Deliberate amino acid substitutions can be made on the basis of similarity in polarity, charge, solubility, hydrophobicity, hydrophilicity, and/or the amphipathic nature of the residues, as long as the biological activity or function of RET16 protein is retained. For example, negatively charged amino acids can include aspartic acid and glutamic acid; positively charged amino acids can include lysine and arginine; and amino acids with uncharged polar head groups having similar hydrophilicity values can include leucine, isoleucine, and valine; glycine and alanine; asparagine and glutamine; serine and threonine; and phenylalanine and tyrosine.

"Peptide nucleic acid" (PNA) refers to an antisense molecule or anti-gene agent which comprises an oligonucleotide ("oligo") linked to a peptide backbone of amino acid residues, which terminates in lysine. PNA typically comprise oligos of at least 5 nucleotides linked to amino acid residues. These small molecules stop transcript elongation by binding to their complementary strand of nucleic acid (P. E. Nielsen et al., 1993, *Anticancer Drug Des.*, 8:53–63). PNA can be pegylated to extend their lifespan in the cell where they preferentially bind to complementary single stranded DNA and RNA.

Oligonucleotides or oligomers ("oligos") refer to a nucleic acid sequence, preferably comprising contiguous nucleotides, typically of at least about 6 nucleotides to about 60 nucleotides, preferably at least about 8 to 10 nucleotides in length, more preferably at least about 12 nucleotides in length, e.g., about 15 to 35 nucleotides, or about 15 to 25 nucleotides, or about 20 to 35 nucleotides, which can be typically used, for example, as probes or primers, in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe can comprise at least 20–200 nucleotides, preferably, at least 30–100 nucleotides, more preferably, 50–100 nucleotides.

Amplification refers to the production of additional copies of a nucleic acid sequence and is generally carried out using polymerase chain reaction (PCR) technologies, which are well known and practiced in the art (See, D. W. Dieffenbach and G. S. Dveksler, 1995, *PCR Primer, a Laboratory Manual*, Cold Spring Harbor Press, Plainview, N.Y.).

Microarray is an array of distinct polynucleotides or oligonucleotides synthesized on a substrate, such as paper, nylon, or other type of membrane; filter; chip; glass slide; or any other type of suitable solid support.

The term antisense refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNA and can be produced by any method, including synthesis or transcription. Once introduced into a cell, the complementary nucleotides combine with natural sequences produced by the cell to form duplexes which block either transcription or translation. The designation "negative" is sometimes used in reference to the antisense strand, and "positive" is sometimes used in reference to the sense strand.

The term consensus refers to the sequence that reflects the most common choice of base or amino acid at each position among a series of related DNA, RNA, or protein sequences. Areas of particularly good agreement often represent conserved functional domains.

A deletion refers to a change in either nucleotide or amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A substitution refers to the replacement of one or more nucleotides or amino acids by different nucleotides or amino acids.

A derivative nucleic acid molecule refers to the chemical modification of a nucleic acid encoding, or complementary to, the encoded RET16 polypeptide. Such modifications include, for example, replacement of hydrogen by an alkyl, acyl, or amino group. A nucleic acid derivative encodes a polypeptide which retains the essential biological and/or functional characteristics of the natural molecule. A derivative polypeptide is one which is modified by glycosylation, pegylation, or any similar process that retains the biological and/or functional or immunological activity of the polypeptide from which it is derived.

The term "biologically active", i.e., functional, refers to a protein or polypeptide or peptide fragment thereof having structural, regulatory, or biochemical functions of a naturally occurring molecule. Likewise, "immunologically active" refers to the capability of the natural, recombinant, or synthetic RET16, or any oligopeptide thereof, to induce a specific immune response in appropriate animals or cells, for example, to generate antibodies, and to bind with specific antibodies.

The term hybridization refers to any process by which a strand of nucleic acid binds with a complementary strand through base pairing.

The term "hybridization complex" refers to a complex formed between two nucleic acid sequences by virtue of the formation of hydrogen bonds between complementary G and C bases and between complementary A and T bases. The hydrogen bonds can be further stabilized by base stacking interactions. The two complementary nucleic acid sequences hydrogen bond in an anti-parallel configuration. A hybridization complex can be formed in solution (e.g., $C_o t$ or $R_o t$ analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms stringency or stringent conditions refer to the conditions for hybridization as defined by nucleic acid composition, salt and temperature. These conditions are well known in the art and can be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors can be varied to generate conditions, either low or high stringency, that are different from but equivalent to the aforementioned conditions.

As will be understood by those of skill in the art, the stringency of hybridization can be altered in order to identify or detect identical or related polynucleotide sequences. As will be further appreciated by the skilled practitioner, Tm can be approximated by the formulas as known in the art, depending on a number of parameters, such as the length of the hybrid or probe in number of nucleotides, or hybridization buffer ingredients and conditions (See, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994–1995, Suppls. 26, 29, 35 and 42; pp. 2.10.7–2.10.16; G. M. Wahl and S. L. Berger (1987; *Methods Enzymol.* 152:399–407); and A. R. Kimmel, 1987; *Methods of Enzymol.* 152:507–511). As a general guide, Tm decreases approximately 1° C. –1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of nonlimiting example, high stringency refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5× Denhart's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM $Na_3$ citrate•$2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

Moderate stringency refers, by way of nonlimiting example, to conditions that permit hybridization in 50% formamide, 5× Denhart's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

Low stringency refers, by way of nonlimiting example, to conditions that permit hybridization in 10% formamide, 5× Denhart's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions can be varied using a variety of ingredients, buffers and temperatures well known to and practiced by the skilled practitioner.

The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules can be "partial", in which only some of the nucleic acids bind, or it can be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term homology refers to a degree of complementarity. There can be partial sequence homology or complete homology, wherein complete homology is equivalent to identity, e.g., 100% identity. A partially complementary sequence that at least partially inhibits an identical sequence from hybridizing to a target nucleic acid is referred to using the functional term "substantially homologous." The inhibition of hybridization of the completely complementary sequence to the target sequence can be examined using a hybridization assay (e.g., Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding can be tested by the use of a second target sequence which lacks even a partial degree of complementarity (e.g., less than about 30% identity). In the absence of non-specific binding, the probe will not hybridize to the second non-complementary target sequence.

Those having skill in the art will know how to determine percent identity between/among sequences using, for example, algorithms such as those based on the CLUSTALW computer program (J. D. Thompson et al., 1994, *Nucleic Acids Research*, 2(22):4673–4680), or FASTDB, (Brutlag et al., 1990, *Comp. App. Biosci.*, 6:237–245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations.

Also available to those having skill in this art are the BLAST and BLAST 2.0 algorithms (Altschul et al., 1977, *Nuc. Acids Res.*, 25:3389–3402 and Altschul et al., 1990, *J. Mol. Biol.*, 215:403–410). The BLASTN program for nucleic acid sequences uses as defaults a wordlength (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff & Henikoff, 1989, *Proc. Nat. Acad. Sci., USA*, 89:10915) uses alignments (B) of 50, expectation (E) of 10, M=5, N=4, and a comparison of both strands.

A composition comprising a given polynucleotide sequence refers broadly to any composition containing the given polynucleotide sequence. The composition can comprise a dry formulation or an aqueous solution. Compositions comprising polynucleotide sequence (e.g., SEQ ID NO:1 or SEQ ID NO:3) encoding RET16 polypeptide, or fragments thereof, can be employed as hybridization probes, or as primers. The probes and primers can be stored in freeze-dried form and can be in association with a stabilizing agent such as a carbohydrate. In hybridizations, the probe can be employed in an aqueous solution containing salts (e.g., NaCl), detergents or surfactants (e.g., SDS) and other components (e.g., Denhardt's solution, dry milk, salmon sperm DNA, and the like).

The term "substantially purified" refers to nucleic acid sequences or amino acid sequences that are removed from their natural environment, i.e., isolated or separated by a variety of means, and are at least 60% free, preferably 75% to 85% free, and most preferably 90% or greater free from other components with which they are naturally associated.

The term sample, or biological sample, is meant to be interpreted in its broadest sense. A biological sample suspected of containing nucleic acid encoding the RET16 protein, or fragments thereof, or the RET16 protein itself, can comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

Transformation refers to a process by which exogenous DNA enters and changes a recipient cell. It can occur under natural or artificial conditions using various methods well known in the art. Transformation can rely on any known method for the insertion of foreign nucleic acid sequences into a prokaryotic or eukaryotic host cell. The method is selected based on the type of host cell being transformed and can include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells which transiently express the inserted DNA or RNA for limited periods of time.

The term "mimetic" refers to a molecule, the structure of which is developed from knowledge of the structure of the RET16 protein, or portions thereof, and as such, is able to effect some or all of the actions of the RET16 protein.

The term "portion" with regard to a protein (as in "a portion of a given protein") refers to fragments or segments, for example, peptides, of that protein. The fragments can range in size from four or five amino acid residues to the entire amino acid sequence minus one amino acid. Thus, a protein "comprising at least a portion of the amino acid sequence of SEQ ID NO: 2 or SEQ ID NO:4" can encompass the full-length human RET16 polypeptide, and fragments or segments of full-length RET16.

The term antibody refers to intact molecules as well as fragments thereof, such as Fab, F(ab')$_2$, Fv, which are capable of binding an epitopic or antigenic determinant. Antibodies that bind to RET16 polypeptides can be prepared using intact polypeptides or fragments containing small peptides of interest or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include bovine serum albumin (BSA), keyhole limpet hemocyanin (KLH), and thyroglobulin. The coupled peptide is then used to immunize the animal (e.g, a mouse, a rat, or a rabbit).

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen et al.

The term "antigenic determinant" refers to that portion of a molecule that makes contact with a particular antibody (i.e., an epitope). When a protein or fragment of a protein is used to immunize a host animal, numerous regions of the protein can induce the production of antibodies which bind specifically to a given region or three-dimensional structure on the protein; these regions or structures are referred to an antigenic determinants. An antigenic determinant can compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (e.g., an antigenic determinant or epitope, or a structural determinant) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The term "correlates with expression of a polynucleotide" indicates that the detection of the presence of ribonucleic acid that is similar to SEQ ID NO:1 or SEQ ID NO:2 by Northern analysis is indicative of the presence of mRNA encoding the RET16 polypeptide in a sample and thereby correlates with expression of the transcript from the polynucleotide encoding the protein.

An alteration in the polynucleotide of SEQ ID NO:1 or SEQ ID NO:2 comprises any alteration in the sequence of the polynucleotides encoding the RET16 polypeptide, including deletions, insertions, and point mutations that can be detected using hybridization assays. Included within this definition is the detection of alterations to the genomic DNA sequence which encodes the RET16 polypeptide (e.g., by alterations in the pattern of restriction fragment length polymorphisms capable of hybridizing to SEQ ID NO:1 or SEQ ID NO:3), the inability of a selected fragment of SEQ ID NO:1 or SEQ ID NO:3 to hybridize to a sample of genomic DNA (e.g., using allele-specific oligonucleotide probes), and improper or unexpected hybridization, such as hybridization to a locus other than the normal chromosomal locus for the polynucleotide sequence encoding the RET16 polypeptide (e.g., using fluorescent in situ hybridization (FISH) to metaphase chromosome spreads).

DESCRIPTION OF THE PRESENT INVENTION

The present invention relates to RET16 polynucleotides and encoded polypeptides. Specifically described herein are RET16 (also called RET16.1 herein) and variants RET16.2 and RET16.3. All references to "RET16" shall be construed to apply to RET16 (RET16.1), RET16.2 and RET16.3, unless otherwise specified herein.

The novel RET16 gene described herein was discovered to be expressed and upregulated in TNF-stimulated human lung microvascular endothelial cells. In accordance with the present invention, RNA expressed in TNF-stimulated human lung microvascular endothelial cells was analyzed to identify gene products that were likely to be involved in cellular regulatory events. Resting cells were stimulated for 1 hour with TNF-alpha, and the RNA was isolated from the cells. Complementary DNA (cDNA) was produced from the isolated RNA employing conventional procedures known and used by those having skill in the art. The cDNAs that were upregulated following TNF-alpha stimulation of the microvascular endothelial cells were identified using subtractive hybridization. (See Example 1). Polynucleotide cDNAs identified via this approach were assessed for potential roles in the signaling cascade as discussed below.

Accordingly, the role of the RET16 gene described herein was characterized using an antisense strategy (Examples 5 and 6). Toward this end, cells were transfected with antisense oligonucleotides and stimulated with TNF-alpha. The antisense oligonucleotide that were capable of inhibiting RET16 RNA were evaluated to select an oligo capable of blocking RNA expression. The most active RET16 gene antisense was found to be the 11587 oligo having the following sequence:
UGCACAUGCCGCCMGGAGCCAUCU (SEQ ID NO:16).

The 11587 oligo inhibited the upregulation of E-selectin protein on the surface of transfected cells, thus suggesting a role for RET16 in the cell signaling cascade. (Example 6 and FIG. 9). Reduction of the RNA level of the RET16 gene is presumed to reduce the level of the RET16 protein in the cell. Consequently, reducing the level of RET16 protein in the cell was able to interfere with the TNF-alpha signaling cascade, resulting in the decreased expression of E-selectin on the cell surface.

Figure 9:
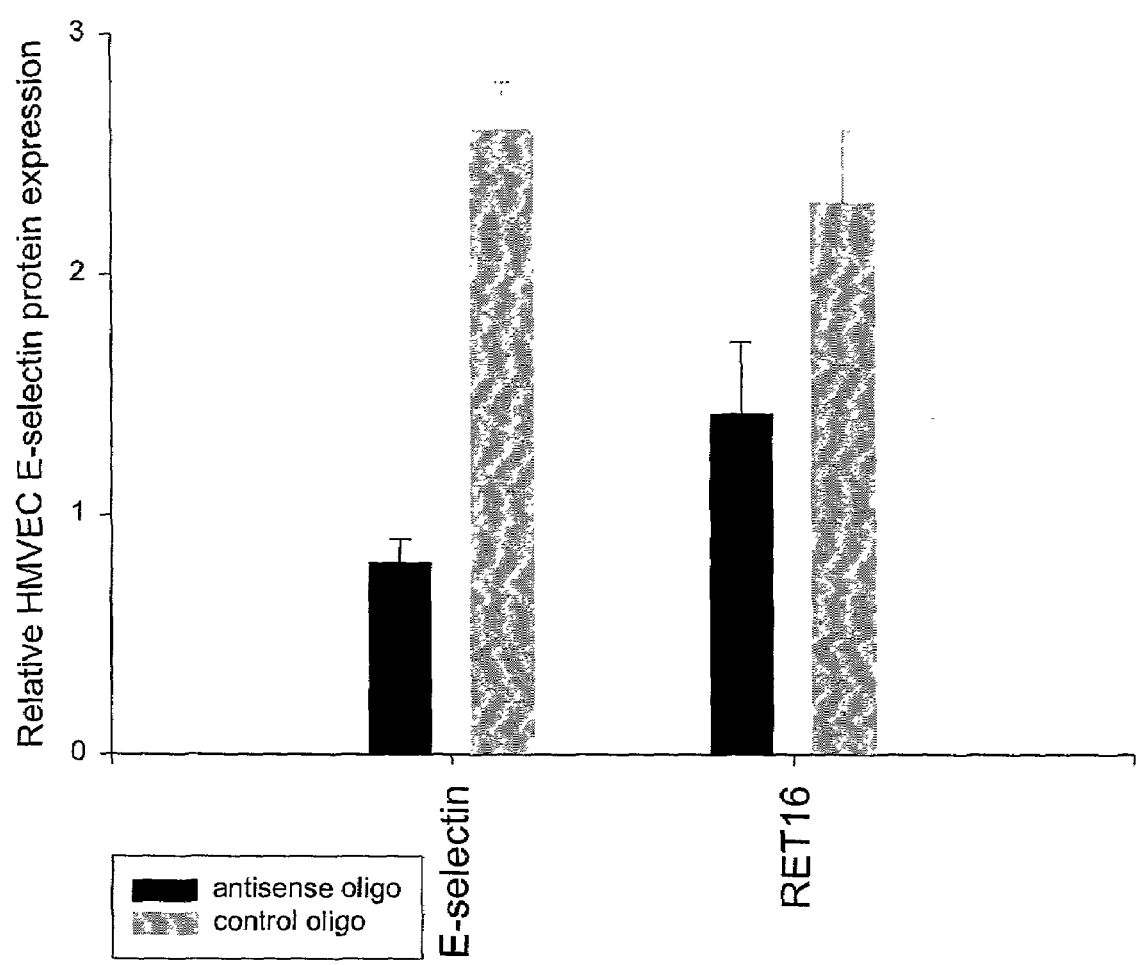
FIG. 9 presents the results of studies performed to determine the inhibition of E-selectin protein expression on TNF-stimulated HMVEC cells by transfection of antisense E-selectin and antisense RET16 oligonucleotides. The cells were transfected with the antisense or control oligonucleotides as described in Example 6. The cells were then stimulated for six hours with TNF-alpha and the cell surface expression of E-selectin was determined by an ELISA assay. (See Example 6).

As described in Example 6 and shown in FIG. 9, antisense oligonucleotides directed against the RET16 polynucleotide resulted in significant inhibition of E-selectin expression in TNF-stimulated HMVEC cells. These results imply that RET16 at least modulates E-selectin expression, either directly or indirectly. Preferably, the results indicate that RET16 represents a positive modulator of E-selectin, which is associated with a number of inflammatory disorders known in the art. Thus, antagonists of RET16 are useful for the treatment, prevention, and/or amelioration of inflammatory disorders, as discussed further herein.

Moreover, according to the present invention, antisense oligonucleotides directed against RET16 also resulted in inhibition of V-cam expression. These results imply that RET16 also at least modulates V-cam expression, either directly or indirectly. Preferably, the results indicate that RET16 represents a positive modulator of V-cam, as well.

E-selectin represents a positive marker for inflammatory conditions (D. J. Lefer, 2000, *Annu, Rev, Pharmacol, Toxicol.*, 40:283–94; A. Blann and M. Seigneur, 1997, *Clin. Hemorheol, Microcirc.*, 17(1):3–11) with increased E-selectin being expressed on the extracellular membrane of a variety of cells and tissue cell types. This association is mediated through the role of E-selectin in modulating cellular rolling of circulating leukocytes on vascular endothelial cells. The expression of soluble forms of E-selectin and v-cam have also been associated with inflammatory disorders (A. J. Gearing and W. Newman, 1993, *Immunol, Today*, 14(10):506–12). Recent studies have shown E-selectin and V-cam expression to be associated with the incidence of asthma, and particularly with the incidence of severe asthma (A. Hamzaoui et al., 2001, *Am. J. Inflamm.*, 10(6):339–42).

In addition, E-selectin has been shown to be associated with the incidence of juvenile idiopathic arthritis (C. Y. Chen et al., 2002, *Ann. Rheum, Dis.*, 61(2):167–70). E-selectin has also been associated with the incidence of hematogenous metastases of tumor cells (K. Ito et al., 2001, *J. Gastroenterol.*, 36(12):823–9); E-selectin has been associated with the incidence of hyperinsulinaemia and diabetes type 2 (B. R. Winkelmann et al., 2001, *Curr. Med. Res. Opin.*, 17(2): 132–41; and G. Targher et al., 2001, *Diabetes Care*, 24(11): 1961–6); E-selectin has been associated with the incidence of atherosclerosis and cardiovascular disease (E. Demerath et al., 2001, *Ann. Hum. Biol.*, 28(6):664–78); E-selectin and V-cam have been associated with the incidence of tumor progression and metastasis, in general, and particularly for colon cancer (D. Alexiou et al., 2001, *Eur. J. Cancer*, 37(18):2392–7); E-selectin has been associated with the incidence of Wegener's granulomatosis (N. Ohta et al., 2001, *Auris. Nasus. Larynx.*, 28(4):311–4); E-selectin and V-cam have been associated with the incidence of stem cell transplantation complications (Y. Matsuda et al., 2001, *Bone Marrow Transplant.*, 27(9):977–82); E-selectin and V-cam have been associated with the incidence of thalassemia (D. S. Kyriakou et al., 2001, *Ann. Hematol.*, 80(10):577–83); E-selectin has been associated with the incidence of atherosclerosis (C. M. Ballantyne, 2001, *Clin. Cardiol.*, 24(8 Suppl):III13–7); E-selectin has been associated with the incidence of autoimmune disease (R. W. McMurray, 1996, *Semin. Arthritis. Rheum.*, 25(4):215–33); E-selectin has been associated with the incidence of atherosclerosis, ischemia-reperfusion injury, acute lung injury, rheumatoid arthritis, and graft rejection (M. P. Bevilacqua et al., 1994, *Ann. Rev. Med.*, 45:361–78); and E-selectin has been associated with the incidence of allergic inflammation (C. H. Smith et al., 1993, *Am. Rev. Respir. Dis.*, 148(6 Pt 2):S75–8). Thus, RET16 polynucleotides and polypeptides, including fragments or antagonists of RET16, are useful for the treatment, prevention, and/or amelioration of any of the foregoing disorders.

Polymorphic forms of E-selectin have also been associated with several diseases and disorders. For example, the A561C E-selectin polymorphism has been associated with systemic lupus erythematosus (Magadmi et al., 2001, *J.*

*Rheumatol.*, 28(12):2650–2); the E-selectin S128R polymorphism has been associated with coronary artery calcification (D. L. Ellsworth et al., 2001, *J. Mol. Med.*, 79(7): 390–8); and additional E-selectin polymorphisms have been associated with the incidence of ischaemic heart conditions (F. Andreotti et al., 2002, *Heart.*, 87(2):107–12). Thus, RET16 polynucleotides and polypeptides, including fragments or antagonists of RET16, are useful for the treatment, prevention, and/or amelioration of any of the foregoing disorders.

Figure 10E:
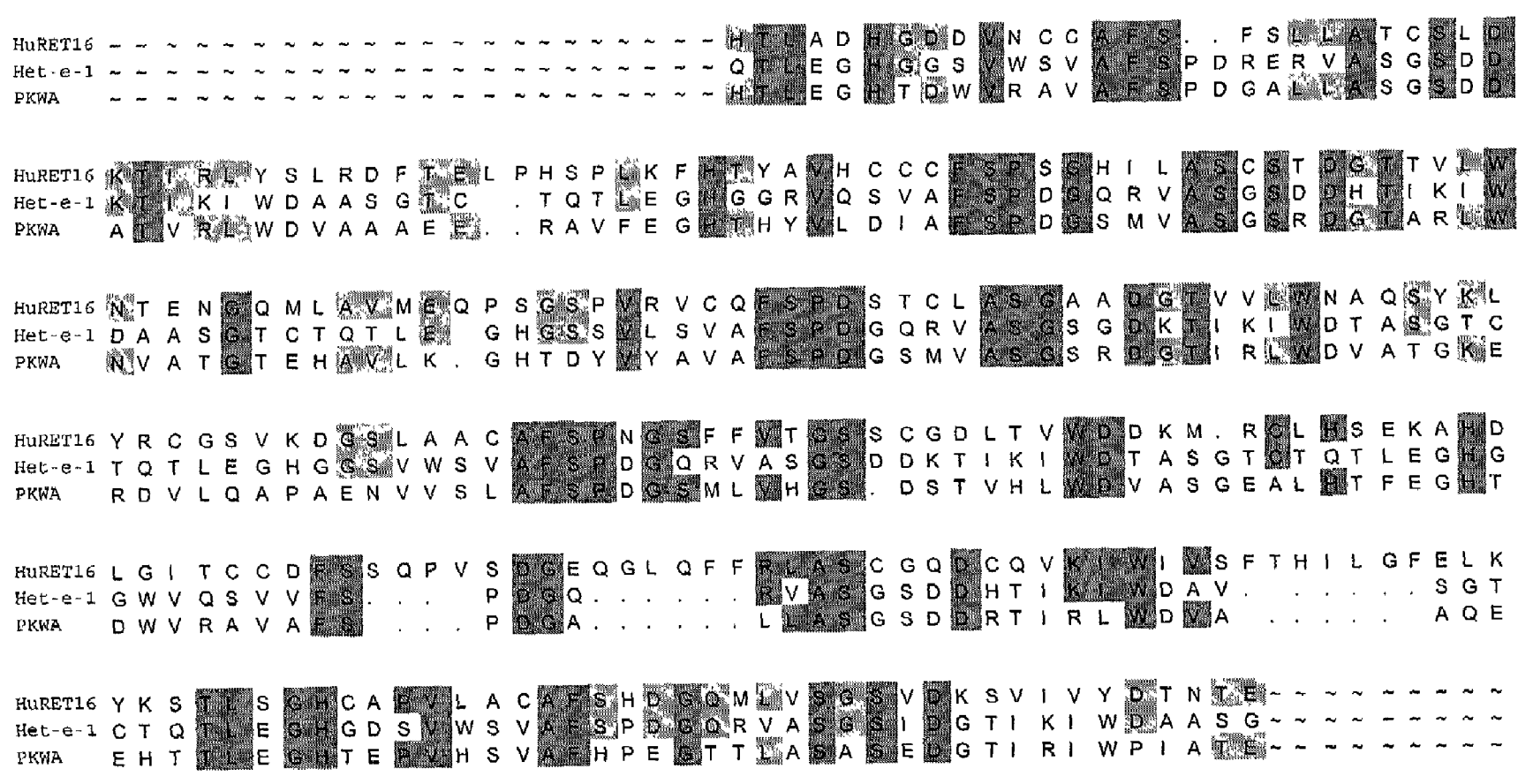

In one of its embodiments, the present invention is directed to a human RET16 polypeptide comprising the amino acid sequence of SEQ ID NO:2 as shown in FIGS. 2 and 3, or SEQ ID NO:4, as shown in FIG. 4B. The RET16 polypeptide product is 476 amino acids in length (SEQ ID NO:2, FIG. 2). The human RET16 polypeptide shares 31% identity with a portion of *Podospora anserina* Het-e-1 protein and 33% identity with a portion of *Thermomonospora curvata* PKWA protein as shown in FIG. 10E. In addition, full-length mouse and partial rat orthologs of human RET16 were identified as described herein. For example, FIGS. 5 and 6 provide the nucleic acid sequence (SEQ ID NO:6) and the encoded amino acid sequence (SEQ ID NO:7), respectively, of the murine RET16 ortholog. FIG. 13 provides the nucleic acid sequence (SEQ ID NO:8) of the partial rat RET16 ortholog and FIG. 14 shows the encoded amino acid sequence (SEQ ID NO:9) of the partial rat RET16 ortholog.

The RET16 amino acid sequence was found to contain several sequence motifs common to other known proteins using the MOTIFS program in SEQWEB GCG. MOTIFS looks for protein motifs by searching protein sequences for regular-expression patterns described in the PROSITE Dictionary. The RET16 amino acid sequence contains 3 potential asparagine glycosylation sites at amino acids positions 150, 365, 460. In addition, the RET16 amino acid sequence contains potential cyclic adenosine monophosphate (amino acids 441 and 442), casein kinase II (amino acids 7, 38, 136, 159, 164, 184, 194, 268, 333, and 370), and protein kinase C (amino acids 33, 38, 128, 136, 175, 439, 462) phosphorylation sites.

The RET16 amino acid sequence was used to search the PFAM-HMM database for other protein domains. The PFAM-HMM database is a collection of protein families and domains and contains multiple protein alignments (A. Bateman et al., 1999, *Nucleic Acids Research*, 27:260–262). Seven potential WD40, beta-transducin (G-beta) repeats were identified, in addition to one sterile alpha motif (SAM) domain (FIG. 17).

Beta-transducin (G-beta) is one of the three subunits (alpha, beta, and gamma) of the guanine nucleotide-binding proteins (G proteins) which act as intermediaries in the transduction of signals generated by transmembrane receptors. Structurally G-beta consists of eight tandem repeats of about 40 residues, each containing a central Trp-Asp motif (this type of repeat is sometimes called a WD-40 repeat). Such a repetitive segment has been shown to exist in a number of other proteins, including G-beta-like peptides, yeast STE4, MSI1, CDC4, CDC20, MAK11, PRP4, PWP1 and TUP1, slime-mould AAC3 and coronin, and *Drosophila* Groucho protein. The number of repeats within these proteins varies between 5 (PRP4, TUP1, and Groucho) and 8 (G-beta, STE4, MSI1, AAC3, CDC4, PWP1, etc.). In G-beta and G-beta-like proteins, the repeats span the entire length of the sequence, while in other proteins, the repeats comprise the N-terminal, the central, or the C-terminal section. (E. J. Neer et al., 1994, *Nature*, 371:297–300).

The sterile alpha motif (SAM) domain is a putative protein interaction module present in a wide variety of proteins involved in many biological processes. The SAM domain of approximately 70 residues is found in diverse eukaryotic organisms. SAM domains have been shown to homo- and hetero-oligomerize, but with a low binding affinity, and to mediate specific protein-protein interactions. Structural analyses show that the SAM domain is arranged in a small five-helix bundle with two large interfaces. In the case of the SAM domain of the Eph tyrosine kinase EphB2, each of these interfaces is able to form dimers. The presence of these two distinct binding surfaces suggests that SAM domains could form extended polymeric structures (D. Stapleton et al., 1999, *Nature Struct. Biol.*, 6:44–49).

The Incyte Genomics Lifeseq Gold database was used to perform preliminary expression analysis of RET16. According to the electronic Northern in the Incyte database (Template ID 158923.9; Clone ID 3111127), the RET16 gene sequence was identified in 56 cDNA libraries. These libraries which were found to express the RET16 gene are shown in FIG. 12. Of special interest, RET16 was found to be expressed in several tumor tissues, including those from kidney, prostate, pituitary, esophagus, ovary, urinary bladder, lung, colon, paraganglion, adrenal, liver, uterus, and pancreas tissue. In addition, RET16 was found to be expressed in tissues from the following disease states: Huntington's disease, leukemia, cholelithisis, epilepsy, chronic ulcerative colitis, Alzheimer's disease, and lymphocytic thyroiditis. Of particular note, RET16 was found to be expressed in bronchial epithelial cells treated with 20% smoke for 20 hours, CD4+T-lymphocytes treated with CD3 antibodies, a K-562 chronic myelogenous leukemia precursor line treated with 1 μM 5-aza-2'deoxycytidine for 72 hours, and umbilical cord mononuclear cells treated with IL-5.

Another embodiment of the present invention encompasses a murine ortholog, i.e., muRET16, of the human RET16 (huRET6) gene. To identify the murine ortholog of huRET16, the coding sequence of huRET16 was used to search the mouse EST database, available to those in the art for performing the basic local alignment search tool (BLAST) analyses. The following murine EST's were identified: AU035693, AA118718, AA204608, W41056, AW146018, Al450495, Al875443, Al316544, AW494796, AW146018 and BE983890. The muRET16 nucleic acid sequence (SEQ ID NO:6) has 80% identity with huRET16. The encoded muRET16 amino acid sequence (SEQ ID NO:7) is 82.5% identical to huRET16 (86.5% similarity). MuRET16 has 7 predicted WD repeats and 1 SAM domain, all having a score of >10.

The carboxyl terminus of RET16 contains a U box domain, as determined based upon a Hidden Markov Model E value of 1.78e-23. The homology of the RET16 U box domain with the U box of protein PRP19 (S.C. Cheng et al., 1993, *Mol. Cell. Biol.*, 13(3):1876–82) and the alignment of consensus residues is shown in FIG. 21 (conserved residue annotation modified from Aravind and Koonin, 2001, *Current Biology*, 10(4):R132–R134. PRP 19, is a pre-mRNA splicing factor that, in addition to the U box, contains WD40 repeats.

The U box domain-containing proteins typified by UFD2 mediate E3 ubiquitin conjugation reactions (Aravind and Koonin, Ibid). E3 ubiquitin ligases participate in the transfer of ubiquitin from an E2 ubiquitin ligase onto a substrate protein. Recent publications have provided strong evidence for the ubiquitin ligase activity of a series of U box-containing proteins (see, e.g., Hatakeyama et al., 2001, *J.*

*Biol. Chem.*, 276(35):33111–33120; Murata et al., 2001, *EMBO*, 21(121):1133–1138; Meachem et al., 2001, *Nature Cell Biology*, 3:100–105; and Pringa et al., 2001, *J. Biol. Chem.*, 276(22):19617–19623). In a reconstitution assay, the U box-containing protein provided E3 ubiquitin ligase activity in the presence of E1 and E2 ubiquitin ligases. In addition, deletion of the U box, or mutation of key conserved residues in the U box protein, abrogated the ubiquitin ligase activity. (Hatakeyama et al., 2001, Ibid.) The U box ubiquitin ligases are structurally distinct from HECT or RING finger E3s, and can be distinguished functionally by the ability to catalyze polyubiquitination of substrate proteins.

Multiple key regulatory proteins in the cell are modified by the addition of ubiquitin. Proteosomal degradation of ubiquitinated proteins controls a number of cellular events such as the cell cycle, differentiation, immune responses and clearance of misfolded proteins. In view of its U box domain, which is a feature of proteins that mediate ubiquitination, in particular, E3 ubiquitin conjugation reactions, RET16 is characterized as a ubiquitin ligase.

To determine E3 ubiquitin ligase activity, assays can be performed as described in Hatakeyama et al., 2001, Ibid., Murata et al. 2001, Ibid. and Meachem et al., 2001, Ibid.). Site directed mutagenesis can be used to identify those amino acids in a ubiquitin ligase protein that are necessary for ubiquitin ligase activity. In addition, deletion of all or a portions of the U box can be performed to confirm the role of the U box in mediating ubiquitin ligase activity. A polynucleotide encoding RET16 containing a deleted or mutated U box can be transfected into cells to reveal the functional role of expressed RET16 protein intracellularly. This same approach is amenable for isolating and identifying cellular substrate(s) for the ubiquitin ligases.

RET16 Polynucleotides and Polypeptides

The present invention encompasses a human RET16 nucleic acid sequence (SEQ ID NO:1 or SEQ ID NO:3) encoding the RET16 polypeptide (SEQ ID NO:2 or SEQ ID NO:4, respectively) and the use of the RET16 polynucleotides, polypeptides, or compositions thereof, in methods for screening for antagonists or inhibitors of the interaction of RET16 with other cellular signaling components involved generally in inflammatory processes, cell activation, or uncontrolled cell growth, and specifically in TNF-activated endothelium.

This invention further embraces an isolated nucleic acid or polypeptide molecule that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a RET16 nucleic acid sequence or amino acid sequence according to the present invention. More specifically, the invention encompasses an isolated polynucleotide, or fragment thereof, having a nucleotide sequence that is at least 82.0% identical to the sequence of SEQ ID NO:12; an isolated polynucleotide, or fragment thereof, having a nucleotide sequence that is at least 68.2% identical to the sequence of SEQ ID NO:12; and an isolated polynucleotide, or fragment thereof, having a nucleotide sequence that is at least 93.1% identical to the sequence of SEQ ID NO:14. In addition, the present invention encompasses an isolated polynucleotide, or fragment thereof, encoding an amino acid sequence of a cell signaling polypeptide, where the polypeptide has at least 82% sequence identity to the sequence of SEQ ID NO:13; and an isolated polynucleotide, or fragment thereof, encoding an amino acid sequence of a cell signaling polypeptide, where the polypeptide has at least 95.0% sequence identity with the sequence of SEQ ID NO:15. The invention further encompasses an isolated and/or substantially purified cell signaling protein having an amino acid sequence that has at least 82% sequence identity with the sequence as set forth in SEQ ID NO:13; and an isolated and/or substantially purified cell signaling protein having an amino acid sequence that has at least 95% sequence identity with the sequence as set forth in SEQ ID NO:15.

Also encompassed by the invention is the use of the RET16 nucleic acid sequence and the RET16 polypeptide, or molecules that interact with all or a portion of the RET16 nucleic acid or amino acid sequence in methods for diagnosing, treating or preventing disorders or diseases associated with inflammation and cellular inflammatory processes or with cell growth or cell activation processes. In addition, the RET16 gene and polypeptide are useful for determining those cellular signaling molecules that associate with RET16 and which provide critical signals for the signaling cascade that can be involved with the master switch related to the development of inflammatory processes or intracellular signaling events triggered by receptor activation, stimulation, or uncontrolled cell growth.

According to the present invention, nucleic acid encoding human RET16 protein was first identified in a subtraction cDNA library from TNF-alpha-stimulated human lung microvascular endothelial cells. The full-length RET16 gene was isolated by extending clone sequences available from the Incyte and public EST databases, as described in Example 1.

In one of its embodiments, the present invention encompasses a polypeptide comprising the amino acid sequence of SEQ ID NO:2 as shown in FIGS. 2 and 3 and the open reading frame amino acid sequence of SEQ ID NO:4 as shown in FIG. 4B. The human RET16 polypeptide is 476 amino acids in length. FIGS. 10A–10E portray the structural similarities among RET16 and several other proteins, namely a portion of *Podospora anserina* vegetable incompatibility protein Het-E-1; a portion of *Thermomonospora curvata* putative serine/threonine-protein kinase PWKA; the RET16 murine ortholog, and the partial RET16 rat ortholog.

Variants of the RET16 polypeptide are also encompassed by the present invention. In one aspect, a RET16 variant has at least 75 to 80%, preferably at least 85 to 90%, and more preferably at least 90% amino acid sequence identity to the amino acid sequence (SEQ ID NO:2 or SEQ ID NO:4) disclosed herein, and which retains at least one biological, immunological, or other functional characteristic or activity of the RET16 polypeptide. Most preferred is a variant having at least 95% amino acid sequence identity to the amino acid sequence set forth in SEQ ID NO:2 or SEQ ID NO:4. An amino acid sequence variant of the RET16 protein can be categorized into one or more of three classes: substitutional, insertional, or deletional variants. Such variants are typically prepared by site-specific mutagenesis of nucleotides in the DNA encoding the RET16 protein, using cassette or PCR mutagenesis, or other techniques that are well known and practiced in the art, to produce DNA encoding the variant. Thereafter, the DNA is expressed in recombinant cell culture as described herein. Variant RET16 protein fragments having up to about 100–150 residues can be prepared by in vitro synthesis using conventional techniques.

Figure 18:
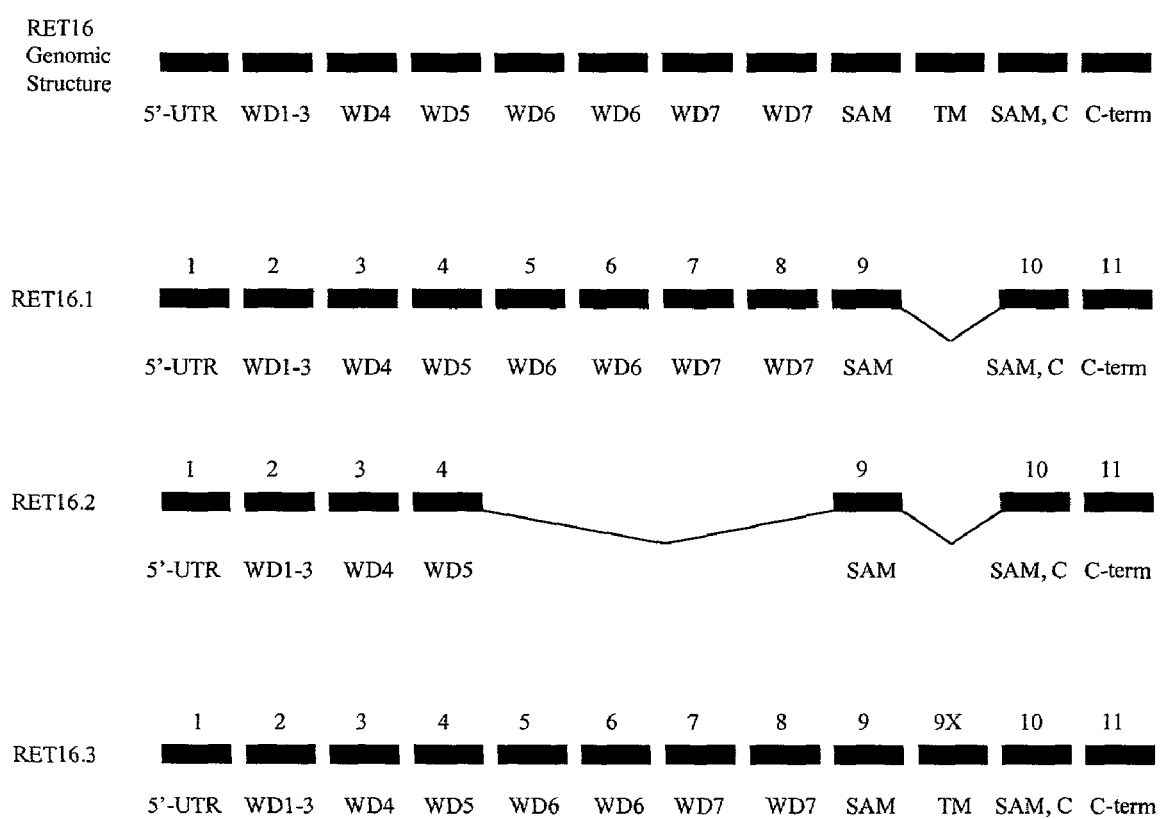
FIG. 18 shows the exon structures of human RET16 (also called RET16.1 herein), and the RET16.2 and RET16.3 splice variants.

Two variants, RET16.2 and RET16.3 are described herein (see, Example 2; FIG. 16—multiple sequence alignments; FIG. 18—exon structure; FIGS. 19A and 19B, polynucleotide sequence (SEQ ID NO:12) and amino acid sequence (SEQ ID NO:13), respectively, of variant RET16.2; and FIGS. 20A and 20B, polynucleotide sequence (SEQ ID NO:14) and amino acid sequence (SEQ ID NO:15), respectively, of variant RET16.3).

Amino acid sequence variants are characterized by the predetermined nature of the variation, a feature that sets them apart from naturally occurring allelic or interspecies variations of the RET16 protein amino acid sequence. The variants typically exhibit the same qualitative biological activity as that of the naturally occurring analogue, although variants can also be selected having modified characteristics. While the site or region for introducing an amino acid sequence variation is predetermined, the mutation per se need not be predetermined. For example, in order to optimize the performance of a mutation at a given site, random mutagenesis can be performed at the target codon or region, and the expressed RET16 variants screened for the optimal combination of desired activity. Techniques for making substitution mutations at predetermined sites in DNA having a known sequence are well known, for example, M13 primer mutagenesis and PCR mutagenesis. Screening of the mutants is accomplished using assays of RET16 protein activities, for example, for binding domain mutations, competitive binding studies can be carried out.

Amino acid substitutions are typically of single residues; insertions usually are on the order of from one to twenty amino acids, although considerably larger insertions can be tolerated. Deletions range from about one to about 20 residues, although in some cases, deletions can be much larger.

Substitutions, deletions, insertions, or any combination thereof, can be used to arrive at a final RET16 derivative. Generally, these changes affect only a few amino acids to minimize the alteration of the molecule. However, larger changes can be tolerated in certain circumstances. When small alterations in the characteristics of the RET16 protein are desired or warranted, substitutions are generally made in accordance with the following Table 1:

TABLE 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 1. For example, substitutions can be made which more significantly affect the structure of the polypeptide backbone in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) a residue that does not have a side chain, e.g., glycine.

While RET16 variants will ordinarily exhibit the same qualitative biological activity or function, and elicit the same immune response, as the naturally occurring analogue, the variants are also selected to modify the characteristics of the RET16 protein as needed. Alternatively, the variant can be designed such the that biological activity of the RET16 protein is altered.

In another embodiment, the present invention encompasses polynucleotides which encode the RET16 polypeptide. Accordingly, any nucleic acid sequence which encodes the amino acid sequence of the RET16 polypeptide can be used to produce recombinant molecules that express RET16 protein. In a particular embodiment, the present invention encompasses the RET16 polynucleotide comprising the nucleic acid sequence of SEQ ID NO:1 and SEQ ID NO:3, as shown in FIGS. 1 and 4A, respectively, and the murine ortholog of human RET16 comprising the nucleic acid sequence of SEQ ID NO:6, as well as the rat ortholog of human RET16 comprising the nucleic acid sequence of SEQ ID NO:8. More particularly, the present invention provides cloned full-length open reading frame human RET16 cDNA (1532 bp), (also called RET16.1) deposited at the American Type Culture Collection (ATCC), 10801 University Boulevard, Manassas, Va. 20110-2209 on Mar. 7, 2001 under ATCC Accession No. PTA-3161 according to the terms of the Budapest Treaty.

In a preferred embodiment, the present invention encompasses a polynucleotide lacking the initiating start codon, in addition to the resulting encoded polypeptide of RET16.1. Specifically, the present invention encompasses the polynucleotide corresponding to nucleotides 151 through 1575 of SEQ ID NO:1, and the polypeptide corresponding to amino acids 2 through 476 of SEQ ID NO:2. Also encompassed are recombinant vectors comprising the RET16.1 encoding sequence, and host cells comprising the vector as described herein.

In another preferred embodiment, the present invention encompasses a polynucleotide lacking the initiating start codon, in addition to the resulting encoded polypeptide of RET16.2. Specifically, the present invention encompasses the polynucleotide corresponding to nucleotides 114 through 1262 of SEQ ID NO:12, and the polypeptide corresponding to amino acids 2 through 384 of SEQ ID NO:13. Also encompassed are recombinant vectors comprising the RET16.2 encoding sequence, and host cells comprising the vector as described herein.

In another preferred embodiment, the present invention encompasses a polynucleotide lacking the initiating start codon, in addition to the resulting encoded polypeptide of RET16.3. Specifically, the present invention encompasses the polynucleotide corresponding to nucleotides 139 through 1641 of SEQ ID NO:14, and the polypeptide corresponding to amino acids 2 through 502 of SEQ ID NO:15. Also encompassed are recombinant vectors comprising the RET16.3 encoding sequence, and host cells comprising the vector as described herein.

In another preferred embodiment, the present invention encompasses a polynucleotide lacking the initiating start codon, in addition to the resulting encoded polypeptide of the mouse RET16. Specifically, the present invention encompasses the polynucleotide corresponding to nucleotides 19 through 1443 of SEQ ID NO:6, and the polypeptide corresponding to amino acids 2 through 475 of SEQ ID NO:7. Also encompassed are recombinant vectors comprising the mouse RET16 encoding sequence, and host cells comprising the vector as described herein.

As will be appreciated by the skilled practitioner in the art, the degeneracy of the genetic code results in the production of numerous nucleotide sequences encoding the RET16 polypeptide of the present invention. Some of the sequences bear minimal homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of naturally occurring RET16, and all such variations are to be considered as being specifically disclosed.

Although nucleotide sequences which encode the RET16 polypeptide and its variants are preferably capable of hybridizing to the nucleotide sequence of the naturally occurring RET16 polypeptide under appropriately selected conditions of stringency, it may be advantageous to produce nucleotide sequences encoding the RET16 polypeptide, or its derivatives, which possess a substantially different codon usage. Codons can be selected to increase the rate at which expression of the peptide/polypeptide occurs in a particular prokaryotic or eukaryotic host in accordance with the frequency with which particular codons are utilized by the host, for example, in plant cells or yeast cells or amphibian cells. Other reasons for substantially altering the nucleotide sequence encoding the RET16 polypeptide, and its derivatives, without altering the encoded amino acid sequences include the production of mRNA transcripts having more desirable properties, such as a greater half-life, than transcripts produced from the naturally occurring sequence.

The present invention also encompasses production of DNA sequences, or portions thereof, which encode the RET16 polypeptide, and its derivatives, entirely by synthetic chemistry. After production, the synthetic sequence can be inserted into any of the many available expression vectors and cell systems using reagents that are well known and practiced by those in the art. Moreover, synthetic chemistry can be used to introduce mutations into a sequence encoding RET16 polypeptide, or any fragment thereof.

Also encompassed by the present invention are polynucleotide sequences that are capable of hybridizing to the claimed nucleotide sequence of RET16, such as that shown in SEQ ID NO:1 or SEQ ID NO:3, under various conditions of stringency. Hybridization conditions are typically based on the melting temperature (Tm) of the nucleic acid binding complex or probe (See, G. M. Wahl and S. L. Berger, 1987; *Methods Enzymol.,* 152:399–407 and A. R. Kimmel, 1987; *Methods of Enzymol.,* 152:507–511), and can be used at a defined stringency. For example, included in the present invention are sequences capable of hybridizing under moderately stringent conditions to the RET16 nucleic acid sequence of SEQ ID NO:1 or SEQ ID NO:3 and other sequences which are degenerate to those which encode the RET16 polypeptide (e.g., as a nonlimiting example: pre-washing solution of 2×SSC, 0.5% SDS, 1.0 mM EDTA, pH 8.0, and hybridization conditions of 50° C., 5×SSC, overnight).

In another embodiment of the present invention, polynucleotide sequences or fragments (peptides) thereof which encode the RET16 polypeptide can be used in recombinant DNA molecules to direct the expression of the RET16 polypeptide product, or fragments or functional equivalents thereof, in appropriate host cells. Because of the inherent degeneracy of the genetic code, other DNA sequences, which encode substantially the same or a functionally equivalent amino acid sequence, can be produced and these sequences can be used to express RET16 protein.

As will be appreciated by those having skill in the art, it may be advantageous to produce RET16 polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequence of the present invention can be engineered using methods generally known in the art in order to alter RET16 polypeptide-encoding sequences for a variety of reasons, including, but not limited to, alterations which modify the cloning, processing, and/or expression of the gene product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, or introduce mutations, and the like.

In another embodiment of the present invention, natural, modified, or recombinant nucleic acid sequences, or a fragment thereof, encoding the RET16 polypeptide can be ligated to a heterologous sequence to encode a fusion protein. For example, for screening peptide libraries for inhibitors or modulators of RET16 activity or binding, it can be useful to encode a chimeric RET16 protein that can be recognized by a commercially available antibody. A fusion protein can also be engineered to contain a cleavage site located between the RET16 protein-encoding sequence and the heterologous protein sequence, so that the RET16 protein can be cleaved and purified away from the heterologous moiety.

Accordingly, the present invention encompasses a substantially purified cell signaling protein that is involved in the cell signaling cascade and is encoded by a polynucleotide having a nucleic acid sequence as set forth in SEQ ID NOS:1, 3, 5, 6, 8, 12, or 14 or a nucleic acid sequence degenerate from that of SEQ ID NOS:1, 3, 5, 6, 8, 12, or 14, as a result of redundancy of the genetic code. Such a fusion protein can further comprise all or a portion of the amino acid sequence of SEQ ID NOS:2, 4, 7, 9, 13, or 15, or an amino acid sequence having at least 80% sequence identity to the sequence as set forth in SEQ ID NOS:2, 4, 7, 9, 13, or 15, and an amino acid sequence of a second protein.

In another embodiment, ligand-binding assays are useful to identify inhibitor compounds that interfere with the function of the RET16 product, or activator compounds that stimulate the function of the RET16 protein. Such assays are useful even if the function of a protein is not known. These assays are designed to detect binding of test compounds to particular target molecules, e.g., proteins or peptides. The detection can involve direct measurement of binding. Alternatively, indirect indications of binding can involve stabilization of protein structure, or disruption or enhancement of a biological function. Non-limiting examples of useful ligand-binding assays are detailed below.

One useful method for the detection and isolation of binding proteins is the Biomolecular Interaction Assay (BIAcore) system developed by Pharmacia Biosensor and described in the manufacturer's protocol (LKB Pharmacia, Sweden). The BIAcore system uses an affinity purified anti-GST antibody to immobilize GST-fusion proteins onto a sensor chip. The sensor utilizes surface plasmon resonance, which is an optical phenomenon that detects changes in refractive indices. Accordingly, a protein of interest, e.g., the RET16 polypeptide, or fragment thereof, of the present invention, is coated onto a chip and test compounds are passed over the chip. Binding is detected by a change in the refractive index (surface plasmon resonance).

A different type of ligand-binding assay involves scintillation proximity assays (SPA), as described in U.S. Pat. No. 4,568,649. In a modification of this assay currently undergoing development, chaperonins are used to distinguish folded and unfolded proteins. A tagged protein is attached to SPA beads, and test compounds are added. The bead is then subjected to mild denaturing conditions, such as, for example, heat, exposure to SDS, and the like, and a purified labeled chaperonin is added. If a test compound has bound to a target protein, the labeled chaperonin will not bind; conversely, if no test compound has bound, the protein will undergo some degree of denaturation and the chaperonin will bind. In another type of ligand binding assay, proteins containing mitochondrial targeting signals are imported into isolated mitochondria in vitro (Hurt et al., 1985, *EMBO J.*, 4:2061–2068; Eilers and Schatz, 1986, *Nature*, 322:228–231). In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of test compounds. A test compound that binds to the target protein should inhibit its uptake into isolated mitochondria in vitro.

Another type of ligand-binding assay suitable for use according to the present invention is the yeast two-hybrid system (Fields and Song, 1989, *Nature*, 340:245–246). The yeast two-hybrid system takes advantage of the properties of the GAL4 protein of the yeast *S. cerevisiae*. The GAL4 protein is a transcriptional activator required for the expression of genes encoding enzymes involving the utilization of galactose. GAL4 protein consists of two separable and functionally essential domains: an N-terminal domain, which binds to specific DNA sequences (UASG); and a C-terminal domain containing acidic regions, which is necessary to activate transcription. The native GAL4 protein, containing both domains, is a potent activator of transcription when yeast cells are grown on galactose medium. The N-terminal domain binds to DNA in a sequence-specific manner but is unable to activate transcription. The C-terminal domain contains the activating regions but cannot activate transcription because it fails to be localized to UASG. In the two-hybrid system, a system of two hybrid proteins containing parts of GAL4: (1) a GAL4 DNA-binding domain fused to a protein 'X', and (2) a GAL4 activation region fused to a protein 'Y'. If X and Y can form a protein-protein complex and reconstitute proximity of the GAL4 domains, transcription of a gene regulated by UASG occurs. Creation of two hybrid proteins, each containing one of the interacting proteins X and Y, allows the activation region of UASG to be brought to its normal site of action.

The binding assay described in Fodor et al., 1991, *Science*, 251:767–773, which involves testing the binding affinity of test compounds for a plurality of defined polymers synthesized on a solid substrate, can also be useful. Compounds that bind to the RET16 polypeptide, or portions thereof, according to this invention are potentially useful as agents for use in therapeutic compositions.

In another embodiment, sequences encoding the RET16 polypeptide can be synthesized in whole, or in part, using chemical methods well known in the art (See, for example, M. H. Caruthers et al., 1980, *Nucl. Acids Res. Symp. Ser.*, 215–223 and T. Horn, T et al., 1980, *Nucl. Acids Res. Symp. Ser.*, 225–232). Alternatively, the protein itself can be produced using chemical methods to synthesize the amino acid sequence of the RET16 polypeptide, or a fragment or portion thereof. For example, peptide synthesis can be performed using various solid-phase techniques (J. Y. Roberge et al., 1995, *Science*, 269:202–204) and automated synthesis can be achieved, for example, using the ABI 431A Peptide Synthesizer (PE Biosystems).

The newly synthesized peptide can be substantially purified by preparative high performance liquid chromatography (e.g., T. Creighton, 1983, *Proteins, Structures and Molecular Principles*, WH Freeman and Co., New York, N.Y.), by reversed-phase high performance liquid chromatography, or other purification methods as are known in the art. The composition of the synthetic peptides can be confirmed by amino acid analysis or sequencing (e.g., the Edman degradation procedure; Creighton, supra). In addition, the amino acid sequence of the RET16 polypeptide or any portion thereof, can be altered during direct synthesis and/or combined using chemical methods with sequences from other proteins, or any part thereof, to produce a variant polypeptide.

Expression of Human RET16 Protein

To express a biologically active/functional RET16 polypeptide or peptide, the nucleotide sequences encoding the RET16 polypeptide, or functional equivalents, can be inserted into an appropriate expression vector, i.e., a vector which contains the necessary elements for the transcription and translation of the inserted coding sequence. Methods which are well known to and practiced by those skilled in the art can be used to construct expression vectors containing sequences encoding the RET16 polypeptide and appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vector/host systems can be utilized to contain and express sequences encoding the RET16 polypeptide. Such expression vector/host systems include, but are not limited to, microorganisms such as bacteria transformed with recombinant bacteriophage, plasmid, or cosmid DNA expression vectors; yeast or fungi transformed with yeast or fungal expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems. The host cell employed is not limiting to the present invention.

"Control elements" or "regulatory sequences" are those non-translated regions of the vector, e.g., enhancers, promoters, 5' and 3' untranslated regions, which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, La Jolla, Calif.) or PSPORT1 plasmid (Life Technologies), and the like, can be used. The baculovirus polyhedrin promoter can be used in insect cells. Promoters or enhancers derived from the genomes of plant cells (e.g., heat shock, RUBISCO; and storage protein genes), or from plant viruses (e.g., viral promoters or leader sequences), can be cloned into the vector. In mammalian cell systems, promoters from mammalian genes or from mammalian viruses are preferred. If it is necessary to generate a cell line that contains multiple copies of the sequence encoding RET16, vectors based on SV40 or EBV can be used with an appropriate selectable marker.

In bacterial systems, a number of expression vectors can be selected, depending upon the use intended for the expressed RET16 product. For example, when large quantities of expressed protein are needed for the induction of antibodies, vectors which direct high level expression of fusion proteins that are readily purified can be used. Such vectors include, but are not limited to, the multifunctional *E. coli* cloning and expression vectors such as BLUESCRIPT (Stratagene), in which the sequence encoding the RET16 polypeptide, or a peptide thereof, can be ligated into the vector in-frame with sequences for the amino-terminal Met and the subsequent 7 residues of β-galactosidase, so that a hybrid protein is produced; pIN vectors (See, G. Van Heeke and S. M. Schuster, 1989, *J. Biol. Chem.*, 264:5503–5509); and the like. pGEX vectors (Promega, Madison, Wis.) can also be used to express foreign polypeptides, as fusion proteins with glutathione S-transferase (GST). In general, such fusion proteins are soluble and can be easily purified from lysed cells by adsorption to glutathione-agarose beads followed by elution in the presence of free glutathione. Proteins made in such systems can be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH can be used. (For reviews, see F. M. Ausubel et al., supra, and Grant et al., 1987, *Methods Enzymol.*, 153:516–544).

Should plant expression vectors be desired and used, the expression of sequences encoding the RET16 polypeptide can be driven by any of a number of promoters. For example, viral promoters such as the 35S and 19S promoters of CaMV can be used alone or in combination with the omega leader sequence from TMV (N. Takamatsu, 1987, *EMBO J.*, 6:307–311). Alternatively, plant promoters such as the small subunit of RUBISCO, or heat shock promoters, can be used (G. Coruzzi et al., 1984, *EMBO J.*, 3:1671–1680; R. Broglie et al., 1984, *Science*, 224:838–843; and J. Winter et al., 1991, *Results Probl. Cell Differ.* 17:85–105). These constructs can be introduced into plant cells by direct DNA transformation or pathogen-mediated transfection. Such techniques are described in a number of generally available reviews (See, for example, S. Hobbs or L. E. Murry, In: McGraw Hill *Yearbook of Science and Technology* (1992) McGraw Hill, New York, N.Y.; pp. 191–196).

An insect system can also be used to express the RET16 polypeptide For example, in one such system, *Autographa californica* nuclear polyhedrosis virus (AcNPV) is used as a vector to express foreign genes in *Spodoptera frugiperda* cells or in Trichoplusia larvae. The sequences encoding the RET16 polypeptide can be cloned into a non-essential region of the virus such as the polyhedrin gene and placed under control of the polyhedrin promoter. Successful insertion of the RET16 polypeptide will render the polyhedrin gene inactive and produce recombinant virus lacking coat protein. The recombinant viruses can then be used to infect, for example, *S. frugiperda* cells or *Trichoplusia larvae* in which the RET16 polypeptide product can be expressed (E. K. Engelhard et al., 1994, *Proc. Nat. Acad. Sci.*, 91:3224–3227).

In mammalian host cells, a number of viral-based expression systems can be utilized. In cases where an adenovirus is used as an expression vector, sequences encoding the RET16 polypeptide can be ligated into an adenovirus transcription/ translation complex containing the late promoter and tripartite leader sequence. Insertion in a non-essential E1 or E3 region of the viral genome can be used to obtain a viable virus which is capable of expressing the RET16 polypeptide in infected host cells (J. Logan and T. Shenk, 1984, *Proc. Natl. Acad. Sci.*, 81:3655–3659). In addition, transcription enhancers, such as the Rous sarcoma virus (RSV) enhancer, can be used to increase expression in mammalian host cells.

Specific initiation signals can also be used to achieve more efficient translation of sequences encoding the RET16 polypeptide. Such signals include the ATG initiation codon and adjacent sequences. In cases where sequences encoding the RET16 polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals, including the ATG initiation codon, should be provided. Furthermore, the initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system that is used, such as those described in the literature (D. Scharf et al., 1994, *Results Probl. Cell Differ.*, 20:125–162).

Moreover, a host cell strain can be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein can also be used to facilitate correct insertion, folding and/or function. Different host cells having specific cellular machinery and characteristic mechanisms for such post-translational activities (e.g., COS, CHO, HeLa, MDCK, HEK293, and W138) are available from the American Type Culture Collection (ATCC), American Type Culture Collection (ATCC), 10801

University Boulevard, Manassas, Va. 20110-2209, and can be chosen to ensure the correct modification and processing of the foreign protein.

For long-term, high-yield production of recombinant proteins, stable expression is preferred. For example, cell lines which stably express the RET16 protein can be transformed using expression vectors which can contain viral origins of replication and/or endogenous expression elements and a selectable marker gene on the same, or on a separate, vector. Following the introduction of the vector, cells can be allowed to grow for 1–2 days in an enriched cell culture medium before they are switched to selective medium. The purpose of the selectable marker is to confer resistance to selection, and its presence allows the growth and recovery of cells which successfully express the introduced sequences. Resistant clones of stably transformed cells can be proliferated using tissue culture techniques appropriate to the cell type.

Any number of selection systems can be used to recover transformed cell lines. These include, but are not limited to, the Herpes Simplex Virus thymidine kinase (HSV TK), (M. Wigler et al., 1977, Cell, 11:223–32) and adenine phosphoribosyltransferase (I. Lowy et al., 1980, Cell, 22:817–23) genes which can be employed in tk⁻ or aprt⁻ cells, respectively. Also, anti-metabolite, antibiotic or herbicide resistance can be used as the basis for selection; for example, dhfr, which confers resistance to methotrexate (M. Wigler et al., 1980, Proc. Natl. Acad. Sci., 77:3567–70); npt, which confers resistance to the aminoglycosides neomycin and G-418 (F. Colbere-Garapin et al., 1981, J. Mol. Biol., 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, Proc. Natl. Acad. Sci., 85:8047–51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, Methods Mol. Biol., 55:121–131).

Although the presence/absence of marker gene expression suggests that the gene of interest is also present, the presence and expression of the desired gene of interest may need to be confirmed. For example, if the RET16 nucleic acid sequence polypeptide is inserted within a marker gene sequence, recombinant cells containing sequences encoding the RET16 polypeptide can be identified by the absence of marker gene function. Alternatively, a marker gene can be placed in tandem with a sequence encoding the RET16 polypeptide under the control of a single promoter. Expression of the marker gene in response to induction or selection usually indicates co-expression of the tandem gene.

Alternatively, host cells which contain the nucleic acid sequence encoding the RET16 polypeptide and which express the RET16 polypeptide product can be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

Preferably, the RET16 polypeptide is substantially purified after expression. RET16 proteins can be isolated or purified in a variety of ways known to and practiced by those having skill in the art, depending on what other components can be present in the sample. Standard purification methods include electrophoretic, molecular, immunological and chromatographic techniques, including, but not limited to, ion exchange, hydrophobic affinity and reverse phase HPLC chromatography, and chromatofocusing. For example, the RET16 protein can be purified using a standard anti-RET16 antibody column. Ultrafiltration and diafiltration techniques, in conjunction with protein concentration, are also useful. For general guidance in suitable purification techniques, see R. Scopes, 1982, Protein Purification, Springer-Verlag, NY. As will be understood by the skilled practitioner, the degree of purification necessary will vary depending on the intended use of the RET16 protein; in some instances, no purification will be necessary.

In addition to recombinant production, fragments of the RET16 polypeptide can be produced by direct peptide synthesis using solid-phase techniques (J. Merrifield, 1963, J. Am. Chem. Soc., 85:2149–2154). Protein synthesis can be performed using manual techniques or by automation. Automated synthesis can be achieved, for example, using ABI 431A Peptide Synthesizer (PE Biosystems). Various fragments of the RET16 polypeptide can be chemically synthesized separately and then combined using chemical methods to produce the full length molecule.

Detection of Human RET16 Polynucleotide

The presence of polynucleotide sequences encoding the RET16 polypeptide can be detected by DNA-DNA or DNA-RNA hybridization, or by amplification using probes or portions or fragments of polynucleotides encoding the RET16 polypeptide. Nucleic acid amplification based assays involve the use of oligonucleotides or oligomers, based on the sequences encoding the RET16 polypeptide, to detect transformants containing DNA or RNA encoding the RET16 polypeptide.

A wide variety of labels and conjugation techniques are known and employed by those skilled in the art and can be used in various nucleic acid and amino acid assays. Means for producing labeled hybridization or PCR probes for detecting sequences related to polynucleotides encoding the RET16 polypeptide include oligo-labeling, nick translation, end-labeling, or PCR amplification using a labeled nucleotide. Alternatively, the sequences encoding the RET16 polypeptide, or any portions or fragments thereof, can be cloned into a vector for the production of an mRNA probe. Such vectors are known in the art, are commercially available, and can be used to synthesize RNA probes in vitro by addition of an appropriate RNA polymerase, such as T7, T3, or SP(6) and labeled nucleotides. These procedures can be conducted using a variety of commercially available kits (e.g., Amersham Pharmacia Biotech, Promega and U.S. Biochemical Corp.). Suitable reporter molecules or labels which can be used include radionuclides, enzymes, fluorescent, chemiluminescent, or chromogenic agents, as well as substrates, cofactors, inhibitors, magnetic particles, and the like.

Human RET16 Polypeptide—Production, Detection, Isolation

Host cells transformed with nucleotide sequences encoding the RET16 protein, or fragments thereof, can be cultured under conditions suitable for the expression and recovery of the protein from cell culture. The protein produced by a recombinant cell can be secreted or contained intracellularly depending on the sequence and/or the vector used. As will be understood by those having skill in the art, expression vectors containing polynucleotides which encode the RET16 protein can be designed to contain signal sequences which direct secretion of the RET16 protein through a prokaryotic or eukaryotic cell membrane.

Other constructions can be used to join nucleic acid sequences encoding the RET16 protein to nucleotide sequence encoding a polypeptide domain which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the RET16 protein can be used to facilitate purification. One such expression vector provides for expression of a fusion protein containing RET16-encoding sequence and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263–281, while the enterokinase cleavage site provides a means for purifying from the fusion protein. For a discussion of suitable vectors for fusion protein production, see D. J. Kroll et al., 1993; *DNA Cell Biol.*, 12:441–453.

Human artificial chromosomes (HACs) can be used to deliver larger fragments of DNA than can be contained and expressed in a plasmid vector. HACs are linear microchromosomes which can contain DNA sequences of 10K to 10M in size, and contain all of the elements that are required for stable mitotic chromosome segregation and maintenance (See, J. J. Harrington et al., 1997, *Nature Genet.*, 15:345–355). HACs of 6 to 10M are constructed and delivered via conventional delivery methods (e.g., liposomes, polycationic amino polymers, or vesicles) for therapeutic purposes.

A variety of protocols for detecting and measuring the expression of the RET16 polypeptide using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the RET16 polypeptide is preferred, but a competitive binding assay can also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211–1216).

Anti-Human RET16 Antibodies and Uses Thereof

Purified RET16 protein, or fragments thereof, can be used to produce antibodies, or to screen libraries of pharmaceutical agents or other compounds, particularly, small molecules, to identify those which specifically bind RET16. Such antibodies can be useful as antagonists or inhibitors of the RET16 polypeptide of the present invention and can be polyclonal, monoclonal, or recombinantly produced.

Antibodies specific for the RET16 polypeptide, or immunogenic peptide fragments thereof, can be generated using methods that have long been known and conventionally practiced in the art. Such antibodies can include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use.

For the production of antibodies, various hosts including goats, rabbits, sheep, rats, mice, humans, and others, can be immunized by injection with RET16 polypeptide, or any peptide fragment or oligopeptide thereof, which has immunogenic properties. Depending on the host species, various adjuvants can be used to increase the immunological response. Nonlimiting examples of suitable adjuvants include Freund's (incomplete), mineral gels such as aluminum hydroxide or silica, and surface active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvumn.*

Preferably, the peptides, fragments, or oligopeptides used to induce antibodies to RET16 polypeptide (i.e., immunogens) have an amino acid sequence having at least five amino acids, and more preferably, at least 7–10 amino acids. It is also preferable that the immunogens are identical to a portion of the amino acid sequence of the natural protein; they can also contain the entire amino acid sequence of a small, naturally occurring molecule. The peptides, fragments or oligopeptides can comprise a single epitope or antigenic determinant or multiple epitopes. Short stretches of RET16 amino acids can be fused with those of another protein, such as KLH, and antibodies are produced against the chimeric molecule.

Monoclonal antibodies to RET16 polypeptide, or immunogenic fragments thereof, can be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, *Nature,* 256:495–497; D. Kozbor et al., 1985, *J. Immunol. Methods,* 81:31–42; R. J. Cote et al., 1983, *Proc. Natl. Acad. Sci. USA,* 80:2026–2030; and S. P. Cole et al., 1984, *Mol. Cell Biol.,* 62:109–120). The production of monoclonal antibodies is well known and routinely used in the art.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA,* 81:6851–6855; M. S. Neuberger et al., 1984, *Nature,* 312:604–608; and S. Takeda et al., 1985, *Nature,* 314:452–454). Alternatively, techniques described for the production of single chain antibodies can be adapted, using methods known in the art, to produce RET16 polypeptide-specific single chain antibodies. Antibodies with related specificity, but of distinct idiotypic composition, can be generated by chain shuffling from random combinatorial immunoglobulin libraries (D. R. Burton, 1991, *Proc. Natl. Acad. Sci. USA,* 88:11120–3). Antibodies can also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA,* 86:3833–3837 and G. Winter et al., 1991, *Nature,* 349:293–299).

Antibody fragments which contain specific binding sites for the RET16 polypeptide can also be generated. For example, such fragments include, but are not limited to, $F(ab')_2$ fragments which can be produced by pepsin digestion of the antibody molecule and Fab fragments which can be generated by reducing the disulfide bridges of the F(ab')$_2$ fragments. Alternatively, Fab expression libraries can be constructed to allow rapid and easy identification of monoclonal Fab fragments with the desired specificity (W. D. Huse et al., 1989, Science, 254.1275–1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between the RET16 polypeptide and its specific antibody. A two-site, monoclonal-based immunoassay utilizing monoclonal antibodies reactive with two non-interfering RET16 polypeptide epitopes is preferred, but a competitive binding assay can also be employed (Maddox, supra).

Therapeutics/Treatments

In an embodiment of the present invention, the polynucleotide encoding the RET16 polypeptide, or any fragment or complement thereof, can be used for therapeutic purposes. In one aspect, antisense to the polynucleotide encoding the RET16 polypeptide can be used in situations in which it would be desirable to block the transcription of RET16 mRNA. In particular, cells can be transformed or transfected with sequences complementary to polynucleotides encoding the RET16 polypeptide, as described in Example 4 herein. Thus, complementary molecules can be used to modulate human RET16 polynucleotide and polypeptide activity, or to achieve regulation of gene function. Such technology is now well known in the art, and sense or antisense oligomers or oligonucleotides, or larger fragments, can be designed from various locations along the coding or control regions of polynucleotide sequences encoding the RET16 polypeptide.

Expression vectors derived from retroviruses, adenovirus, herpes or vaccinia viruses, or from various bacterial plasmids can be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding the RET16 polypeptide. These techniques are described both in J. Sambrook et al., supra and in F. M. Ausubel et al., supra.

The gene encoding the RET16 polypeptide can be turned off by transforming a cell or tissue with an expression vector that expresses high levels of a RET16 polypeptide-encoding polynucleotide, or a fragment thereof. Such constructs can be used to introduce untranslatable sense or antisense sequences into a cell. Even in the absence of integration into the DNA, such vectors can continue to transcribe RNA molecules until they are disabled by endogenous nucleases. Transient expression can last for a month or more with a non-replicating vector, and even longer if appropriate replication elements are designed to be part of the vector system.

Modifications of gene expression can be obtained by designing antisense molecules or complementary nucleic acid sequences (DNA, RNA, or PNA), to the control, 5', or regulatory regions of the gene encoding the RET16 polypeptide, (e.g., signal sequence, promoters, enhancers, and introns). Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (See, for example, J. E. Gee et al., 1994, In: B. E. Huber and B. I. Carr, Molecular and Immunologic Approaches, Futura Publishing Co., Mt. Kisco, N.Y.). The antisense molecule or complementary sequence can also be designed to block translation of mRNA by preventing the transcript from binding to ribosomes.

Ribozymes, i.e., enzymatic RNA molecules, can also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding the RET16 polypeptide.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays.

Complementary ribonucleic acid molecules and ribozymes according to the invention can be prepared by any method known in the art for the synthesis of nucleic acid molecules. Such methods include techniques for chemically synthesizing oligonucleotides, for example, solid phase phosphoramidite chemical synthesis. Alternatively, RNA molecules can be generated by in vitro and in vivo transcription of DNA sequences encoding human RET16. Such DNA sequences can be incorporated into a wide variety of vectors with suitable RNA polymerase promoters such as T7 or SP. Alternatively, the cDNA constructs that constitutively or inducibly synthesize complementary RET16 RNA can be introduced into cell lines, cells, or tissues.

RNA molecules can be modified to increase intracellular stability and half-life. Possible modifications include, but are not limited to, the addition of flanking sequences at the 5' and/or 3' ends of the molecule, or the use of phosphorothioate or 2' O-methyl (rather than phosphodiesterase linkages) within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and are equally suitable for use in vivo, in vitro, and ex vivo. For ex vivo therapy, vectors can be introduced into stem cells taken from the patient and clonally propagated for autologous transplant back into that same patient. Delivery by transfection and by liposome injections can be achieved using methods which are well known in the art.

In another embodiment of the present invention, an expression vector containing the complement of the polynucleotide encoding the RET16 polypeptide, or an antisense oligonucleotide, can be administered to an individual to treat or prevent an inflammatory disease or disorder and/or a disease or disorder associated with uncontrolled cell growth, hyperactivity or stimulation. A variety of specialized oligonucleotide delivery techniques can be employed, for example, encapsulation in unilamellar liposomes and reconstituted Sendai virus envelopes for RNA and DNA delivery (Arad et al., 1986, *Biochem. Biophys. Acta.,* 859:88–94).

In another embodiment, the proteins, antagonists, antibodies, agonists, complementary sequences, or vectors of the present invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any individual in need of such therapy, including, for example, mammals such as dogs, cats, cows, horses, rabbits, monkeys, and most preferably, humans.

Screening Methods

The RET16 protein and nucleic acid can be used in screening assays of candidate bioactive agents that modulate RET16 bioactivity, for potential use to treat inflammation disorders, for example, such as those involving activated and/or hyperactive cells, e.g., T-cells, B-cells, endothelial cells, macrophages, neutrophils, mast cells and eosinophils. In addition, RET16 protein and encoding nucleic acid, as well as the bioactive agents that modulate RET16 activity or function, can be used as effectors in methods to regulate cell activation.

RET16 polynucleotide and polypeptide can also be modulated by interactive molecules. By "modulate" herein is meant that the bioactivity of RET16 is altered, i.e., either increased, augmented, or enhanced, such as by agonists; or decreased, inhibited, or blocked, such as by antagonists. In a preferred embodiment, RET16 bioactivity is inhibited. Because RET16 is expressed in cells stimulated by TNF-alpha, which is a factor involved in inflammatory responses, and is a candidate ubiquitin ligase; it can play a role in intracellular signaling, or it can serve as part of the master switch for the development of inflammatory processes. Accordingly, RET16 can be used as a target to screen for antagonists or inhibitors of its function or expression in the cell signaling cascade.

In another embodiment of the present invention, RET16 proteins and nucleic acids are used in screening assays to identify and detect candidate bioactive agents that modulate RET16 bioactivity, for potential use to treat diseases which can be caused by hyperactivated B and/or T cells, e.g., autoimmune disease, as well as to treat inflammatory diseases involving cells which produce cytokines and factors that promote, accelerate, or exacerbate inflammation, e.g., leukocytes, mast cells, natural killer cells, neutrophils, macrophages, eosinophils, polymorphonuclear leukocytes, and the like, or cell damage in a variety of body tissues. Nonlimiting examples of inflammatory diseases in which the master switch of the intracellular signaling cascade can be upregulated, stimulated, or otherwise involved include arthritis (both rheumatoid and juvenile); psoriasis; asthma; ischemia-reperfusion; rejection of organ or tissue transplants; chronic obstructive pulmonary disease; inflammatory bowel diseases, including Crohn's disease and ulcerative colitis; inacute respiratory distress syndrome; systemic lupus erythematosis, multiple sclerosis and cystic fibrosis. Other diseases or disorders in which bioactive agents which modulate RET16 can be used include autoimmune diseases, cancers, tumors and neoplasms and other diseases related to uncontrolled cell growth, in a variety of tissues, especially those in which RET16 has been found to be expressed. (See, for example, FIGS. 7A–7D).

Generally, in performing such screening methods, RET16 polypeptide is non-diffusably bound to an insoluble support having isolated sample receiving areas (e.g. a microtiter plate, an array, etc.). The criteria for suitable insoluble supports are that they can be made of any composition to which polypeptides can be bound, they are readily separated from soluble material, and they are otherwise compatible with the overall method of screening. The surface of such supports can be solid or porous and of any convenient size or shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient, because a large number of assays can be carried out simultaneously, using small amounts of reagents and samples. The particular manner of binding the polypeptide is not crucial, so long as it is compatible with the reagents and overall methods of the invention, maintains the activity of the peptide and is nondiffusable. Preferred methods of binding include the use of antibodies (which should not hinder the binding of RET16 to its associated proteins), direct binding to "sticky" or ionic supports, chemical crosslinking, etc. Following binding of the polypeptide, excess unbound material is removed by washing. The sample receiving areas can then be blocked as needed through incubation with bovine serum albumin (BSA), casein or other innocuous/nonreactive protein.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays can be used for this purpose, including labeled in vitro protein-protein binding assays, electrophoretic mobility shift assays, immunoassays for protein binding, and the like. The term "agent" as used herein describes any molecule, e.g., protein, oligopeptide, small organic molecule, polysaccharide, polynucleotide, etc., having the capability of directly or indirectly altering the bioactivity of RET16 proteins. Generally a plurality of assay mixtures are run in parallel with different agent concentrations to obtain a differential response to the various concentrations. Typically, one of these concentrations serves as a negative control, i.e., at zero concentration, or below the level of detection.

Candidate agents encompass numerous chemical classes, though typically they are organic molecules, preferably small organic compounds having a molecular weight of more than 100 and less than about 10,000 daltons, preferably, less than about 2000 to 5000 daltons, as a nonlimiting example. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

The determination of the binding of the candidate bioactive agent to the RET16 polypeptide can be accomplished in a number of ways practiced in the art. In one aspect, the candidate bioactive agent is labeled, and binding is determined directly. Where the screening assay is a binding assay, one or more of the molecules can be joined to a label, where the label can directly or indirectly provide a detectable signal. Various labels include radioisotopes, fluorescent and chemiluminescent compounds, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which allows detection, in accordance with known procedures. In some embodiments, only one of the components is labeled. Alternatively, more than one component can be labeled with different labels; for example, the RET16 polypeptide can be labeled with one fluorophor and the candidate agent labeled with another In one embodiment, the candidate bioactive agent is labeled. Labeled candidate bioactive agents are incubated with the RET16 polypeptide for a time sufficient to allow binding, if present. Incubations can be performed at any temperature which facilitates optimal activity, typically between 4° C. and 40° C. Incubation periods are selected for optimum activity, but can also be optimized to facilitate rapid high throughput screening. Typically between 0.1 and 1 hour is sufficient. Excess reagent is generally removed or washed away. The presence or absence of the labeled component is detected to determine and indicate binding.

A variety of other reagents can be included in the screening assay. Such reagents include, but are not limited to, salts, neutral proteins, e.g. albumin, detergents, etc., which can be used to facilitate optimal protein-protein binding and/or reduce non-specific or background interactions. In addition, reagents that otherwise improve the efficiency of the assay, such as protease inhibitors, nuclease inhibitors, anti-microbial agents, etc. can be used. Further, the mixture of components in the method can be added in any order that provides for the requisite binding.

Kits are included as an embodiment of the present invention which comprise containers with reagents necessary to screen test compounds. Depending on the design of the test and the types of compounds to be screened, such kits include human RET16 polynucleotide or polypeptide and instructions for performing the assay.

Enhancement of the Biological Activity/Functional Characteristics of the RET16 Proteins of the Present Invention Through Molecular Evolution Although many of the most biologically active proteins known are highly effective for their specified function in an organism, they often possess characteristics or traits that make them undesirable for transgenic, therapeutic, pharmaceutical, and/or industrial applications. Among these characteristics or traits, a short physiological half-life is the most prominent problem, and is present either at the level of the protein, or the level of the mRNA of the protein. The ability to extend the half-life, for example, would be particularly important for the use of a protein in gene therapy, transgenic animal production, bioprocessing, production and purification of the protein, and use of the protein as a chemical modulator, among others. Therefore, there is a need to identify novel variants of isolated proteins possessing characteristics which enhance their application as a therapeutic for treating diseases of animal origin, in addition to the applicability of the protein to common industrial and pharmaceutical applications.

Thus, in accordance with an aspect of the present invention is the ability to enhance specific characteristics of the invention, e.g., the RET16 polynucleotides and/or proteins, through directed molecular evolution. Such an enhancement can, as non-limiting examples, benefit the following: the utility of the invention as an essential component in a kit; the physical attributes of the invention, such as its solubility, structure, or codon optimization; the specific biological activity of the invention, including any associated enzymatic activity, enzyme kinetics of the protein, the Ki, Kcat, Km, Vmax, Kd of the protein; protein-protein activity; protein-DNA binding activity; antagonist/inhibitory activity (including direct or indirect interaction); agonist activity (including direct or indirect interaction); the antigenicity of the protein (e.g., in which it would be desirable to either increase or decrease the antigenic potential of the protein); the immunogenicity of the protein; the ability of the protein to form dimers, trimers, or multimers with either itself or other proteins; and the antigenic efficacy of the invention, including its subsequent use a preventative treatment for disease or disease states, or as an effector for targeting diseased genes. Moreover, the ability to enhance specific characteristics of a protein can also apply to changing the characterized activity of an enzyme to an activity completely unrelated to its initially characterized activity. Other desirable enhancements of the invention are specific to each individual protein, and would thus be well known in the art and contemplated by the present invention.

For example, an engineered ubiquitin ligase enzyme can be constitutively active upon binding of its substrate. Alternatively, an engineered ubiquitin ligase enzyme can be constitutively active in the absence of substrate binding. In yet another example, an engineered ubiquitin ligase enzyme can be capable of being activated with less than all of the regulatory factors and/or conditions typically required for ubiquitin ligase enzyme activation (e.g., substrate binding, phosphorylation, conformational changes, etc.). Such a ubiquitin ligase enzyme is useful in screens to identify ubiquitin ligase enzyme modulators, among other uses described herein. Alternatively, an engineered ubiquitin ligase enzyme can have altered substrate specificity, and/or enhanced ubiquitin ligase enzyme activity. Alternatively, an engineered ubiquitin ligase enzyme can have decreased ubiquitin ligase enzyme activity.

Directed evolution is comprised of several steps. The first step establishes a library of variants for the gene or protein of interest. The most important step is then to select for those variants that entail the activity to be identified. The design of the screen is essential, since the screen should be selective enough to eliminate non-useful variants, but not so stringent as to eliminate all variants. The last step is then to repeat the above steps using the best variant from the previous screen. Each successive cycle can then be tailored as necessary, such as increasing the stringency of the screen, for example.

A variety of reaction conditions can be utilized to carry out the DNA shuffling reaction. However, specific reaction conditions for DNA shuffling are provided, for example, as described in *PNAS USA*, 91:10747, (1994). Briefly: the DNA substrate to be subjected to the DNA shuffling reaction is prepared. The preparation can be in the form of simply purifying the DNA from contaminating cellular material, chemicals, buffers, oligonucleotide primers, deoxynucleotides, RNAs, etc., and can entail the use of DNA purification kits, such as those provided by Qiagen, Inc., or by Promega, Corp., for example.

Once the DNA substrate has been purified, it is subjected to Dnase I digestion. About 2–4 μg of the DNA substrate(s) are digested with 0.0015 units of Dnase I (Sigma) per μl in 100 μl of 50 mM Tris-HCl, pH 7.4/1 mM $MgCl_2$ for 10–20 minutes at room temperature. The resulting DNA fragments of 10–50 bp are then purified by subjecting them to electrophoresis through a low-melting point agarose gel (2%) and/or onto DE81 ion-exchange paper (Whatman). Alternatively, the DNA fragments can be purified using Microcon concentrators (Amicon) of the appropriate molecular weight cutoff, or oligonucleotide purification columns (Qiagen) can be used, in addition to other methods known in the art. If using DE81 ion-exchange paper, the 10–50 bp fragments can be eluted from the paper using 1 M NaCl, followed by ethanol precipitation.

The resulting purified fragments are then subjected to a PCR assembly reaction by re-suspension in a PCR mixture containing: 2 mM of each dNTP, 2.2 mM $MgCl_2$, 50 mM KCl, 10 mM Tris•HCL, pH 9.0, and 0.1% Triton X-100, at a final fragment concentration of 10–30 ng/μl. No primers are added at this point. Taq DNA polymerase (Promega) is used at 2.5 units per 100 μl of reaction mixture. A PCR program of 94 C for 60 seconds (s); 94 C for 30 s, 50–55 C for 30 s, and 72 C for 30 s using 30–45 cycles, followed by 72 C for 5 minutes using an MJ Research (Cambridge, Mass.) PTC-150 thermocycler is used.

After the assembly reaction is completed, a 1:40 dilution of the resulting primeness product is then introduced into a PCR mixture (using the same buffer mixture used for the assembly reaction) containing 0.8 μm of each primer and subjecting this mixture to 15 cycles of PCR (using 94 C for 30 s, 50 C for 30 s, and 72 C for 30 s). The preferred primers are those which correspond to the nucleic acid sequences of the polynucleotide(s) utilized in the shuffling reaction. Such primers can consist of modified nucleic acid base pairs using methods known in the art and referred to elsewhere herein, or can contain additional sequences (i.e., for adding restriction sites, mutating specific base-pairs, etc.). The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be well understood by the skilled artisan and are encompassed by the invention. The DNA shuffling method can also be tailored to the desired level of mutagenesis using the methods described by Zhao et al. 1997, *Nucl Acid Res.*, 25(6): 1307–1308.

As described above, once the randomized pool has been created, it can then be subjected to a specific screen to identify the variant possessing the desired characteristic(s). Once the variant has been identified, DNA corresponding to the variant can then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology can be found in the following publications: J. C. Moore et al., 1997, *J. Mol. Biol.*, 272:336–347; F. R. Cross et al., 1998, *Mol. Cell. Biol.*, 18:2923–2931; and A. Crameri et al., 1997, *Nat. Biotech.*, 15:436–438.

DNA shuffling has several advantages. First, it makes use of beneficial mutations. When combined with screening, DNA shuffling allows the discovery of the best mutational combinations and does not assume that the best combination contains all the mutations in a population. Second, recombination occurs simultaneously with point mutagenesis. An effect of forcing DNA polymerase to synthesize full-length genes from the small fragment DNA pool results in a background mutagenesis rate. In combination with a stringent selection method, enzymatic activity has been evolved up to a 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there can be at least one or more neutral or inhibitory mutations. Such mutations can be removed by including in the assembly reaction an excess of the wild-type random-sized fragments, in addition to the random-sized fragments of the selected mutant from the previous selection. During the next selection, some of the most active variants of the polynucleotide/polypeptide/enzyme, should have lost the inhibitory mutations.

Finally, recombination enables parallel processing. This represents a significant advantage, since there are likely to be multiple characteristics that make a protein more desirable (e.g., solubility, activity, etc.). Since it is increasingly difficult to screen for more than one desirable characteristic or trait at a time, other methods of molecular evolution tend to be inhibitory. However, using recombination, it is possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention can be created and isolated using DNA shuffling technology. Such a variant can have all of the desired characteristics, although it may be highly immunogenic in a host due to its novel intrinsic structure. Specifically, the desired characteristic can cause the polypeptide to have a non-native structure which could no longer be recognized as a "self" molecule, but rather as "foreign", and thus activate a host immune response directed against the novel variant. Such a problem can be overcome, for example, by including a copy of the gene sequence for a xenobiotic ortholog of the native protein with the gene sequence of the novel variant gene in one or more cycles of DNA shuffling. The molar ratio of the ortholog and the novel variant DNAs could be varied accordingly. Ideally, the resulting hybrid variant identified contains at least some of the coding sequence which enabled the xenobiotic protein to evade the host immune system, as well as the coding sequence of the original novel variant that provided the desired characteristics.

Likewise, the present invention encompasses the application of DNA shuffling technology to the evolution of the polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homolog sequences, additional homologous sequences, additional non-homologous sequences, sequences from another species, and any number and combination of the above.

In addition to the above-described methods, there are a number of related methods that may also be applicable, or desirable, with respect to this aspect in certain cases. Representative among these are the methods discussed in PCT applications WO 98/31700 and WO 98/32845, which are hereby incorporated by reference. Furthermore, related methods can also be applied to the polynucleotide sequences of the present invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and A. Crameri et al., 1997, *Nat. Biotech.*, 15:436–438, respectively.

Additional methods of applying "DNA shuffling" technology to the polynucleotides and polypeptides of the present invention, including their proposed applications, can be found in U.S. Pat. No. 5,605,793; PCT Application No. WO 95/22625; PCT Application No. WO 97/20078; PCT Application No. WO 97/35966; and PCT Application No. WO 98/42832. PCT Application No. WO 00/09727 specifically provides methods for applying DNA shuffling to the identification of herbicide selective crops which can be applied to the polynucleotides and polypeptides of the present invention. In addition, PCT Application No. WO 00/12680 provides methods and compositions for generating, modifying, adapting, and optimizing polynucleotide sequences that confer detectable phenotypic properties on plant species. Each of the above are hereby incorporated in their entirety herein for all purposes.

Pharmaceutical Compositions

A further embodiment of the present invention embraces physiologically acceptable and pharmaceutically acceptable compositions comprising RET16 nucleic acids, encoded polypeptides, or peptides, antibodies to RET16 polypeptides, or fragments thereof, mimetics, agonists (e.g., activators), or antagonists (e.g., inhibitors) of the RET16 polypeptide or polynucleotide. Also contemplated by this invention is the administration of the pharmaceutical or physiologically acceptable composition, in conjunction with a pharmaceutically acceptable carrier, diluent, or excipient, for any of the above-described therapeutic uses and effects. The compositions can be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (i.e., the RET16 nucleic acid or polypeptide, or functional fragments thereof), the pharmaceutical compositions can contain suitable pharmaceutically acceptable carriers or excipients comprising auxiliaries which facilitate processing of the active compounds into preparations which can be used pharmaceutically. Further details on techniques for formulation and administration are provided in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents can be added, such as cross-linked polyvinyl pyrrolidone, agar, alginic acid, or a physiologically acceptable salt thereof, such as sodium alginate.

Dragee cores can be used in conjunction with physiologically suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification, or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. In addition, suspensions of the active compounds can be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension can also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes.

The pharmaceutical composition can be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, combined with a buffer prior to use. After the pharmaceutical compositions have been prepared, they can be placed in an appropriate container and labeled for treatment of an indicated condition. For administration of the RET16 product, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model can also be used to determine the appropriate concentration range and route of administration. Such information can then be used and extrapolated to determine useful doses and routes for administration in humans.

A therapeutically effective dose refers to that amount of active ingredient, for example, the RET16 polypeptide, or active fragments thereof, antibodies to the RET16 polypeptide, agonists or antagonists of the RET16 polypeptide, which ameliorates, reduces, or eliminates the symptoms or condition. Therapeutic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $ED_{50}/LD_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the ED50 with little or no toxicity. The dosage varies within this range depending upon the dosage form employed, sensitivity of the patient, and the route of administration.

The exact dosage will be determined by the practitioner, who will consider the factors related to the individual requiring treatment. Dosage and administration are adjusted to provide sufficient levels of the active moiety or to maintain the desired effect. Factors which may be taken into account include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions can be administered every 3 to 4 days, every week, or once every two weeks, depending on half-life and clearance rate of the particular formulation.

Normal dosage amounts can vary from 0.1 to 100,000 micrograms (μg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

Assays and Diagnostics

In another embodiment of the present invention, antibodies which specifically bind to the RET16 polypeptide can be used for the diagnosis of conditions or diseases characterized by expression (or overexpression) of the RET16 polynucleotide or polypeptide, or in assays to monitor patients being treated with RET16 polypeptide, or its agonists, antagonists, or inhibitors. The antibodies useful for diagnostic purposes can be prepared in the same manner as those described above for use in therapeutic methods. Diagnostic assays for the RET16 polypeptide include methods which utilize the antibody and a label to detect the protein in human body fluids or extracts of cells or tissues. The antibodies can be used with or without modification, and can be labeled by joining them, either covalently or non-covalently, with a reporter molecule. A wide variety of reporter molecules which are known in the art can be used, several of which are described above.

Several assay protocols including ELISA, RIA, and FACS for measuring the RET16 polypeptide are known in the art and provide a basis for diagnosing altered or abnormal levels of RET16 polypeptide expression. Normal or standard values for RET16 polypeptide expression are established by combining body fluids or cell extracts taken from normal mammalian subjects, preferably human, with antibody to the RET16 polypeptide under conditions suitable for complex formation. The amount of standard complex formation can be quantified by various methods; photometric means are preferred. Quantities of the RET16 polypeptide expressed in subject sample, control sample, and disease samples from biopsied tissues are compared with the standard values. Deviation between standard and subject values establishes the parameters for diagnosing disease.

According to another embodiment of the present invention, the polynucleotides encoding RET16 polypeptide can be used for diagnostic purposes. The polynucleotides which can be used include oligonucleotide sequences, complementary RNA and DNA molecules, and PNAs. The polynucleotides can be used to detect and quantify RET16-encoding nucleic acid expression in biopsied tissues in which expression (or under- or overexpression) of RET16 polynucleotide can be correlated with disease. The diagnostic assay can be used to distinguish between the absence, presence, and excess expression of RET16, and to monitor regulation of RET16 polynucleotide levels during therapeutic treatment or intervention.

In a related aspect, hybridization with PCR probes which are capable of detecting polynucleotide sequences, including genomic sequences, encoding RET16 polypeptide, or closely related molecules, can be used to identify nucleic acid sequences which encode the RET16 polypeptide. The specificity of the probe, whether it is made from a highly specific region, e.g., about 8 to 10 or 12 or 15 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the RET16 polypeptide, alleles thereof, or related sequences.

Probes can also be used for the detection of related sequences, and should preferably contain at least 50%, preferably greater than 80%, of the nucleotides encoding RET16 polypeptide. The hybridization probes of this invention can be DNA or RNA and can be derived from the nucleotide sequence of SEQ ID NO:1 or SEQ ID NO:3, or from genomic sequence including promoter, enhancer elements, and introns of the naturally occurring RET16 protein.

Methods for producing specific hybridization probes for DNA encoding the RET16 polypeptide include the cloning of nucleic acid sequence that encodes the RET16 polypeptide, or RET16 derivatives, into vectors for the production of mRNA probes. Such vectors are known in the art, commercially available, and can be used to synthesize RNA probes in vitro by means of the addition of the appropriate RNA polymerases and the appropriate labeled nucleotides. Hybridization probes can be labeled by a variety of detector/reporter groups, e.g., radionuclides such as $^{32}$P or $^{35}$S, or enzymatic labels, such as alkaline phosphatase coupled to the probe via avidin/ biotin coupling systems, and the like.

The polynucleotide sequence encoding the RET16 polypeptide can be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of RET16, or to detect altered RET16 expression. Such qualitative or quantitative methods are well known in the art.

In a particular aspect, the nucleotide sequence encoding the RET16 polypeptide can be useful in assays that detect activation or induction of various inflammatory disease, neoplasms or cancers, particularly those mentioned supra. The nucleotide sequence encoding the RET16 polypeptide can be labeled by standard methods, and added to a fluid or tissue sample from a patient under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the RET16 polypeptide in the sample indicates the presence of the associated disease. Such assays can also be used to evaluate the efficacy of a particular therapeutic treatment regimen in animal studies, in clinical trials, or in monitoring the treatment of an individual patient.

To provide a basis for the diagnosis of disease associated with expression of RET16, a normal or standard profile for expression is established. This can be accomplished by combining body fluids or cell extracts taken from normal subjects, either animal or human, with a sequence, or a fragment thereof, which encodes the RET16 polypeptide, under conditions suitable for hybridization or amplification. Standard hybridization can be quantified by comparing the values obtained from normal subjects with those from an experiment where a known amount of a substantially purified polynucleotide is used. Standard values obtained from normal samples can be compared with values obtained from samples from patients who are symptomatic for disease. Deviation between standard and subject (patient) values is used to establish the presence of disease.

Once disease is established and a treatment protocol is initiated, hybridization assays can be repeated on a regular basis to evaluate whether the level of expression in the patient begins to approximate that which is observed in a normal individual. The results obtained from successive assays can be used to show the efficacy of treatment over a period ranging from several days to months.

With respect to cancer, the presence of an abnormal amount of transcript in biopsied tissue from an individual can indicate a predisposition for the development of the disease, or can provide a means for detecting the disease prior to the appearance of actual clinical symptoms. A more definitive diagnosis of this type can allow health professionals to employ preventative measures or aggressive treatment earlier, thereby preventing the development or further progression of the cancer.

Additional diagnostic uses for oligonucleotides designed from the nucleic acid sequence encoding the RET16 polypeptide can involve the use of PCR. Such oligomers can be chemically synthesized, generated enzymatically, or produced from a recombinant source. Oligomers will preferably comprise two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers can be employed under less stringent conditions for detection and/ or quantification of closely related DNA or RNA sequences.

Methods suitable for quantifying the expression of RET16 include radiolabeling or biotinylating nucleotides, co-amplification of a control nucleic acid, and standard curves onto which the experimental results are interpolated (P. C. Melby et al., 1993, *J. Immunol. Methods*, 159:235–244; and C. Duplaa et al., 1993, *Anal. Biochem.*, 229–236). The speed of quantifying multiple samples can be accelerated by running the assay in an ELISA format where the oligomer of interest is presented in various dilutions and a spectrophotometric or calorimetric response gives rapid quantification.

In another embodiment of the present invention, oligonucleotides, or longer fragments derived from the RET16 polynucleotide sequence described herein, can be used as targets in a microarray. The microarray can be used to monitor the expression level of large numbers of genes simultaneously (to produce a transcript image), and to identify genetic variants, mutations and polymorphisms. This information can be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology*, 14:1675–1680; and M. Schena et al., 1996, *Proc. Natl. Acad. Sci. USA*, 93:10614–10619). Microarrays are further described in U.S. Pat. No. 6,015,702 to P. Lal et al.

In another embodiment of this invention, the nucleic acid sequence which encodes the RET16 polypeptide can also be used to generate hybridization probes which are useful for mapping the naturally occurring genomic sequence. The sequences can be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.*, 7:127–134 and by B. J. Trask, 1991, *Trends Genet.*, 7:149–154.

In another embodiment of the present invention, the RET16 polypeptide, its catalytic or immunogenic fragments or oligopeptides thereof, can be used for screening libraries of compounds in any of a variety of drug screening techniques. The fragment employed in such screening can be free in solution, affixed to a solid support, borne on a cell surface, or located intracellularly. The formation of binding complexes, between the RET16 polypeptide, or portion thereof, and the agent being tested, can be measured utilizing techniques commonly practiced in the art and as described above.

Another technique for drug screening which can be used provides for high throughput screening of compounds having suitable binding affinity to the protein of interest as described in WO 84/03564. In this method, as applied to the RET16 protein, large numbers of different small test compounds are synthesized on a solid substrate, such as plastic pins or some other surface. The test compounds are reacted with the RET16 polypeptide, or fragments thereof, and washed. Bound RET16 polypeptide is then detected by methods well known in the art. Purified RET16 polypeptide can also be coated directly onto plates for use in the aforementioned drug screening techniques. Alternatively, non-neutralizing antibodies can be used to capture the peptide and immobilize it on a solid support.

Other screening and small molecule (e.g., drug) detection assays which involve the detection or identification of small molecules that can bind to a given protein, i.e., the RET16 protein, are encompassed by the present invention. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, RET16 polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

In a further embodiment of this invention, competitive drug screening assays can be used in which neutralizing antibodies capable of binding RET16 polypeptide specifically compete with a test compound for binding to RET16 polypeptide. In this manner, the antibodies can be used to detect the presence of any peptide which shares one or more antigenic determinants with the RET16 polypeptide.

Transgenics and Knock Outs

The present invention further encompasses transgenic non-human mammals, preferably mice, that comprise a recombinant expression vector harboring a nucleic acid sequence that encodes human RET16 comprising the amino acid sequence of SEQ ID NO:2 or SEQ ID NO:4.

Transgenic non-human mammals useful to produce recombinant proteins are well known to the skilled practitioner, as are the expression vectors necessary and the techniques for generating transgenic animals. Generally, the transgenic animal comprises a recombinant expression vector in which the nucleotide sequence that encodes human RET16 is operably linked to a tissue specific promoter whereby the coding sequence is only expressed in that specific tissue. For example, the tissue specific promoter can be a mammary cell specific promoter and the recombinant protein so expressed is recovered from the animal's milk.

The transgenic animals, particularly transgenic mice, containing a nucleic acid molecule which encodes human RET16 can be used as animal models for studying in vivo the overexpression of RET16 and for use in drug evaluation and discovery efforts to find compounds effective to inhibit or modulate the activity of RET16, such as for example compounds for treating inflammatory disorders, diseases, or conditions. One having ordinary skill in the art using standard techniques, such as those taught in U.S. Pat. No. 4,873,191, issued Oct. 10, 1989 to Wagner and in U.S. Pat. No. 4,736,866, issued Apr. 12, 1988 to Leder, can produce transgenic animals which produce human RET16, and use the animals in drug evaluation and discovery projects.

Another aspect of the present invention relates to knock-out mice and methods of using the same. In particular, transgenic mice can be generated which are homozygous for a mutated, non-functional RET16 gene which is introduced into the animals using well known techniques. The knock-out mice produce no functional RET16 and thus are useful to study the function of RET16. Furthermore, the mice can be used in assays to study the effects of test compounds in RET16 deficient animals. For instance, RET16-deficient mice can be used to determine if, how and to what extent RET16 inhibitors will effect the animal and thus address concerns associated with inhibiting the activity of the molecule.

Methods of generating genetically deficient "knock out" mice are well known and are disclosed in M. R. Capecchi, 1989, *Science*, 244:1288–1292 and P. Li et al., 1995, *Cell*, 80:401–411. For example, the mouse (or human) RET16 cDNA clone can be used to isolate a murine RET16 genomic clone. The genomic clone can be used to prepare a RET16 targeting construct which can disrupt the RET16 gene in the mouse by homologous recombination. The targeting construct contains a non-functioning portion of the RET16 gene which inserts in place of the functioning portion of the native mouse gene. The non-functioning insert generally contains an insertion in the exon that encodes the active region of RET16. The targeting construct can contain markers for both positive and negative selection. The positive selection marker allows for the selective elimination of cells which do not carry the marker, while the negative selection marker allows for the elimination of cells that carry the marker.

For example, a first selectable marker is a positive marker that will allow for the survival of cells carrying it. In some instances, the first selectable marker is an antibiotic resistance gene, such as the neomycin resistance gene, which can be placed within the coding sequence of the RET16 gene to render it non-functional, while at the same time rendering the construct selectable. The antibiotic resistance gene is within the homologous region which can recombine with native sequences. Thus, upon homologous recombination, the non-functional and antibiotic resistance selectable gene sequences will be taken up. Knock-out mice can be used as models for studying inflammation-related disorders and screening compounds for treating these disorders.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Constructs/DNA are then injected into the blastocyst stage and implanted into pseudopregnant females. Chimeric offspring which are capable of transferring the recombinant genes in their germline are selected, mated and their offspring examined for heterozygous carriers of the recombined genes. Mating of the heterozygous offspring can then be used to generate fully homozygous offspring which constitute RET16-deficient knock-out mice.

Other embodiments of the present invention embrace methods of using the RET16 polynucleotides and encoded polypeptides, fragments thereof, or antibodies thereto. More particularly, such methods include a method of using a polynucleotide sequence to purify a molecule or compound in a sample, where the molecule or compound specifically binds to the polynucleotide. Such a method comprises combining a RET16 polynucleotide of this invention under conditions to allow specific binding; detecting specific binding between the RET16 polynucleotide and the molecule or compound in the sample; recovering the bound polynucleotide; and separating the polynucleotide from the molecule or compound, thereby obtaining a purified molecule or compound.

Other methods in accordance with the present invention involve the screening for candidate compounds that are capable of modulating the activity of a cell signaling protein, such as RET16, comprising contacting a test compound, e.g., antagonists or agonists, with a cell or tissue that expresses a RET16 protein, or functional fragment thereof, and selecting as candidate modulating compounds those test compounds that modulate activity of the RET16 protein that is involved in the cell signaling cascade. In such a method the RET16 cell signaling cascade protein activity can be its binding to an interacting domain of a second intracellular cell signaling protein.

Another method encompassed by the present invention involves screening for candidate compounds that are capable of binding to a RET16 cell signaling protein or fragment thereof, which includes contacting a test compound with (i) a cell or tissue expressing the RET16 cell signaling protein according to the present invention, or (ii) an isolated protein thereof; and selecting test compounds that bind to the RET16 cell signaling protein. An additional method of this invention is that of screening for compounds to identify those compounds which enhance, increase, or accelerate the binding of a RET16 protein with a second cell signaling protein. Such a method involves contacting the RET16 protein according to the present invention with a second cell signaling molecule with which it binds or associates in the presence or absence of a test compound under conditions which permit binding and determining if the level of binding of the RET16 protein to the second cell signaling molecule is enhanced, increased or accelerated by comparing the level of binding in the presence of the test compound with that in the absence of the test compound. It will be appreciated that the foregoing methods are particularly suited for performance by high throughput screening.

EXAMPLES

The Examples below are provided to illustrate the subject invention and are not intended to limit the invention. The Examples do not include detailed descriptions of conventional methods employed, e.g., the construction of vectors, the insertion of cDNA into such vectors, or the introduction of the resulting vectors into appropriate hosts. Such methods are well known to those having skill in the art and are described in numerous publications, for example, Sambrook, Fritsch and Maniatis, 1989, *Molecular Cloning: A Laboratory Manual*, $2^{nd}$ Edition, Cold Spring Harbor Laboratory Press, USA.

Example 1

Methods

A. Isolation of the Human RET16 Full-length ORF Coding Sequence clone containing the predicted coding sequence of RET16 was isolated from human microvascular endothelial cells (HMVECs) treated with tumor necrosis factor alpha (TNFα) for 6 hours using reverse transcription/polymerase chain reaction (RT/PCR). A triple primer set (each at 400 nM final concentration) was used to amplify a 1532 bp sequence using the following conditions:

JNF 346 (5'-TCACCTGCGCGGCACGTGACCC-3'), (SEQ ID NO:17);

JNF 493 (5'-TTTACTTTTGGTGTGTCTCCAGCC-3'), (SEQ ID NO:18);

JNF 494 (5'-TTACTTTTGGTGTGTCTCCAGCCATC-TATTGATGGC-3'), (SEQ ID NO:19) with 200 μM dNTP's, 1× Advantage 2 Polymerase PCR Buffer, 1× Advantage 2 Polymerase, and 2.0 μl DNA in 25.0 μl reaction. The experiment was cycled 35 times through 94° C. for 30 seconds, 68° C. for 30 seconds, and 72° C. for 2 minutes. At the completion of the reaction, 6.0 μl of loading dye was added and the entire reaction was separated by gel electrophoresis in a 1.2% agarose gel containing ethidium bromide. An ~1.6 kb size band was excised from the gel and purified using the QIAgen gel extraction kit (QIAgen, Valencia, Calif.). This fragment was ligated into the pTAdv cloning vector (Clontech, Palo Alto, Calif.) and sequenced using standard methods. Ret16pTAdv_Endo_01 contains a 1532 bp sequence corresponding to the predicted Ret16 coding sequence.

A nucleic acid sequence encoding the RET16 polypeptide was first identified in a subtraction library from TNF-alpha stimulated human lung microvascular endothelial cells (HMVEC). This subtraction clone sequence encoded a 630 bp partial cDNA sequence, SEQ ID NO:5, as shown in FIG. 4C. The consensus sequence, SEQ ID NO:1, (FIGS. 1 and 3), was derived from the following overlapping and/or extended nucleic acid sequences: Incyte clones 2552523 (LUNGTUT06), 4632828 (GBLADIT02), 1687704 (PROSTUT10), 2674742 (KIDNNOT19), and public EST clone AI187875 (testis).

B. Identification of a Murine RET16 Gene Ortholog

To identify the murine ortholog of the human RET16 gene, the coding sequence of huRET16 was used to search against the mouse EST database as described hereinabove. Several murine EST's were identified. They are as follows: AU035693, AA 18718, AA204608, W41056, AW146018, AI450495, AI875443, AI316544, AW494796, AW146018 and BE983890. The muRET16 nucleic acid sequence has 80% identity with huRET16. The muRET16 amino acid sequence is 82.5% identical to huRET16 (86.5% similarity). MuRET16 has 7 predicted WD repeats and 1 SAM domain, all with a score >10.

C. Human RET16 Gene Genomic Organization

A genomic clone was identified containing RET16 gene sequence. Clone hRPK.35_A_1 (GenbankAN AC006501) was used to decipher RET16 exon-intron boundaries. (FIG. 18). RET16 is composed of 11 exon fragments. Exon 1 consists of nucleotides 1–123. Exon 2 consists of nucleotides 124–545. Exon 3 consists of nucleotides 546–730. Exon 4 consists of nucleotides 731–823. Exon 5 consists of nucleotides 824–917. Exon 6 consists of nucleotides 918–951. Exon 7 consists of nucleotides 952–992. Exon 8 consists of nucleotides 993–1099. Exon 9 consists of nucleotides 1100–1279. Exon 10 consists of nucleotides 1280–1420. Exon 11 consists of nucleotides 1421–1810. Exon 11 is followed by a poly A tail. A polyadenylation site (AATAA) is located from 1795–1799. According to AC006501, intron 1–intron 10 are 3489, 2755, 4123, 3750, 11859, 1824, 80, 1382, 7683, and 12181 nucleotides in length, respectively.

D. HMVEC for Cell Culture

Primary cultures of human lung microvascular endothelial cells, from a single donor, were obtained from Clonetics (San Diego, Calif.). The cells were grown according to the protocol provided in the endothelial cell growth medium-2 kit (CC-3202) with 5% fetal bovine serum (Hyclone, Logan, Utah). The cells were passaged by trypsinization. The cells were first seeded into a T-25 tissue culture flask and after reaching approximately 90% confluence, and then they were passaged into T-225 tissue culture flasks at $1.2 \times 10^6$ cells/flask. When the cells had grown to reach approximately 90% confluence, they were passaged and seeded into T-225 flasks at $1.8 \times 10^6$ cells/ml. For normal growth conditions, the medium was changed every 48 hours.

E. HMVEC Cell Treatment for RNA Isolation

Subconfluent (i.e., 90% confluent) T-225 flasks of HMVEC cells were adjusted to 40 ml of medium per flask by removing medium. Several of the flasks were treated with 10 ng/ml TNF-alpha for 1 hour, 6 hours and 24 hours; other flasks were not treated with TNF-alpha as controls. TNF-alpha-treated cells were compared with untreated cells. The medium was not changed at the time of TNF-alpha addition.

F. RNA Isolation

The treated flasks of HMVEC cells were briefly trypsinized (10 ml of trypsin per flask). Trypsinization was terminated by the addition of fetal calf serum to 50% final volume and the flasks were rinsed with PBS, pH 7.4 (Gibco, Grand Island, N.Y.). The pooled cells and the PBS rinse from the flasks were pooled and centrifuged (534×g) for 10 minutes, and the cell pellet was resuspended in PBS and re-centrifuged. The supernatant was removed and the cell pellet used for RNA isolation. PolyA+RNA was isolated directly using Fast Track 2.0™ (Invitrogen, Carlsbad, Calif.).

G. Construction of the Subtraction Library

The PCR-select cDNA subtraction kit™ (Clontech, Palo Alto, Calif.) was used to generate a subtraction library from untreated HMVEC poly A+RNA (tester) and 1 hour TNF-treated HMVEC poly A+RNA (driver), according to the manufacturer's protocols. Ten secondary PCR reactions were combined and run on a 2% agarose gel. Fragments ranging from approximately 0.3 kb to 10 kb were gel purified using the QIAgen gel extraction kit (QIAgen Inc., Valencia, Calif.) and inserted into the TA cloning vector, pCR2.1 (Invitrogen). TOP10F' competent *E. coli* (Invitrogen) were transformed and plated on LB plates containing 50 micrograms/ml ampicillin. Clones were isolated and grown in LB broth containing similar concentrations of ampicillin. Plasmids were sequenced according to standard methods.

H. Multiple Tissue Northern Protocol

Multiple Tissue Northern blots (MTN) were obtained from Clontech (Palo Alto, Calif.). The MTN's used were human MTN (#7760-1), human MTN II (#7759-1), human MTN III (#7767-1), and human cancer cell line MTN (#7757-1).

Membranes were prehybridized with ExpressHyb hybridization solution (Clontech) for 1 hour at 68° C. and then hybridized for 2 hours with a $^{32}$P-labeled probe prepared as follows: The original isolated RET16 subtraction clone was digested using EcoR1 restriction endonuclease (Life Technologies, Gaithersburg, Md.). A 540 bp partial cDNA fragment was labeled with $^{32}$P-dCTP using a random primed labeling kit (Roche Biochemicals, Indianapolis, Ind.) according to the manufacturer's instructions. Radioactive probe was added at a specific activity of $2 \times 10^6$ counts per minute per milliliter of hybridization solution.

After hybridization, membranes were washed by continuous shaking for 30 minutes with low stringency solution (2×SSC/0.05% SDS) at room temperature with 2 changes of solution. Membranes were then washed for 30 minutes with high stringency solution (0.1×SSC/0.1% SDS) at 50° C. with 1 change of solution. The membranes were exposed with intensifying screens to X-ray film at −70° C. for 10 days. (FIGS. 7A–7D).

Example 2

Alternative Splice Variants of HuRET16

Two alternative splice forms of RET16 (also called RET16.1 herein), i.e., RET16.2 and RET16.3, have been identified. RET16.2 was identified from human microvascular endothelial cells treated with TNF-α using PCR amplification. Briefly, in an effort to clone the full-length coding sequence of RET16, a second band of lesser size was amplified, in addition to the 1500 bp RET16 amplimer. This second amplimer migrated slightly less than 1300 bp. Both fragments were cloned into pTAdv TA cloning vector and were sequenced. Exon fragments from RET16 were aligned with the second amplimer sequence, called RET16.2, a splice variant of RET16. Four exons were found to be deleted in RET16.2. These exons are exon 5–8 and correspond to WD repeats #6 and #7. The cDNA clone of the RET16.2 splice variant was deposited with the American Type Culture Collection (ATCC), 10801 University Boulevard, Manassas, Va. 20110-2209 under Accession No. PTA-3161 on Mar. 7, 2001 under the terms of the Budapest Treaty. Accordingly, the present invention provides the RET16.2 cDNA nucleic acid sequence comprising ATCC Deposit Accession No. PTA-3161.

The second RET16 splice variant (RET16.3) was identified in Incyte clone identification number 3111127 (Incyte Genomics, Palo Alto, Calif.). Clone 3111127 was sequenced and found to contain an extra exon fragment (9x). This exon is inserted between exon 9 and exon 10. The amino acid sequence of this exon is extremely hydrophobic. An analysis of the RET16.3 variant's amino acid sequence with SEQ-WEB indicated the presence of a transmembrane domain. This extra exon also disrupts the SAM domain. The cDNA clone of the RET16.3 splice variant was deposited with the ATCC under Accession No. PTA-3161 on Mar. 7, 2001 under the terms of the Budapest Treaty. Also in accordance with the present invention is the RET16.3 cDNA nucleic acid sequence comprising ATCC Deposit Accession No. PTA-3161.

A. RET16.2 Nucleic Acid Sequence Identification (FIGS. 19A and 19B)

As described for human RET16 (RET21.1), a clone containing the predicted coding sequence of Ret16 was isolated from human microvascular endothelial cells (HM-VECS) treated with tumor necrosis factor alpha (TNFα) for 6 hours using reverse transcription/polymerase chain reaction (RT/PCR). A triple primer set (each at 400 nM final concentration) was used to amplify a 1532 bp sequence using the following conditions:

JNF 346 (5'-TCACCTGCGCGGCACGTGACCC-3'), (SEQ ID NO:17);
JNF 493 (5'-TTTACTTTTGGTGTGTCTCCAGCC-3'), (SEQ ID NO:18);
JNF 494 (5'-TTACTTTTGGTGTGTCTCCAGCCATC-TATTGATGGC-3'), (SEQ ID NO:19), 200 µM dNTP's, 133 Advantage 2 Polymerase PCR Buffer, 1x Advantage 2 Polymerase, and 2.0 µl DNA in 25.0 µl reaction. The experiment was cycled 35 times through 94° C. for 30 seconds, 68° C. for 30 seconds, and 72° C. for 2 minutes. At the completion of the reaction, 6.0 µl of loading dye was added and the entire reaction was separated by gel electrophoresis in a 1.2% agarose gel containing ethidium bromide. In addition to the 1.6 kb RET16.1 transcript, a 1.3 kb RET16.2 transcript was excised from the gel and purified using the QIAgen gel extraction kit (QIAgen, Valencia, Calif.). This fragment was ligated into the pTAdv cloning vector (Clontech, Palo Alto, Calif.) and sequenced using standard methods. The variant RET16.2, (Ret16pTAdv_Endo_03), SEQ ID NO:12, was found to contain a 1272 bp sequence corresponding to the predicted Ret16 coding sequence, however, analysis of the exon-intron structure revealed a deletion of exons 5–8. The deduced amino acid sequence of RET16.2 is presented in SEQ ID NO:13.

B. RET16.3 Nucleic Acid Sequence Identification (FIGS. 20A and 20B)

A 5' EST was identified from the Incyte EST database and purchased from Incyte Genomics (Palo Alto, Calif.). This clone was prepared according to the manufacturer's protocols and sequenced. Sequences contained within clone ID 3111127 were found to correspond to RET16, also called RET16.1; however, an additional fragment was present between exons 9 and 10. This exon is 78 nucleotides long, does not change the reading frame of the sequence and adds an additional 23 amino acid residues to the protein sequence. This sequence is extremely hydrophobic. The Incyte 3111127 insert is 1908 bp in length. This RET16 variant is termed RET16.3 herein (SEQ ID NO:14) and its deduced amino acid sequence is presented in SEQ ID NO:15.

Example 3

Human RET16 Tissue Expression Analysis by RT-PCR

Figure 11:
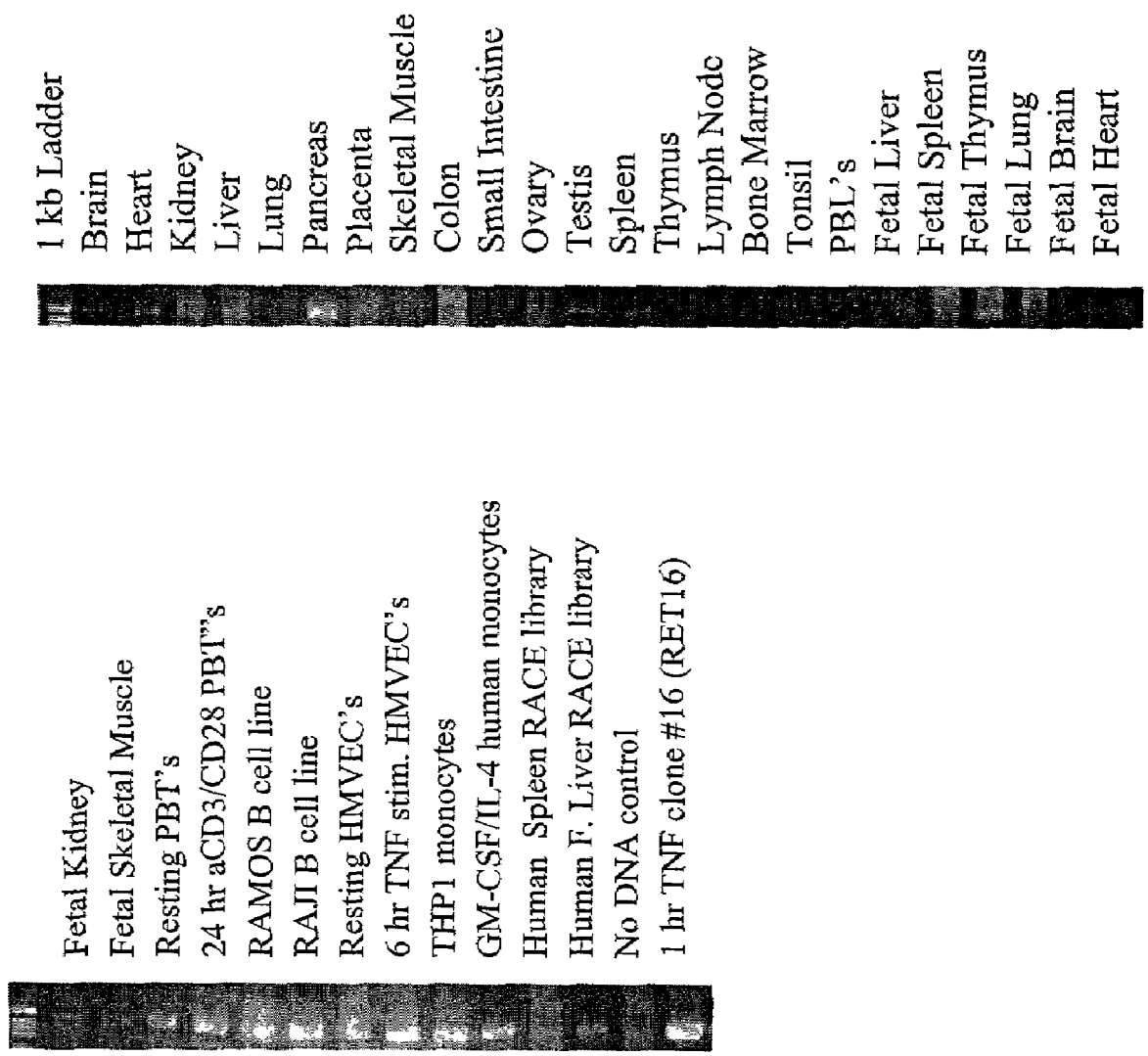
FIG. 11 shows reverse transcriptase polymerase chain reaction (RT-PCR) amplification of the human RET16 transcript from a variety of tissue sources (Example 3).

To analyze RET16 tissue expression, multiple tissue cDNA panels were purchased from Clontech Laboratories (Palo Alto, Calif.) and used in the polymerase chain reaction. Briefly, 1.0 microliter of cDNA from each tissue was added to a 24 microliter reaction mixture containing the following reagents: 0.4 uM of each primer, 200 uM dNTP, 1x Advantage Polymerase Buffer (Clontech), and 1x Advantage Polymerase (Clontech). Primer sequences were JNF 232 (5'-GGCAGATGCTAGTCTCAGGG-3'), (SEQ ID NO:20) and JNF 233 (5'-GGGATTTMCCTTGGTCCTG-3'), (SEQ ID NO:21). The PCR reaction was run for 35 cycles at 94° C. for 30 seconds, 63° C. for 30 seconds, and 72° C. for 30 seconds. The PCR products were separated by gel electrophoresis on a 2.0% agarose gel, and the DNA was visualized by ethidium bromide staining. The expression results are shown in FIG. 11.

Example 4

Transfection of HMVEC Cells

On the day before transfection, HMVEC cells were plated at $3.5 \times 10^5$ cells per well in 6-well plates. Cells were incubated in tissue culture flasks at 37° C., in 5% $CO_2$. This seeding resulted in wells that were 85–95% confluent on the day of transfection. All centrifugations were performed in 15-ml polystyrene tubes (VWR, cat# 21008-212) or 50-ml polystyrene tubes (Costar-Corning, cat# 25339-50). A 10x stock of oligofectin G (Sequitur, Inc., Natick, Mass.) was first prepared by dilution in OptiMEM I to 25 ug/ml. Next, 12.5 ml of Oligofectin G per ml of OptiMEM I was added. The diluted stock of lipid was allowed to stand at room temperature for 15 minutes.

A 10x stock (1 uM) of each oligomer (Sequitur, Inc.) in OptiMEM I was prepared by adding 10 µl of oligomer per ml of OptiMEM I. Equal volumes of oligomer and lipid 10x solutions were combined, resulting in a 5x mixture. The oligomer and lipid were allowed to complex by incubating at room temperature for 15 minutes. The oligomer/lipid complexes were then diluted to 1x by adding 4 volumes of HMVEC full growth medium (EGM bullet kit media from Clonetics, San Diego, Calif.), containing 5% FBS. The culture medium was then aspirated from the cells (low passage number HMVEC, Clonetics) and replaced with the appropriate oligomer/lipid complexes (for a 6-well plate, 1.5–2 ml of transfection medium was used per well).

The cells were incubated for 15–18 hours in transfection medium. The cells were then stimulated with 10 ng/ml of TNF-alpha (R&D systems, Minneapolis, Minn.) for 6 hours by adding the TNF directly to the growth medium. The uptake of oligomers was evaluated by the uptake of a fluorescent oligomer by microscopy. The cell viability was evaluated by performing dead stain analysis (Sequitur, Inc.). The cells were then harvested for RNA isolation and TaqMan analysis.

Example 5

Antisense Inhibition of RET16 Gene Expression

In this Example, experiments were performed to determine inhibition of RET16 expression using an antisense oligonucleotides (oligomers or "oligos"). Preferred antisense oligonucleotides are deoxyribonucleotide- or chimeric deoxyribonucleotide/ribonucleotide-based and are provided below. The oligonucleotides were synthesized using chemistry essentially as described in U.S. Pat. No. 5,849,902, which is hereby incorporated herein by reference in its entirety.

The antisense oligos were as follows:
11587: 5'-UGCACAUGCCGCCAAGGAGCCAUCU-3' (SEQ ID NO: 16) and
11590: 5'-GCACUUUACUACGCAGUCCUAGAGA-3'. (SEQ ID NO:22). The 11587 and 11590 antisense oligonucleotides hybridize not only to RET16 polynucleotide (SEQ ID NO:1), but also to the two RET16 splice variant polynucleotides, namely, RET16.2 (SEQ ID NO:12) and RET16.3 (SEQ ID NO:14).

HMVEC cells were transfected with 100 nM (final concentration) of antisense oligomer (11587) or control oligomer (11591: AGAGAUCCUGACGCAUCAUUUCACG), (SEQ ID NO:23) complexed with 2.5 µg/ml of oligofectin G. Four hours after the start of the transfection, the transfection medium was aspirated from the cells and was replaced with full growth medium, as defined in Example 4. Eighteen hours after the start of transfection, cells were stimulated with TNF-alpha (10 ng/ml) for six hours. After stimulation, the cells were lysed in guanidinium buffer and total RNA was isolated from the lysates.

Example 6

TNF-alpha Stimulated HMVEC Cells: ELISA Detection of E-selectin Expression

Cells transfected with antisense oligos (see Example 5) were maintained by the above-described growth conditions (see Example 3) in 24-well plates. The cells were treated with TNF-alpha at 10 ng/ml for 6 hours without a change of medium.

Following the treatment period, the medium was removed, the plates were washed twice with 4° C. PBS (Gibco BRL, Grand Island, N.Y.), and the cells were fixed with 0.5% glutaraldehyde in PBS at 4° C. for 10 minutes. The plate was then flicked gently to remove fixing solution, and 200 µl of 3% goat serum in PBS containing 20 mM EDTA (blocking buffer) was added. The plate was then flicked and biotinylated anti-E-selectin (R&D Systems, Minneapolis, Minn.) was added at 0.25 µg/ml in blocking buffer for 1 hour at 37° C. The wells were washed four times with cold PBS. Next, 100 µl/well of streptavidin conjugated horse radish peroxidase, (1:4000 dilution), (Vector Labs SA-5004) in blocking buffer was added, followed by incubation for 1 hour at 37° C. The wells were then washed four times in cold PBS.

100 µl of TMB peroxidase color reagent (Sigma T8540) was then added, and at the completion of color development, the reaction was terminated with 100 µl of 1 N $H_2SO_4$. Following transfer of the developed color reagent to a 96-well plate, the $OD_{450}$ was read on a multiwell plate reader.

Example 7

Complementary Polynucleotides

Antisense molecules or nucleic acid sequence complementary to the RET16 protein-encoding sequence, or any part thereof, is used to decrease or to inhibit the expression of naturally occurring RET16. Although the use of antisense or complementary oligonucleotides comprising about 15 to 35 base-pairs is described, essentially the same procedure is used with smaller or larger nucleic acid sequence fragments. An oligonucleotide based on the coding sequence of RET16 protein, as shown in FIGS. 1 and 4A, or as depicted in SEQ ID NO:1 or SEQ ID NO:3, for example, is used to inhibit expression of naturally occurring RET16. The complementary oligonucleotide is typically designed from the most unique 5' sequence and is used either to inhibit transcription by preventing promoter binding to the coding sequence, or to inhibit translation by preventing the ribosome from binding to the RET16 protein-encoding transcript.

Using an appropriate portion of the signal and 5' sequence of SEQ ID NO:1 or SEQ ID NO:3, an effective antisense oligonucleotide includes any of about 15–35 nucleotides spanning the region which translates into the signal or 5' coding sequence of the polypeptide as shown in FIG. 2 or FIG. 4. Appropriate oligonucleotides are designed using OLIGO 4.06 software and the RET16 protein coding sequence (SEQ ID NOS:1, 3, and 5). For some purposes, the murine RET16 nucleic acid sequence (SEQ ID NO:6) or the rat RET16 nucleic acid sequence (SEQ ID NO:8) can be employed.

Example 8

Northern Analysis

Northern analysis is used to detect the presence of a transcript of a gene and involves the hybridization of a labeled nucleotide sequence to a membrane on which RNA from a particular cell or tissue type has been bound (See, J. Sambrook et al., supra). Analogous computer techniques using BLAST (S. F. Altschul, 1993, *J. Mol. Evol.*, 36:290–300 and S. F. Altschul et al., 1990, *J. Mol. Evol.*, 215:403–410) are used to search for identical or related molecules in nucleotide databases, such as GenBank or the LIFESEQ database (Incyte Pharmaceuticals). This analysis is much more rapid and less labor-intensive than performing multiple, membrane-based hybridizations. In addition, the sensitivity of the computer search can be modified to determine whether any particular match is categorized as being exact (identical) or homologous.

The basis of the search is the product score, which is defined as follows: (% sequence identity×maximum BLAST score)/100.

The product score takes into account both the degree of similarity between two sequences and the length of the sequence match. For example, with a product score of 40, the match will be exact within a 1–2% error; at 70, the match will be exact. Homologous molecules are usually identified by selecting those which show product scores between 15 and 40, although lower scores can identify related molecules. The results of Northern analysis are reported as a list of libraries in which the transcript encoding RET16 occurs. Abundance and percent abundance are also reported. Abundance directly reflects the number of times that a particular transcript is represented in a cDNA library, and percent

Example 9

Microarrays

For the production of oligonucleotides for a microarray, SEQ ID NO:1 or SEQ ID NO:2, for example, is examined using a computer algorithm which starts at the 3' end of the nucleotide sequence. The algorithm identifies oligomers of defined length that are unique to the gene, have a GC content within a range that is suitable for hybridization and lack predicted secondary structure that would interfere with hybridization. The algorithm identifies specific oligonucleotides of 20 nucleotides in length, i.e., 20-mers. A matched set of oligonucleotides is created in which one nucleotide in the center of each sequence is altered. This process is repeated for each gene in the microarray, and double sets of 20-mers are synthesized in the presence of fluorescent or radioactive nucleotides and arranged on the surface of a substrate. When the substrate is a silicon chip, a light-directed chemical process is used for deposition (WO 95/11995, M. Chee et al.).

Alternatively, a chemical coupling procedure and an ink jet device is used to synthesize oligomers on the surface of a substrate. (WO 95/25116, J. D. Baldeschweiler et al.). As another alternative, a "gridded" array that is analogous to a dot (or slot) blot is used to arrange and link cDNA fragments or oligonucleotides to the surface of a substrate using, for example, a vacuum system, or thermal, UV, mechanical, or chemical bonding techniques. A typical array can be produced by hand, or by using available materials and equipment, and can contain grids of 8 dots, 24 dots, 96 dots, 384 dots, 1536 dots, or 6144 dots. After hybridization, the microarray is washed to remove any non-hybridized probe, and a detection device is used to determine the levels and patterns of radioactivity or fluorescence. The detection device can be as simple as X-ray film, or as complicated as a light scanning apparatus. Scanned fluorescent images are examined to determine degree of complementarity and the relative abundance/expression level of each oligonucleotide sequence in the microarray.

Example 10

Purification of Naturally Occurring RET16 Protein Using Specific Antibodies

Naturally occurring or recombinant RET16 polypeptide is substantially purified by immunoaffinity chromatography using antibodies specific for the RET16 polypeptide, or a peptide derived therefrom. An immunoaffinity column is constructed by covalently coupling anti-RET16 polypeptide antibody to an activated chromatographic resin, such as CNBr-activated SEPHAROSE (Amersham Pharmacia Biotech). After the coupling, the resin is blocked and washed according to the manufacturer's instructions.

Medium containing RET16 polypeptide is passed over the immunoaffinity column, and the column is washed under conditions that allow the preferential absorbance of the RET16 polypeptide (e.g., high ionic strength buffers in the presence of detergent). The column is eluted under conditions that disrupt antibody/RET16 polypeptide binding (e.g., a buffer of pH 2–3, or a high concentration of a chaotrope, such as urea or thiocyanate ion), and RET16 polypeptide is collected.

Example 11

Identification of Molecules that Interact with the RET16 Protein

RET16 polypeptide, or biologically active fragments thereof, are labeled with $^{125}$I Bolton-Hunter reagent (Bolton et al., 1973, *Biochem. J.,* 133:529). Candidate molecules previously arrayed in wells of a multi-welled plate are incubated with the labeled RET16 polypeptide, washed, and any wells having labeled RET16 polypeptide-candidate molecule complexes are assayed. Data obtained using different concentrations of the RET16 polypeptide are used to calculate values for the number, affinity and association of the RET16 polypeptide with the candidate molecules.

Another method suitable for identifying proteins, peptides or other molecules that interact with the RET16 polypeptide include ligand binding assays such as the yeast-two hybrid system as described hereinabove.

Example 12

Method of Creating N- and C-terminal Deletion Mutants Corresponding to the RET16.1, RET16.2, or RET16.3 Polypeptides of the Present Invention As described elsewhere herein, the present invention encompasses the creation of N- and C-terminal deletion mutants, in addition to any combination of N- and C-terminal deletions thereof, corresponding to the RET16.1, RET16.2, or RET16.3 polypeptides of the present invention. A number of methods are available to one skilled in the art for creating such mutants. Such methods can include a combination of PCR amplification and gene cloning methodology. Although one of skill in the art of molecular biology, through the use of the teachings provided or referenced herein, and/or as otherwise known in the art as standard methods, could readily create each deletion mutants of the present invention, exemplary methods are described below.

Briefly, using the isolated cDNA clones encoding the full-length RET16.1, RET16.2, or RET16.3 polypeptide sequences, appropriate primers of about 15–25 nucleotides derived from the desired 5' and 3' positions of SEQ ID NO:1, SEQ ID NO:12, or SEQ ID NO:14 can be designed to PCR amplify, and subsequently clone, the intended N- and/or C-terminal deletion mutant. Such primers can comprise, for example, an initiation and stop codon for the 5' and 3' primer, respectively. Such primers can also comprise restriction sites to facilitate cloning of the deletion mutant post amplification. Moreover, the primers can comprise additional sequences, such as, for example, flag-tag sequences, kozac sequences, or other sequences as discussed and/or referenced herein.

Representative PCR amplification conditions are provided below, although the skilled artisan will appreciate that other conditions can be required and can be employed for efficient amplification. A 100 μl PCR reaction mixture can be prepared using 10 ng of the template DNA (i.e., cDNA clone of RET16.1, RET16.2, or RET16.3), 200 μM 4dNTPs, 1 μM primers, 0.25U Taq DNA polymerase (PE), and standard Taq DNA polymerase buffer. Typical PCR cycling condition are as follows:

| | |
|---|---|
| 20–25 cycles: | 45 seconds, 93 degrees |
| | 2 minutes, 50 degrees |
| | 2 minutes, 72 degrees |
| 1 cycle: | 10 minutes, 72 degrees |

After the final extension step of PCR, 5U Klenow Fragment can be added and incubated for 15 minutes at 30° C.

Upon digestion of the fragment with the NotI and SalI restriction enzymes, the fragment can be cloned into an appropriate expression and/or cloning vector which has been similarly digested (e.g., pSport1, among others). The skilled artisan will appreciate that other plasmids can be equally substituted, and also can be desirable in certain circumstances. The digested fragment and vector are ligated using a DNA ligase, and then used to transform competent *E. coli* cells using methods described herein and/or otherwise known in the art.

The 5' primer sequence for amplifying any additional N-terminal deletion mutants can be determined by reference to the following formula:

(S+(X*3)) to ((S+(X*3))+25), where 'S' is equal to the nucleotide position of the initiating start codon of the RET16.1, RET16.2, or RET16.3 gene (i.e., SEQ ID NO:1, SEQ ID NO:12, or SEQ ID NO:14), and 'X' is equal to the most N-terminal amino acid of the intended N-terminal deletion mutant. The first term provides the start 5' nucleotide position of the 5' primer, while the second term provides the end 3' nucleotide position of the 5' primer corresponding to sense strand of SEQ ID NO:1, SEQ ID NO:12, or SEQ ID NO:14. Once the corresponding nucleotide positions of the primer are determined, the final nucleotide sequence can be created by the addition of applicable restriction site sequences to the 5' end of the sequence, for example. As described herein, the addition of other sequences to the 5' primer may be desired and/or used in certain circumstances (e.g., kozac sequences, and the like).

The 3' primer sequence for amplifying any additional N-terminal deletion mutants can be determined by reference to the following formula:

(S+(X*3)) to ((S+(X*3))−25)

where 'S' is equal to the nucleotide position of the initiating start codon of the RET16.1, RET16.2, or RET16.3 gene (SEQ ID NO:1, 12, or 14), and 'X' is equal to the most C-terminal amino acid of the intended N-terminal deletion mutant. The first term provides the start 5' nucleotide position of the 3' primer, while the second term provides the end 3' nucleotide position of the 3' primer corresponding to the anti-sense strand of SEQ ID NO:1, SEQ ID NO:12, or SEQ ID NO:14. Once the corresponding nucleotide positions of the primer are determined, the final nucleotide sequence can be created by the addition of applicable restriction site sequences to the 5' end of the sequence, for example. As described herein, the addition of other sequences to the 3' primer may be desired in certain circumstances (e.g., stop codon sequences, etc.). The skilled artisan will appreciate that modifications of the above nucleotide positions can be used for optimizing PCR amplification.

The same general formulas provided above can be used in identifying the 5' and 3' primer sequences for amplifying any C-terminal deletion mutant of the present invention. Moreover, the same general formulas provided above can be used in identifying the 5' and 3' primer sequences for amplifying any combination of N-terminal and C-terminal deletion mutants of the present invention. The skilled artisan will appreciate that modifications of the above nucleotide positions can be employed for optimizing PCR amplification.

Alternatively, preferred polypeptides of the present invention comprise polypeptide sequences corresponding to, for example, internal regions of the RET16.1, RET16.2, or RET16.3 polypeptides (e.g., any combination of both N- and C- terminal RET16.1, RET16.2, or RET16.3 polypeptides deletions) of SEQ ID NO:2, SEQ ID NO:13, or SEQ ID NO:15. For example, internal regions could be defined by the equation: amino acid NX to amino acid CX, wherein NX refers to any N-terminal deletion polypeptide amino acid of RET16.1, RET16.2, or RET16.3 (SEQ ID NO: 2, SEQ ID NO:13, or SEQ ID NO:15), and where CX refers to any C-terminal deletion polypeptide amino acid of RET16.1, RET16.2, or RET16.3 (SEQ ID NO: 2, SEQ ID NO:13, or SEQ ID NO:15). Polynucleotides encoding these polypeptides are also provided. The present invention also encompasses the use of these polypeptides as an immunogenic and/or antigenic epitopes as described elsewhere herein.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An isolated polynucleotide comprising a polynucleotide sequence having the sequence of SEQ ID NO:12.

2. The isolated polynucleotide of claim 1, wherein said polynucleotide comprises nucleotides 114 to 1262 of SEQ ID NO:12.

3. The isolated polynucleotide of claim 1, wherein said polynucleotide comprises nucleotides 111 to 1262 of SEQ ID NO:12.

4. A composition comprising an isolated polynucleotide according to claims 1, 2 or 3.

5. An expression vector containing an isolated polynucleotide according to claims 1, 2 or 3.

6. An isolated host cell containing an expression vector according to claim 5.

7. A method for producing a protein involved in the cell signaling cascade comprising the steps of:
   a) culturing the host cell according to claim 6 under conditions suitable for the expression of the polypeptide; and
   b) recovering the polypeptide from the host cell culture.

* * * * *